United States Patent

Basha et al.

[11] Patent Number: 5,248,677
[45] Date of Patent: Sep. 28, 1993

[54] BIOGENTIC AMINE UPTAKE INHIBITORS

[75] Inventors: Fatima Z. Basha, Lake Forest; John F. DeBernardis, Lindenhurst; Robert J. Altenbach, Chicago, all of Ill.

[73] Assignee: Abbott Laboratories, Abbott Park, Ill.

[21] Appl. No.: 947,250

[22] Filed: Sep. 18, 1992

Related U.S. Application Data

[63] Continuation-in-part of Ser. No. 672,011, Mar. 22, 1991, Pat. No. 5,180,733, which is a continuation-in-part of Ser. No. 570,234, Aug. 20, 1990, abandoned, which is a continuation-in-part of Ser. No. 502,601, Mar. 30, 1990, abandoned.

[51] Int. Cl.$^5$ .................. C07D 223/14; C07D 221/06; A61K 31/55; A61K 31/435
[52] U.S. Cl. ..................... 514/217; 514/183; 514/215; 514/287; 540/476; 540/576; 546/65; 546/101
[58] Field of Search .................. 546/65, 101; 540/476, 540/576; 514/183, 215, 217, 287

[56] References Cited

U.S. PATENT DOCUMENTS

| | | | |
|---|---|---|---|
| 4,348,392 | 9/1982 | Fehr et al. | 514/183 |
| 4,666,916 | 5/1987 | Schneider | 546/65 |
| 4,670,443 | 6/1987 | Hartman et al. | 546/101 |
| 5,162,335 | 11/1992 | Vanderwalle et al. | 540/101 |

Primary Examiner—Joseph Paul Brust
Assistant Examiner—Mary Susan H. Gabilan
Attorney, Agent, or Firm—Richard A. Elder; Steven F. Weinstock

[57] ABSTRACT

Compounds of the formula:

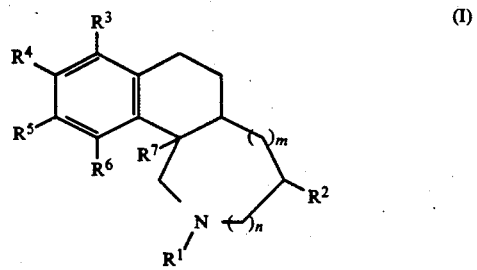

or a pharmaceutically acceptable salt thereof, wherein m is 0, 1 or 2 and n is 0 or 1;

$R^1$ is hydrogen or lower alkyl;

$R^2$ is $C_1$–$C_6$-alkyl substituted with a heterocyclic group or $C_7$–$C_{16}$-arylalkyl, wherein the aryl group is unsubstituted or substituted with from one to three non-hydrogen members independently selected from the group consisting of halogen, $C_1$–$C_6$-alkyl, halo-$C_1$–$C_6$-alkyl, $C_1$–$C_6$-alkoxy, hydroxy, amino and $C_1$–$C_6$-alkylamino;

$R^3$, $R^4$, $R^5$ and $R^6$ are independently selected from the group consisting of hydrogen, $C_1$–$C_6$-alkoxy, $C_1$–$C_6$-alkyl, halogen, and halo-$C_1$–$C_6$-alkyl, or any two of $R^3$, $R^4$, $R^5$ and $R^6$ taken together form a methylenedioxy group; and $R^7$ is hydrogen or $C_1$–$C_6$-alkyl.

These compounds are useful as inhibitors of the neuronal uptake of biogenic amines and for the treatment of affective disorders, such as, for example, depression.

10 Claims, No Drawings

BIOGENTIC AMINE UPTAKE INHIBITORS

CROSS REFERENCE TO RELATED APPLICATIONS

This application is a continuation-in-part of U.S. application Ser. No. 07/672,011, filed Mar. 22, 1991, now U.S. Pat. No. 5,180,733, which is a continuation-in-part of U.S. application Ser. No. 07/570,234, filed Aug. 20, 1990, now abandoned, which is a continuation-in-part of U.S. application Ser. No. 07/502,601, filed Mar. 30, 1990, now abandoned.

TECHNICAL FIELD

This invention relates to novel compounds and compositions thereof which inhibit neuronal biogenic amine uptake, to processes for making such compounds, to synthetic intermediates employed in these processes and to a method of treating affective disorders, such as, for example, depression, with such compounds.

BACKGROUND OF THE INVENTION

Disturbances of mood (affective disorders: cf, R. J. Baldessarini in *Goodman and Gillman's The Pharmacological Basis of Therapeutics*. A. G. Gilman, L. S. Goodman, T. W. Rall and F. Murad, Eds., Macmillan, New York, 1985, pp 412-432) are the most common psychiatric disorders in adults. It has been estimated that 18-23% of women and 8-11% of men in the United States experience at least one major depressive episode in their lifetimes. Unfortunately, there are major drawbacks to the use of currently available agents for treating affective disorders. For example, no antidepressant drug to date has proven to be superior to electroconvulsive shock therapy in the treatment of severe, suicidal depression. Other problems with the use of the various available drugs are delayed onset of activity, poor efficacy, anticholinergic effects at therapeutic doses, cardiotoxicity, convulsions and the danger of taking a fatal overdose. There also exists a large number of untreated individuals and treatment-resistant patients in need of effective therapy.

It is now recognized that depressive conditions may result from reduced amounts of certain biogenic amine neurotransmitters such as noradrenaline (NA), dopamine (DA) and serotonin (5-HT) in the central nervous system (CNS). Therapeutic agents can theoretically raise the synaptic levels of these biogenic amine neurotransmitters in the CNS by two principal mechanisms: by inhibition of the neuronal uptake of the biogenic amine neurotransmitters and by inhibition of the metabolic enzymes responsible for converting the biogenic amines to inactive metabolites, such as, for example, monoamine oxidase (MAO). Biogenic amine uptake inhibitors, including classical antidepressants such as imipramine, desipramine and amitriptyline, as well as newer non-classical agents such as fluoxetine (Prozac) are well known to be therapeutically useful in the treatment of affective disorders such as depression, and related CNS disorders. These clinically-effective agents exert their therapeutic effect through the inhibition of the uptake of biogenic amines into neuronal terminals in the CNS, cf: R. W. Fuller, in *Antidepressants: Neurochemical, Behavioral and Clinical Perspectives*, S. J. Enna, J. D. Malick, and E. Richelson, Eds, Raven Press, New York, 1981, pp 1-12; L. E. Hollister, *Drugs* 1981, 22:129; J. Schildkraut in *Psychopharmacology: A Generation of Progress*, A. M. Lipton, A. DiMascio and K. F. Killam, Eds, Raven Press, New York, 1978, pp 1223-1234; F. Sulser in *Typical and Atypical Antidepressants:Molecular Mechanisms*, E. Costa and G. Racagni, Eds., Raven Press, New York, 1982, pp 1-20; W. Kostowski, *Trends Pharmacol. Sci.* 1981, 2:314; J. Maj, *Trends Pharmacol. Sci.* 1981, 2:80; and C. Kaiser and P. E. Setler in *Burger's Medicinal Chemistry*, 4th ed., M. E. Wolff, Ed., Wiley, New York, 1979, Part III, pp 997-1067.

The novel compounds of the present invention are potent inhibitors of biogenic amine neuronal uptake. Other tetrahydrobenz[e]isoindolines and octahydrobenz[h]isoquinolines, which have distinctly different or no known utility, are disclosed by J. F. DeBernardis, et al., U.S. Pat. No. 4,618,683, issued Oct. 21, 1986; by J. G. Cannon, et al., *J. Med. Chem.*, 1980, 23:502-505; and by W. Oppolozer, *Tetrahedron Letters*, 1974, 1001-4.

SUMMARY OF THE INVENTION

The present invention is directed to compounds that inhibit neuronal biogenic amine uptake of the formula (I):

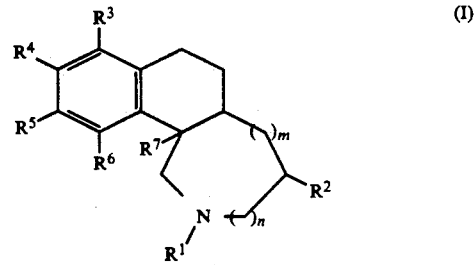

or pharmaceutically-acceptable salts thereof, wherein
m is 0, 1 or 2 and n is 0 or 1;
$R^1$ is hydrogen or $C_1$-$C_6$-alkyl;
$R^2$ is selected from $C_1$-$C_6$-alkyl substituted with a heterocyclic group, and $C_7$-$C_{16}$-arylalkyl, wherein the aryl group is unsubstituted or substituted with from one to three non-hydrogen members independently selected from the group consisting of halogen, $C_1$-$C_6$-alkyl, halo-$C_1$-$C_6$-alkyl, $C_1$-$C_6$-alkoxy, hydroxy, amino and $C_1$-$C_6$-alkylamino;
$R^3$, $R^4$, $R^5$ and $R^6$ are independently selected from hydrogen, $C_1$-$C_6$-alkoxy, $C_1$-$C_6$-alkyl, halogen and halo-$C_1$-$C_6$-alkyl, or any two of $R^3$, $R^4$, $R^5$ and $R^6$ taken together form a methylenedioxy group; and
$R^7$ is hydrogen or $C_1$-$C_6$-alkyl.

The present invention is also directed to pharmaceutical compositions comprising a therapeutically-effective amount of a compound of the formula (I) and a pharmaceutically-acceptable carrier or diluent, as well as to a method of treating depression and related affective disorders in humans and lower mammals, by administration of a compound of formula (I).

DETAILED DESCRIPTION OF THE INVENTION

This invention relates to novel compounds of formula (I) which are selective inhibitors of the neuronal uptake of biogenic amines and, therefore, may be used in the treatment of affective disorders, such as, for example, depression.

In particular, the invention relates to compounds of the formula (I):

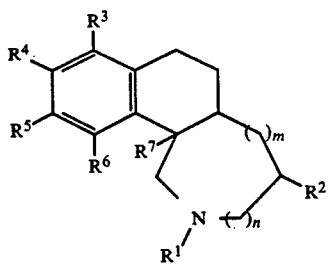

or pharmaceutically-acceptable salts thereof, wherein
m is 0, 1 or 2 and n is 0 or 1;

$R^1$ is hydrogen or $C_1$–$C_6$-alkyl;

$R^2$ is selected from $C_1$–$C_6$-alkyl substituted with a heterocyclic group, and $C_7$–$C_{16}$-arylalkyl, wherein the aryl group is unsubstituted or substituted with from one to three non-hydrogen members independently selected from the group consisting of halogen, $C_1$–$C_6$-alkyl, halo-$C_1$–$C_6$-alkyl, $C_1$–$C_6$-alkoxy, hydroxy, amino and $C_1$–$C_6$-alkylamino;

$R^3$, $R^4$, $R^5$ and $R^6$ are independently selected from hydrogen, $C_1$–$C_6$-alkoxy, $C_1$–$C_6$-alkyl, halogen and halo-$C_1$–$C_6$-alkyl, or any two of $R^3$, $R^4$, $R^5$ and $R^6$ taken together form a methylenedioxy group; and $R^7$ is hydrogen or $C_1$–$C_6$-alkyl.

In one embodiment of the present invention, represented by formula (IA), m and n are both 0 and $R^1$, $R^2$, $R^3$, $R^4$, $R^5$, $R^6$ and $R^7$ are as defined above:

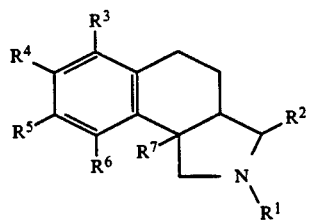

In a second embodiment of the present invention, represented by formula (IB), m is 0, n is 1 and $R^1$, $R^2$, $R^3$, $R^4$, $R^5$, $R^6$ and $R^7$ are as defined above:

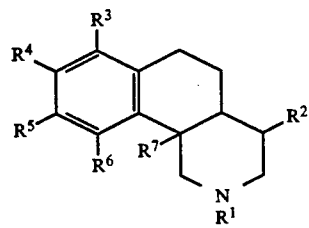

In another embodiment of the present invention, represented by formula (IC), m is 1, n is 0 and $R^1$, $R^2$, $R^3$, $R^4$, $R^5$, $R^6$ and $R^7$ are as defined above:

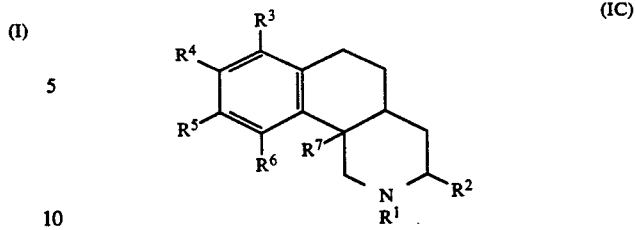

In yet another embodiment of the present invention, represented by formula (ID), m is 2, n is 0 and $R^1$, $R^2$, $R^3$, $R^4$, $R^5$, $R^6$ and $R^7$ are as defined above:

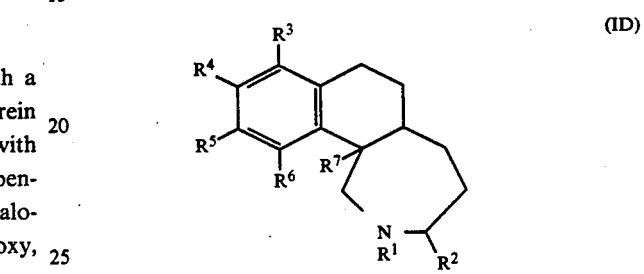

The term "$C_1$–$C_6$-alkoxy" refers to a lower alkyl group, as defined below, which is bonded through an oxygen atom. Examples of lower alkoxy groups are methoxy, ethoxy, isoprpoxy, t-butoxy, and the like.

The term "alkoxyalkyl" as used herein refers to $C_1$–$C_6$-alkyl groups, as defined below, which are substituted with an $C_1$–$C_6$-alkoxy group as defined below.

The term "$C_1$–$C_6$-alkyl" refers to branched or straight chain alkyl groups comprising one to six carbon atoms including, but not limited to, methyl, ethyl, propyl, isopropyl, n-butyl, t-butyl, neopentyl, n-hexyl and the like.

The term "$C_7$–$C_{16}$-arylalkyl" is used herein to mean straight or branched chain radicals of one to six carbon atoms which are substituted with benzene, naphthalene, alkyl, halogen, methoxy, N-methyl or with a benzoheterocycle, as defined below.

The term "benzoheterocycle" is used hereinabove to mean a heterocycle to which is fused a benzene ring, such as, for example, 1,3-benzodioxole, 1,4-benzodioxan, indolyl, indolinyl, benzofuryl, benzothienyl, benzimidazolyl, quinolyl, isoquinolyl, dihydroisoquinolyl, tetrahydroisoquinolyl, and the like. Benzoheterocycles are attached to the alkyl radical through one of the carbon atoms of the heterocycle.

The term "halo-$C_1$–$C_6$-alkyl" refers to a $C_1$–$C_6$-alkyl group, as defined below, bearing at least one halogen substituent, for example fluoromethyl, chloromethyl, bromomethyl, dichloroethyl, trifluoromethyl, and the like.

The term "halogen" as used herein refers to bromo (Br), chloro (Cl), fluoro (F) and iodo (I).

The term heterocycle" or "heterocyclic group" as used herein refers to a 5-, 6- or 7-membered ring, wherein one, two or three nitrogen atoms, one sulfur atom, one nitrogen and one sulfur atom, two nitrogen and one sulfur atom, one oxygen atom, or one nitrogen and one oxygen atom replace from one to three of the carbon atoms, and the 5-membered ring has from 0 to 2 double bonds and the 6-membered ring has from 0 to 3 double bonds. Heterocyclic groups include, but are not limited to, N-methylpyrrolyl, pyridyl, pyrimidinyl, furyl, thienyl, N-methylpyrazolyl, oxazolyl, isoxazolyl, 1,2,4-triazolyl, thiadiazolyl, tetrahydrofuryl, N-methylimidazolyl, N-methyl-piperazinyl, peperidinyl, pyrrolidinyl, thiazolyl, isoxazolinyl, and the like.

The following compounds are representative of the compounds of formula (I):

cis/trans 2,3,3a,4,5,9b-Hexahydro-7-methoxy-3-phenylmethyl-1H-benz[e]isoindole;
cis-2,3,3a,4,5,9b-Hexahydro-7-methoxy-2-methyl-3-phenylmethyl-1H-benz[e]isoindole;
cis-2-Ethyl-2,3,3a,4,5,9b-hexahydro-7-methoxy-3-phenylmethyl-1H-benz[e]isoindole;
cis-2,3,3a,4,5,9b-Hexahydro-7-methoxy-2-phenylethyl-3-phenylmethyl-1H-benz[e]isoindole;
cis-2,3,3a,4,5,9b-Hexahydro-7-methoxy-2-(3-chlorophenyl)ethyl-3-phenylmethyl-1H-benz[e]isoindole;
trans-2,3,3a,4,5,9b-Hexahydro-7-methoxy-3-phenylmethyl-1H-benz[e]isoindole;
trans-2,3,3a,4,5,9b-Hexahydro-7-methoxy-2-methyl-3-phenylmethyl-1H-benz[e]isoindole;
cis-anti-2,3,3a,4,5,9b-Hexahydro-7-methoxy-2-methyl-3-phenylmethyl-1H-benz[e]isoindole;
cis-2,3,3a,4,5,9b-Hexahydro-2-methyl-3-phenylmethyl-1H-benz[e]isoindole;
trans-2,3,3a,4,5,9b-Hexahydro-2-methyl-3-phenylmethyl-1H-benz[e]isoindole;
cis-2,3,3a,4,5,9b-Hexahydro-3-(3-methylphenyl)methyl-1H-benz[e]isoindole;
cis-2,3,3a,4,5,9b-Hexahydro-2-methyl-3-(3-methylphenyl)methyl-1H-benz[e]isoindole;
cis-2-Ethyl-2,3,3a,4,5,9b-hexahydro-3-(3-methylphenyl)methyl-1H-benz[e]isoindole;
trans-2,3,3a,4,5,9b-Hexahydro-2-methyl-3-(3-methylphenyl)methyl-1H-benz[e]isoindole;
cis-3-(3-Fluorophenyl)methyl-2,3,3a,4,5,9b-hexahydro-1H-benz[e]isoindole; cis-3-(3-Fluorophenyl)methyl-2,3,3a,4,5,9b-hexahydro-2-methyl-1H-benz[e]isoindole;
3-(4-Fluorophenyl)methyl-2,3,3a,4,5,9b-hexahydro-1H-benz[e]isoindole;
cis-3-(4-Fluorophenyl)methyl-2,3,3a,4,5,9b-hexahydro-2-methyl-1H-benz[e]isoindole;
trans-2,3,3a,4,5,9b-Hexahydro-3-(3-methoxyphenyl)methyl-1H-benz[e]isoindole;
trans-2,3,3a,4,5,9b-Hexahydro-3-(3-methoxyphenyl)methyl-2-methyl-1H-benz[e]isoindole;
cis-2,3,3a,4,5,9b-Hexahydro-6-methoxy-3-phenylmethyl-1H-benz[e]isoindole;
cis-2,3,3a,4,5,9b-Hexahydro-6-methoxy-2-methyl-3-phenylmethyl-1H-benz[e]isoindole;
cis-2-Ethyl-2,3,3a,4,5,9b-hexahydro-6-methoxy-3-phenylmethyl-1H-benz[e]isoindole;
cis-3-(3-Fluorophenyl)methyl-2,3,3a,4,5,9b-hexahydro-6-methoxy-2-methyl-1H-benz[e]isoindole;
cis-2-Ethyl-3-(3-fluorophenyl)methyl-2,3,3a,4,5,9b-hexahydro-6-methoxy-1H-benz[e]isoindole;
trans-3-(3-Fluorophenyl)methyl-2,3,3a,4,5,9b-hexahydro-7-methoxy-1H-benz[e]isoindole;
trans-3-(3-Fluorophenyl)methyl-2,3,3a,4,5,9b-hexahydro-7-methoxy-2-methyl-1H-benz[e]isoindole;
cis-3-(3-Fluorophenyl)methyl-2,3,3a,4,5,9b-hexahydro-7-methoxy-2-methyl-1H-benz[e]isoindole;
cis-2,3,3a,4,5,9b-Hexahydro-7-methoxy-3-(3-methoxyphenyl)methyl-2-methyl-1H-benz[e]isoindole;
cis-2,3,3a,4,5,9b-Hexahydro-7-methoxy-2-methyl-3-(3-phenyl-1-propyl)-1H-benz[e]isoindole;
cis-5,6-Dimethoxy-2,3,3a,4,5,9b-hexahydro-3-phenylmethyl-1H-benz[e]isoindole;
cis-6,7-Dimethoxy-2,3,3a,4,5,9b-hexahydro-2-methyl-3-phenylmethyl-1H-benz[e]isoindole;
trans-6,7-Dimethoxy-2,3,3a,4,5,9b-hexahydro-3-(3-methylphenyl)methyl-1H-benz[e]isoindole;
trans-6,7-Dimethoxy-2,3,3a,4,5,9b-hexahydro-2-methyl-3-(3-methylphenyl)methyl-1H-benz[e]isoindole;
trans-2,3,3a,4,5,9b-Hexahydro-2-methyl-6,7-methylenedioxy-3-(3-methylphenyl)methyl-1H-benz[e]isoindole;
trans-3-(3-Fluorophenyl)methyl-2,3,3a,4,5,9b-hexahydro-2-methyl-6,7-methylenedioxy-1H-benz[e]isoindole;
cis-2,3,3a,4,5,9b-Hexahydro-6-methoxy-9-methyl-3-phenylmethyl-1H-benz[e]isoindole;
cis-2,9-Dimethyl-2,3,3a,4,5,9b-hexahydro-6-methoxy-3-phenylmethyl-1H-benz[e]isoindole;
cis-2-Ethyl-9-(4-(4-fluorophenyl)butyloxy)-2,3,3a,4,5,9b-hexahydro-6-methoxy-3-phenylmethyl-1H-benz[e]isoindole;
trans-3-(3-Fluorophenyl)methyl-2,3,3a,4,5,9b-hexahydro-2-methyl-6,7,8-trimethoxy-1H-benz[e]isoindole;
3-(3-Fluorophenyl)methyl-2,3,3a,4,5,9b-hexahydro-2-methyl-6,7,9-trimethoxy-1H-benz[e]isoindole;
6,7-Dimethoxy-9-fluoro-3-(3-fluorophenyl)methyl-2,3,3a,4,5,9b-hexahydro-2-methyl-1H-benz[e]isoindole;
cis-7-Bromo-2,3,3a,4,5,9b-hexahydro-3-phenylmethyl-1H-benz[e]isoindole;
cis-7-Bromo-2,3,3a,4,5,9b-hexahydro-2-methyl-3-phenylmethyl-1H-benz[e]isoindole;
cis-3-(2-Chloro-5-N-ethyl-N-methylaminophenyl)methyl-2,3,3a,4,5,9b-hexahydro-2-methyl-1H-benz[e]isoindole;
3-(3-Chlorophenyl)methyl-2,3,3a,4,5,9b-hexahydro-2-methyl-1H-benz[e]isoindole;
3-(3-Chlorophenyl)methyl-2,3,3a,4,5,9b-hexahydro-2-methyl-1H-benz[e]isoindole;
trans-7-Chloro-3-(3-chlorophenyl)methyl-2,3,3a,4,5,9b-hexahydro-2-methyl-1H-benz[e]isoindole;
cis-7-Chloro-3-(3-chlorophenyl)methyl-2,3,3a,4,5,9b-hexahydro-2-methyl-1H-benz[e]isoindole;
1,2,3,4,4a,5,6,10b-Octahydro-4-phenylmethyl-benz[f]isoquinoline;
cis-2-Methyl-1,2,3,4,4a,5,6,10b-octahydro-4-phenylmethyl-benz[f]isoquinoline;
trans-2-Methyl-1,2,3,4,4a,5,6,10b-octahydro-4-phenylmethyl-benz[f]isoquinoline;
8-Methoxy-1,2,3,4,4a,5,6,10b-octahydro-benz[f]isoquinoline;
cis-8-Methoxy-2-methyl-1,2,3,4,4a,5,6,10b-octahydro-benz[f]isoquinoline;
cis/syn-8-Methoxy-2-methyl-1,2,3,4,4a,5,6,10b-octahydro-benz[f]isoquinoline;
(+)-cis/anti-8-Methoxy-2-methyl-1,2,3,4,4a,5,6,10b-octahydro-benz[f]isoquinoline;
(−)-cis/anti-8-Methoxy-2-methyl-1,2,3,4,4a,5,6,10b-octahydro-benz[f]isoquinoline;
(+)-cis/syn-8-Methoxy-2-methyl-1,2,3,4,4a,5,6,10b-octahydro-benz[f]isoquinoline;
(−)-cis/syn-8-Methoxy-2-methyl-1,2,3,4,4a,5,6,10b-octahydro-benz[f]isoquinoline;
(−)-trans/syn8-Methoxy-2-methyl-1,2,3,4,4a,5,6,10b-octahydro-benz[f]isoquinoline;
(+)-trans/syn8-Methoxy-2-methyl-1,2,3,4,4a,5,6,10b-octahydro-benz[f]isoquinoline;

2-Ethyl-8-methoxy-1,2,3,4,4a,5,6,10b-octahydro-benz[f]isoquinoline;
2-Ethyl-8-methoxy-1,2,3,4,4a,5,6,10b-octahydro-4-phenylmethyl-benz[f]isoquinoline;
2,10b-Diethyl-8-ethoxy-1,2,3,4,4a,5,6,10b-octahydro-4-phenylmethyl-benz[f]isoquinoline;
2,3,3a,4,5,9b-Hexahydro-2-methyl-6,7-methylenedioxy-3-(2-thienyl)methyl-1H-benz[e]isoindole;
3-(2-Furanyl)methyl-2,3,3a,4,5,9b-hexahydro-2-methyl-6,7-methylenedioxy-1H-benz[e]isoindole;
3-(2-Cyclopentadienyl)methyl-2,3,3a,4,5,9b-hexahydro-2-methyl-6,7-methylenedioxy-1H-benz[e]isoindole;
2,3,3a,4,5,9b-Hexahydro-2-methyl-3-(N-methyl-2-pyrolyl)methyl-6,7-methylenedioxy-1H-benz[e]isoindole;
2,3,3a,4,5,9b-Hexahydro-2-methyl-6,7-methylenedioxy-3-(2-pyridinyl)methyl-1H-benz[e]isoindole;
3-(1,3-Dioxalan-2-yl)-2,3,3a,4,5,9b-hexahydro-2-methyl-6,7-methylenedioxy-1H-benz[e]isoindole;
9-Fluoro-2,3,3a,4,5,9b-hexahydro-6,7-methylenedioxy-3-phenylmethyl-1H-benz[e]isoindole;
9-Fluoro-2,3,3a,4,5,9b-hexahydro-2-methyl-6,7-methylenedioxy-3-phenylmethyl-1H-benz[e]isoindole;
9-Fluoro-2,3,3a,4,5,9b-hexahydro-2-methyl-6,7-methylenedioxy-3-(2-thienyl)methyl-1H-benz[e]isoindole;
9-Fluoro-3-(2-furanyl)methyl-2,3,3a,4,5,9b-hexahydro-2methyl-6,7-methylenedioxy-1H-benz[e]isoindole;
9-Fluoro-2,3,3a,4,5,9b-hexahydro-2-methyl-3-(N-methyl-2-pyrolyl)methyl-6,7-methylenedioxy-1H-benz[e]isoindole;
9-Fluoro-2,3,3a,4,5,9b-hexahydro-2-methyl-6,7-methylenedioxy-3-(2-pyridinyl)methyl-1H-benz[e]isoindole;
3-(1,3-Dioxalan-2-yl)-9-fluoro-2,3,3a,4,5,9b-hexahydro-2-methyl-6,7-methylenedioxy-1H-benz[e]isoindole;
2-Methyl-1,2,3,4,4a,5,6,10b-octahydro-3-phenylmethyl-benz[f]isoquinoline;
8-Methoxy-2-methyl-1,2,3,4,4a,5,6,10b-octahydro-3-phenylmethyl-benz[f]isoquinoline;
2-Methyl-1,3,4,5,5a,6,7,11b-octahydro-3-phenylmethyl-2H-naphth[1,2-c]azepine;
8-Methoxy-2-methyl-1,3,4,5,5a,6,7,11b-octahydro-3-phenylmethyl-2H-naphth[1,2-c]azepine;
cis/trans 2,3,3a,4,5,9b-Hexahydro-3-phenylmethyl-6-trifluoromethyl-1H-benz[e]isoindole;
cis-2,3,3a,4,5,9b-Hexahydro-2-methyl-3-phenylmethyl-6-trifluoromethyl-1H-benz[e]isoindole;
cis-2-Ethyl-2,3,3a,4,5,9b-hexahydro-3-phenylmethyl-6-trifluoromethyl-1H-benz[e]isoindole;
cis/trans 2,3,3a,4,5,9b-Hexahydro-3-phenylmethyl-7-trifluoromethyl-1H-benz[e]isoindole;
cis-2,3,3a,4,5,9b-Hexahydro-2-methyl-3-phenylmethyl-7-trifluoromethyl-1H-benz[e]isoindole;
cis-2-Ethyl-2,3,3a,4,5,9b-hexahydro-3-phenylmethyl-7-trifluoromethyl-1H-benz[e]isoindole;
trans-2,3,3a,4,5,9b-Hexahydro-3-phenylmethyl-6-trifluoromethyl-1H-benz[e]isoindole;
trans-2,3,3a,4,5,9b-Hexahydro-2-methyl-3-phenylmethyl-6-trifluoromethyl-1H-benz[e]isoindole;
trans-2,3,3a,4,5,9b-Hexahydro-3-phenylmethyl-7-trifluoromethyl-1H-benz[e]isoindole;
trans-2,3,3a,4,5,9b-Hexahydro-2-methyl-3-phenylmethyl-7-trifluoromethyl-1H-benz[e]isoindole;
cis-2,3,3a,4,5,9b-Hexahydro-3-(3-methylphenyl)methyl-6-trifluoromethyl-1H-benz[e]isoindole;
cis-2,3,3a,4,5,9b-Hexahydro-2-methyl-3-(3-methylphenyl)methyl-6-trifluoromethyl-1H-benz[e]isoindole;
cis-2-Ethyl-2,3,3a,4,5,9b-hexahydro-3-(3-methylphenyl)methyl-6-trifluoromethyl-1H-benz[e]isoindole;
cis-2,3,3a,4,5,9b-Hexahydro-3-(3-methylphenyl)methyl-7-trifluoromethyl-1H-benz[e]isoindole;
cis-2,3,3a,4,5,9b-Hexahydro-2-methyl-3-(3-methylphenyl)methyl-7-trifluoromethyl-1H-benz[e]isoindole;
cis-2-Ethyl-2,3,3a,4,5,9b-hexahydro-3-(3-methylphenyl)methyl-7-trifluoromethyl-1H-benz[e]isoindole;
trans-2,3,3a,4,5,9b-Hexahydro-2-methyl-3-(3-methylphenyl)methyl-6-trifluoromethyl-1H-benz[e]isoindole;
trans-2,3,3a,4,5,9b-Hexahydro-2-methyl-3-(3-methylphenyl)methyl-7-trifluoromethyl-1H-benz[e]isoindole;
cis-3-(3-Fluorophenyl)methyl-2,3,3a,4,5,9b-hexahydro-6-trifluoromethyl-1H-benz[e]isoindole;
cis-3-(3-Fluorophenyl)methyl-2,3,3a,4,5,9b-hexahydro-2-methyl-6-trifluoromethyl-1H-benz[e]isoindole;
cis-3-(3-Fluorophenyl)methyl-2,3,3a,4,5,9b-hexahydro-7-trifluoromethyl-1H-benz[e]isoindole;
cis-3-(3-Fluorophenyl)methyl-2,3,3a,4,5,9b-hexahydro-2-methyl-7-trifluoromethyl-1H-benz[e]isoindole;
3-(4-Fluorophenyl)methyl-2,3,3a,4,5,9b-hexahydro-6-trifluoromethyl-1H-benz[e]isoindole;
cis-3-(4-Fluorophenyl)methyl-2,3,3a,4,5,9b-hexahydro-2-methyl-6-trifluoromethyl-1H-benz[e]isoindole;
3-(4-Fluorophenyl)methyl-2,3,3a,4,5,9b-hexahydro-7-trifluoromethyl-1H-benz[e]isoindole;
cis-3-(4-Fluorophenyl)methyl-2,3,3a,4,5,9b-hexahydro-2-methyl-7-trifluoromethyl-1H-benz[e]isoindole;
(+)-cis-2-Methyl-1,3,4,5,5a,6,7,11b-octahydro-3-phenylmethyl-2H-naphth[1,2-c]azepine;
(−)-cis-2-Methyl-1,3,4,5,5a,6,7,11b-octahydro-3-phenylmethyl-2H-naphth[1,2-c]azepine;
trans-2-Methyl-1,3,4,5,5a,6,7,11b-octahydro-3-phenylmethyl-2H-naphth[1,2-c]azepine;
as well as pharmaceutically-acceptable salts thereof.

The following compounds are representative of the preferred compounds of formula (I):
2,3,3a,4,5,9b-Hexahydro-7-methoxy-2-methyl-3-phenylmethyl-1H-benz[e]isoindole;
2-Ethyl-2,3,3a,4,5,9b-hexahydro-7-methoxy-3-phenylmethyl-1H-benz[e]isoindole;
2,3,3a,4,5,9b-Hexahydro-2-methyl-3-phenylmethyl-1H-benz[e]isoindole;
2,3,3a,4,5,9b-Hexahydro-2-methyl-3-(3-methylphenyl)methyl-1H-benz[e]isoindole;
2-Ethyl-2,3,3a,4,5,9b-hexahydro-3-(3-methylphenyl)methyl-1H-benz[e]isoindole;
3-(3-Fluorophenyl)methyl-2,3,3a,4,5,9b-hexahydro-2-methyl-1H-benz[e]isoindole;
2,3,3a,4,5,9b-Hexahydro-6-methoxy-2-methyl-3-phenylmethyl-1H-benz[e]isoindole;
2-Ethyl-2,3,3a,4,5,9b-hexahydro-6-methoxy-3-phenylmethyl-1H-benz[e]isoindole;
3-(3-Fluorophenyl)methyl-2,3,3a,4,5,9b-hexahydro-6-methoxy-2-methyl-1H-benz[e]isoindole;
2-Ethyl-3-(3-fluorophenyl)methyl-2,3,3a,4,5,9b-hexahydro-6-methoxy-1H-benz[e]isoindole;
3-(3-Fluorophenyl)methyl-2,3,3a,4,5,9b-hexahydro-7-methoxy-2-methyl-1H-benz[e]isoindole;
5,6-Dimethoxy-2,3,3a,4,5,9b-hexahydro-2-methyl-3-phenylmethyl-1H-benz[e]isoindole;
3-(3-Fluorophenyl)methyl-2,3,3a,4,5,9b-hexahydro-2-methyl-6,7-methylenedioxy-1H-benz[e]isoindole;

2-Methyl-1,2,3,4,4a,5,6,10b-octahydro-3-phenylmethyl-benz[f]isoquinoline;

8-Methoxy-2-methyl-1,2,3,4,4a,5,6,10b-octahydro-3-phenylmethyl-benz[f]isoquinoline;

2-Methyl-1,3,4,5,5a,6,7,11b-octahydro-3-phenylmethyl-2H-naphth[1,2-c]azepine; and 8-Methoxy-2-methyl-1,3,4,5,5a,6,7,11b-octahydro-3-phenylmethyl-2H-naphth[1,2-c]azepine;

(−)-cis-2-Methyl-1,3,4,5,5a,6,7,11b-octahydro-3-phenylmethyl-2H-naphth[1,2-c]azepine hydrochloride;

as well as pharmaceutically-acceptable salts thereof.

The following compounds are representative of the more preferred compounds of formula (I):

2-Ethyl-2,3,3a,4,5,9b-hexahydro-7-methoxy-3-phenylmethyl-1H-benz[e]isoindole;

2-Ethyl-2,3,3a,4,5,9b-hexahydro-3-(3-methylphenyl)-methyl-1H-benz[e]isoindole;

2-Ethyl-2,3,3a,4,5,9b-hexahydro-6-methoxy-3-phenylmethyl-1H-benz[e]isoindole;

2-Ethyl-3-(3-fluorophenyl)methyl-2,3,3a,4,5,9b-hexahydro-6-methoxy-1H-benz[e]isoindole;

2-Methyl-1,2,3,4,4a,5,6,10b-octahydro-3-phenylmethyl-benz[f]isoquinoline;

2-Methyl-1,3,4,5,5a,6,7,11b-octahydro-3-phenylmethyl-2H-naphth[1,2-c]azepine; and 8-Methoxy-2-methyl-1,3,4,5,5a,6,7,11b-octahydro-3-phenylmethyl-2H-naphth[1,2-c]azepine;

(−)-cis-2-Methyl-1,3,4,5,5a,6,7,11b-octahydro-3-phenylmethyl-2H-naphth[1,2-c]azepine hydrochloride;

as well as pharmaceutically-acceptable salts thereof.

Certain compounds of this invention exist in optically active forms. The pure d isomers and pure/isomers, as well as mixtures thereof including the racemic mixtures, are contemplated by this invention. Additional asymmetric centers may be present in a substituent such as an alkyl group. All such isomers as well as mixtures thereof are intended to be within the scope of this invention. In particular, stereochemistry of the hydrogen atoms and substituents at the ring junction and at the carbon to which $R^2$ is attached, as shown in formula (I), can independently be either axial or equatorial unless specifically noted otherwise.

The compounds of this invention are synthesized by reaction schemes IA through VII illustrated below. It should be understood that $R^1$-$R^7$ as used herein correspond to the R groups identified by formula (I). The reactions are performed in a solvent appropriate to the reagents and materials employed are suitable for the transformation being effected. It is understood by those skilled in the art of organic synthesis that the functionality present on the phenyl ring and other portions of the molecule must be consistent with the chemical transformation proposed. This will, on occasion, necessitate judgment as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of amino-protecting groups is well known in the art for protecting amino groups against undesirable reactions during a synthetic procedure and many such protecting groups are known, c.f., T. H. Greene, *Protective Groups in Organic Synthesis*, John Wiley & Sons, New York (1981).

Scheme IA

Scheme IA

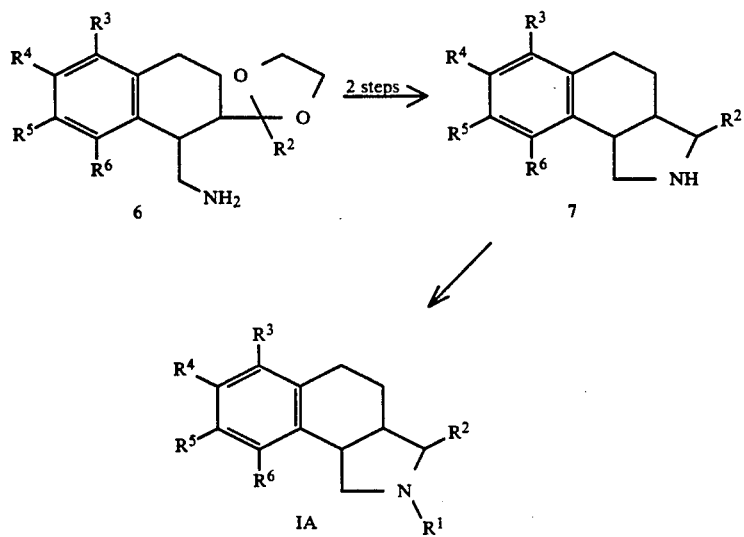

Scheme IA

According to reaction scheme 1A, the unsaturated nitriles of Formula 2 are prepared by Lewis acid catalyzed trimethylsilyl cyanide addition to known tetralones of Formula 1, followed by acid-catalyzed elimination of the intermediate adduct. The conjugate addition of 2-lithio-2-substituted-1,3-dithianes of the Formula 3 to the unsaturated nitriles of Formula 2 affords the 1,4-Michael addition products of Formula 4 as a mixture of cis and trans isomers. The mercuric chloride catalyzed dithiane-ketal exchange in ethylene glycol/THF at reflux affords the corresponding ketals of Formula 5.

The reduction of the nitriles of Formula 5 to the aminomethyl compounds of Formula 6 is accomplished by catalytic hydrogenation with a suitable catalyst such as Raney nickel in a suitable solvent, such as methanol or by treatment with a suitable reducing agent, such as, for example, lithium aluminum hydride. The desired benzoisoindolines of Formula 7 are obtained in a one pot reaction from the hydrolysis of aminomethyl ketals of Formula 6 with a suitable acid, such as hydrochloric acid, in a polar solvent such as THF, to the keto-amine. The keto-amine is in equilibrium with the corresponding iminium compound which is readily reduced by sodium cyanoborohydride. The compounds of Formula 7 are converted to the N-alkylated compounds of Formula IA by alkylation under standard conditions, such as hydrogenation in the presence of a suitable catalyst such as palladium on carbon (Pd/C), and a suitable carbonyl compound, such as, for example, formaldehyde.

Scheme IB

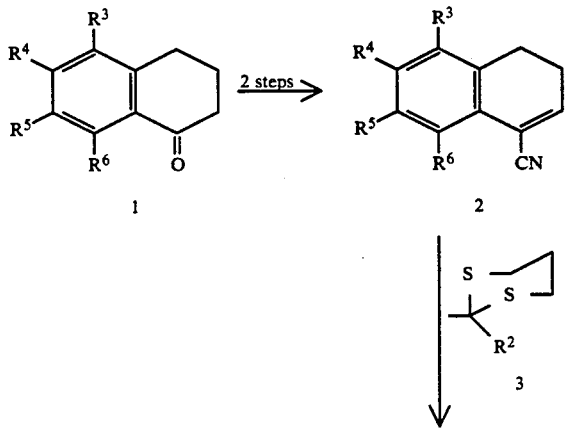

-continued

Scheme IB

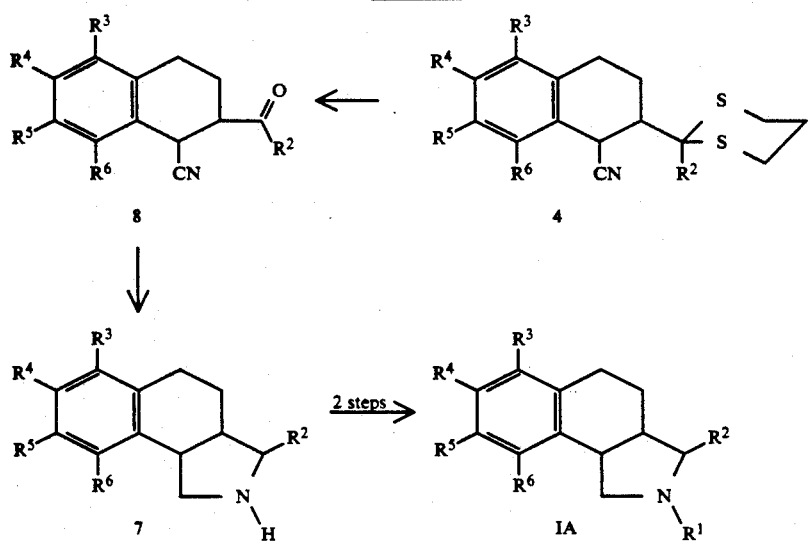

Scheme IB

According to reaction scheme IB, the 1,4-Michael addition products of Formula 4 are hydrolyzed to the corresponding ketones of Formula 8 with mercuric chloride and a suitable base, such as calcium carbonate, in a suitable polar solvent, such as acetonitrile/water. Reduction of the keto-nitriles of Formula 8, for example, by hydrogenation with a suitable catalyst such as Raney nickel in a polar solvent such as methanol, in the presence of a suitable base, such as triethylamine, affords the isoindoline compounds of Formula 7, predominantly as the trans isomer. The compounds of Formula 7 are converted to the N-alkylated compounds of Formula IA by alkylation under standard conditions such as hydrogenation in the presence of a suitable catalyst, such as palladium on carbon, and a suitable carbonyl compound such as formaldehyde. Alternately, they may be alkylated by treatment with an alkylating agent, such as dimethyl sulfate or methyl iodide, in the presence of a suitable base, such as sodium hydide, sodium ethoxide or potassium carbonate, in a suitable solvent.

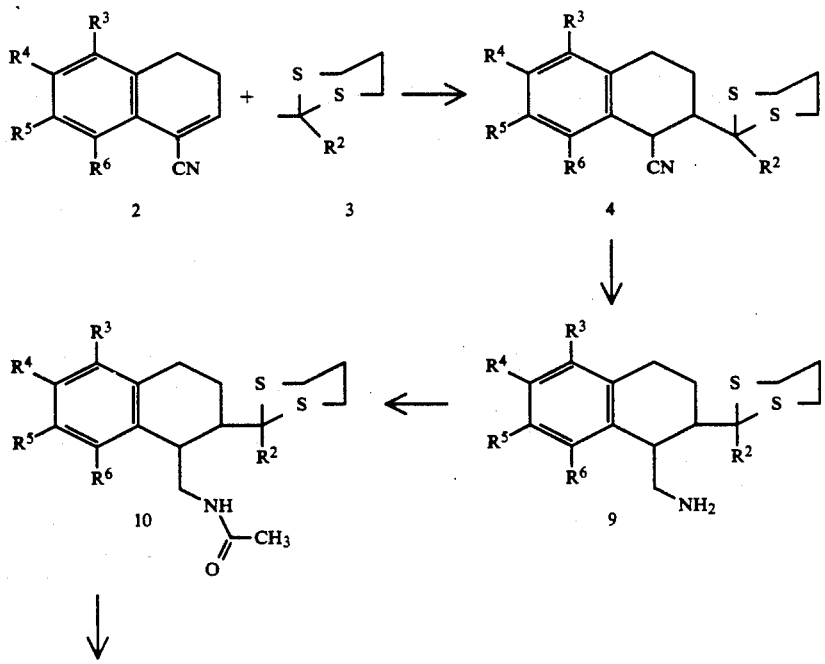

Scheme IC

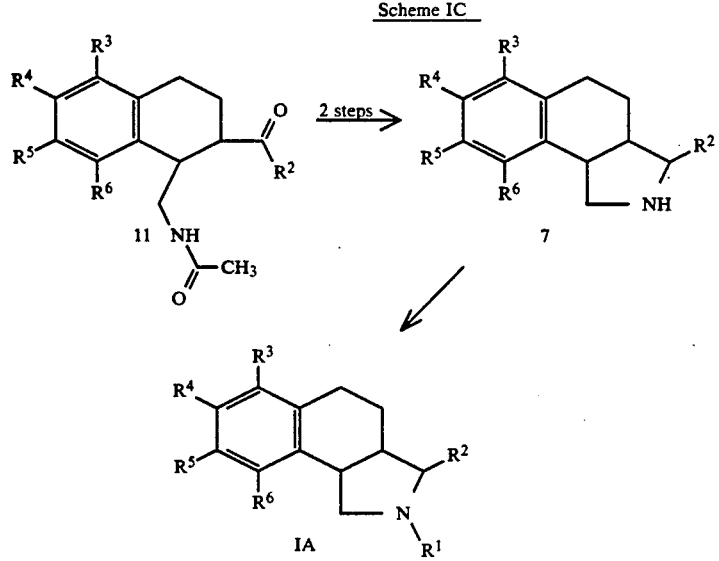

Scheme IC

According to reaction scheme IC, the compounds of Formula 4 are reduced to the aminomethyl dithiane derivatives of Formula 9 with a suitable reducing agent, such as, for example, diborane in THF. The resulting amino compounds of Formula 9 are acylated with a suitable acylating agent, such as acetic anhydride, in a suitable base such as pyridine, to yield the N-acetyl compounds of Formula 10. N-bromosuccinimide (NBS) catalyzed dithiane hydrolysis of compounds of the Formula 10 in a polar solvent, such as acetone/water or acetonitrile/water, affords the corresponding N-protected keto-amine compounds of Formula 11. Hydrolysis of N-acetyl group of compounds of Formula 10 with a suitable acid such as aqueous hydrochloric acid, followed by intramolecular reductive amination, affords the isoindoline compounds of Formula 7. The compounds of Formula 7 are converted to the N-alkylated compounds of Formula IA by alkylation under standard conditions, such as hydrogenation in the presence of a suitable catalyst, such as palladium on carbon, and a suitable carbonyl compound such as formaldehyde, or by treatment with an alkylating agent, such as dimethyl sulfate or methyl iodide, in the presence of a suitable base, such as sodium hydide, sodium ethoxide or potassium carbonate, in a suitable solvent.

Scheme II

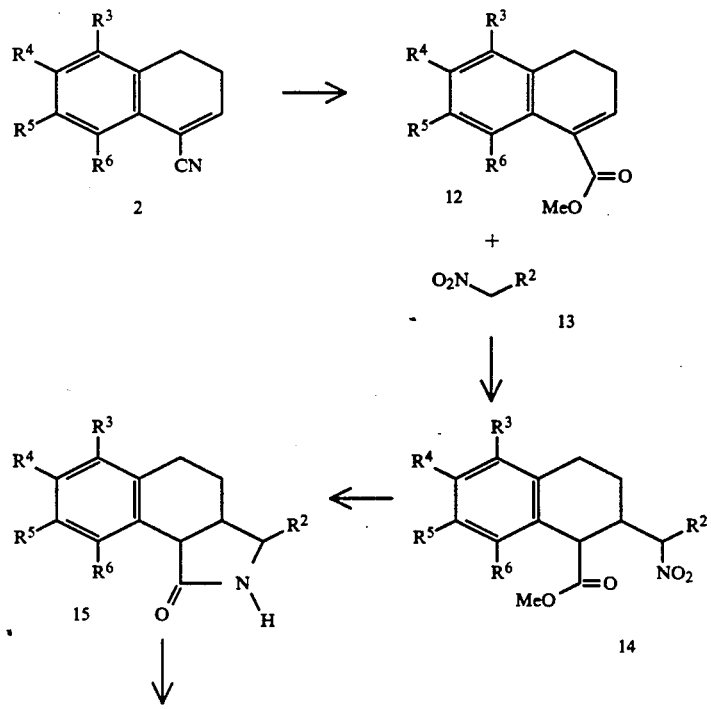

Scheme II

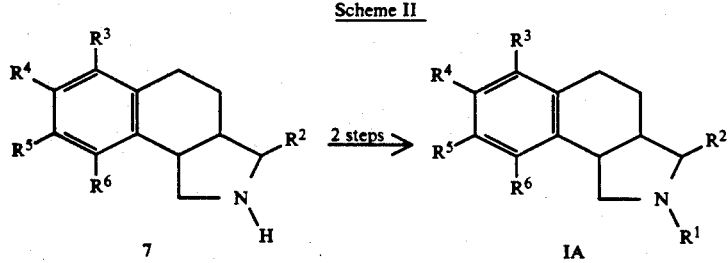

Scheme II

According to reaction scheme II, the unsaturated nitriles of Formula 2 are converted to the corresponding unsaturated esters by treatment with a suitable acid, such as sulfuric acid, in a suitable alcohol solvent, for example methanol which gives the methyl esters of Formula 12. An unsaturated ester of Formula 12 is, in turn, reacted with a nitromethane derivative of Formula 13 to afford an adduct of Formula 14. The adducts of Formula 14 are cyclized to the compounds of Formula 15 by treatment with a suitable reducing agent for reducing the nitro group without reducing the ester, for example zinc and acetic acid. The lactams of Formula 15 are reduced to the isoindoline compounds of Formula 7 with a suitable reducing agent, such as, for example, borane. The compounds of Formula 7 are converted to the N-alkylated compounds of Formula IA by alkylation under standard conditions, such as hydrogenation in the presence of a suitable catalyst, such as palladium on carbon, and a suitable carbonyl compound such as formaldehyde or by treatment with an alkylating agent, such as dimethyl sulfate or methyl iodide, in the presence of a suitable base, such as sodium hydide, sodium ethoxide or potassium carbonate, in a suitable solvent.

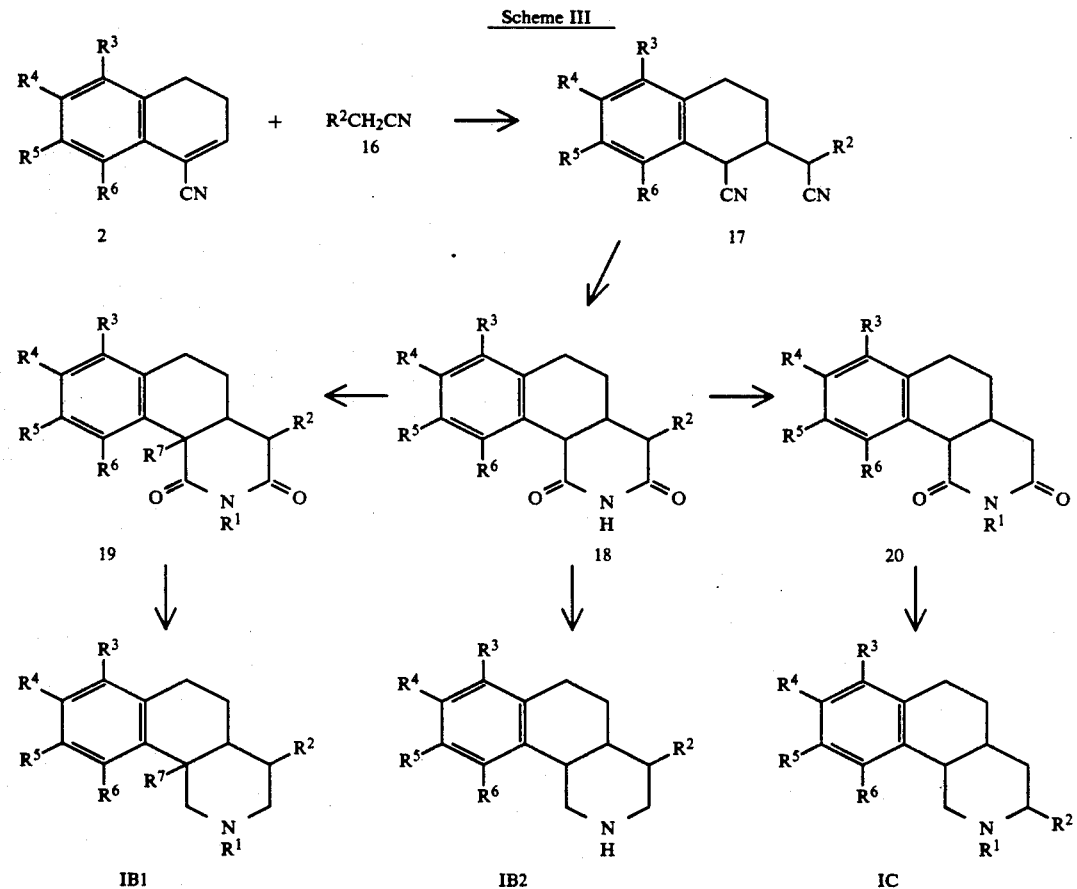

Scheme III

According to the reaction scheme III, the conjugate addition of the compounds of Formula 16 (wherein $R^2$ may not be substituted with halogen) with the unsaturated nitrile of Formula 2 (wherein $R^3$, $R^4$, $R^5$ and $R^6$ may not be halogen) yields the dinitriles of Formula 17 as a mixture of the cis and trans isomers. Hydrolysis of compounds of Formula 17 with a suitable acid, such as hydrobromic acid in methylene chloride, followed by DMF/water affords the cis imido compounds of Formula 18. Reduction of the cis imido compounds of Formula 16 with a suitable reducing agent, such as diborane in THF, affords the desired isoquinolines of Formulas IB1. Alternately compounds of Formula 17, wherein any of any or all of $R^3$, $R^4$, $R^5$ or $R^6$ are methoxy, are reagent, such as benzyl magnesium bromide, mild acid, for example, hydrochloric acid in methanol, and sodium cyanoborohydride to afford the compounds of Formula IC.

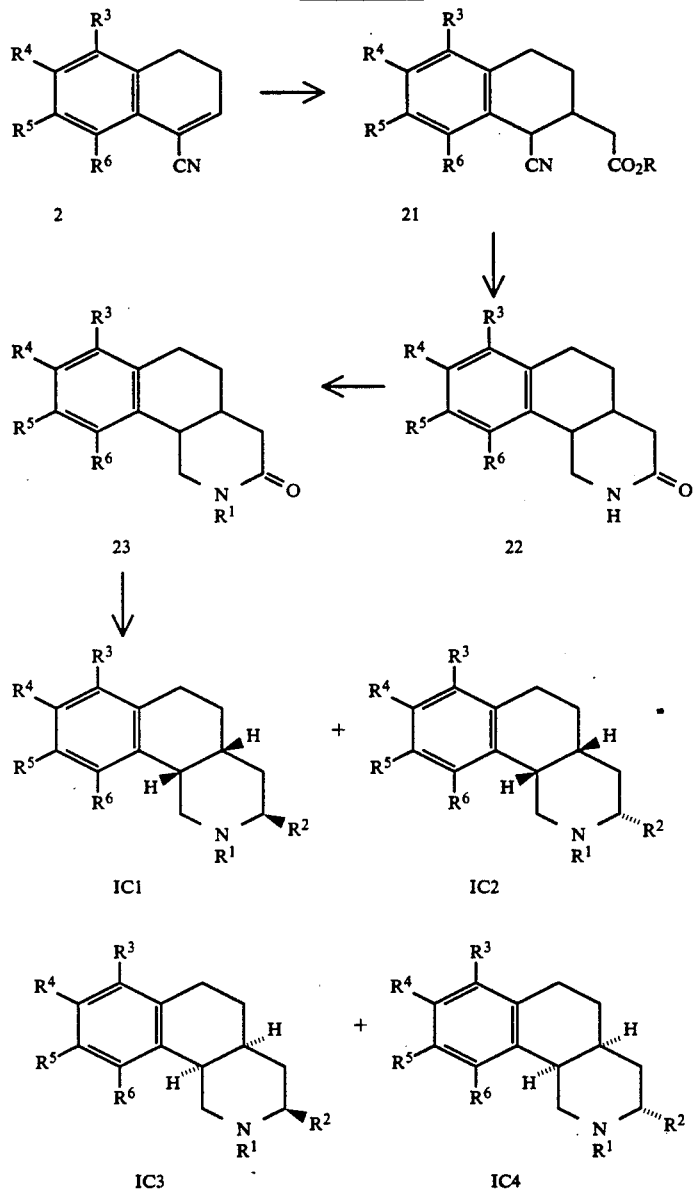

Scheme IV cyclized to compounds of Formula 18 in a suitable acid, for example, a mixture of sulfuric and acetic acids, in which the methoxy group has been hydrolyzed to a hydroxy group. These compounds, in turn are converted to compounds of Formula 19 by standard alkylation procedures. Reduction of the imido compounds of Formula 19 is carried out as discussed above for compounds of Formula 16 to afford the compounds of Formula IB2.

Compounds of Formula 18 in which $R^2$ is hydrogen are alkylated by treatment with a suitable alkylating agent such as methyl iodide or dimethylsulfate in the presence of a suitable base, for example, potasium or sodium t-butoxide or sodium hydride, to afford the compounds of Formula 20. The compounds of Formula 20 are, in turn, treated sequentially with a Grignard Scheme IV According to reaction scheme IV, an unsaturated nitrile of Formula 2 is condensed with an acetate ester, for example ethyl acetate, in the presence of a suitable base, such as diisopropylamide (LDA), to afford the adducts of Formula 21. The compounds of Formula 21 are cyclized to the compounds of Formula 22 by reduction of the nitrile group to the aminomethyl group. The reduction can be carried out by catalytic hydrogenation or by treatment with a suitable reducing agent, such as, for example lithium aluminum hydride. The lactams of Formula 22 are alkylated by standard alkylation procedures, for example, treatment with methyl iodide in the presence of a suitable base, such as potassium t-butoxide, to afford the compounds of Formula 23. The compounds of Formula 23 are treated sequentially with a Grignard reagent, for example, benzylmagnesium chloride, a mild acid, such as methanolic hydrogen chloride, and a suitable reducing agent, preferably sodium cyanoborohydride, to give the isomeric compounds of Formulas IC1, IC2, IC3 and IC4.

in turn, treated with a suitable diol in the presence of a suitable acid catalyst, for example, ethylene glycol in the presence of p-toluenesulfonic acid, to afford a ketal of Formula 26. The compound of Formula 26 is treated with a suitable reducing agent for reducing the cyano group to the amine to afford a compound of Formula 27. The cyano group is preferably reduced by catalytic hydrogenation, for example, over Raney nickel cata-

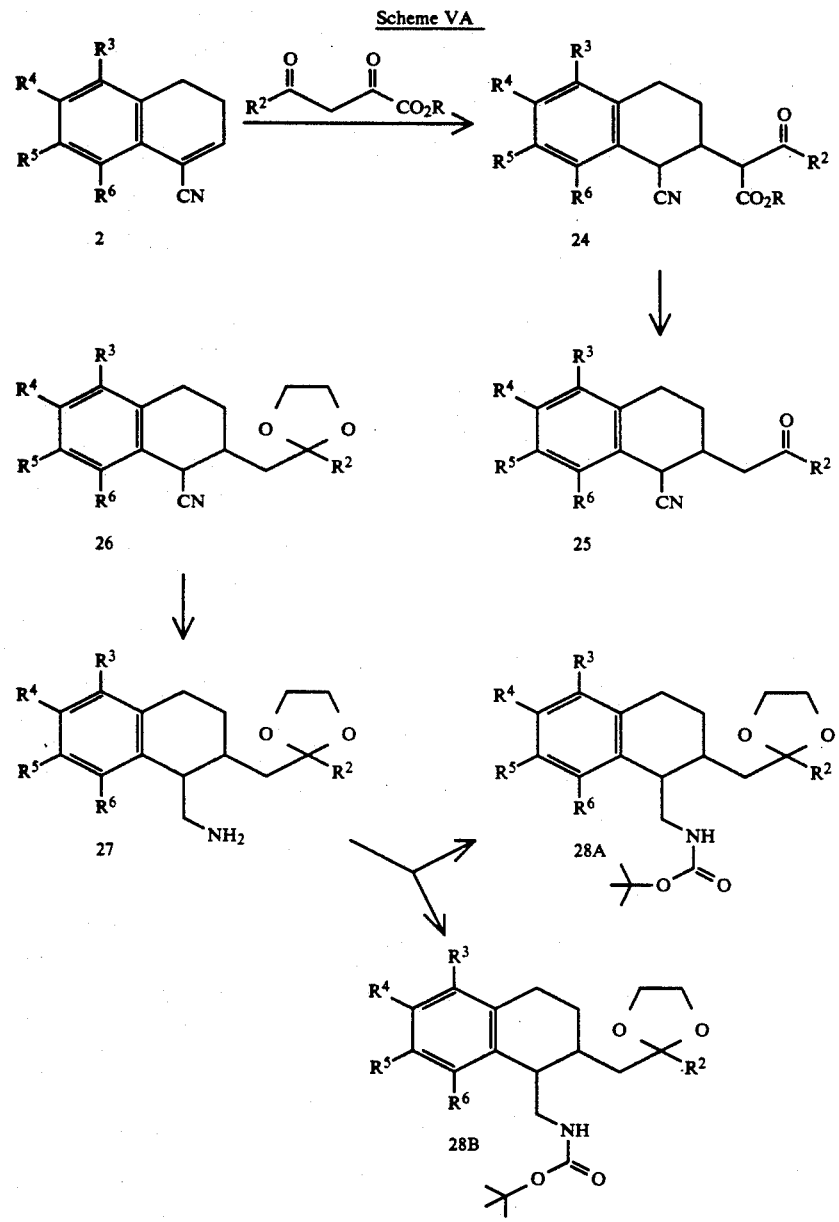

Scheme VA

According to reaction scheme VA, an unsaturated nitrile of Formula 2 is reacted with a β-keto ester to afford a compound of Formula 24. A compound of Formula 24 is then decarboxylated to afford a keto compound of Formula 25. The ketone of Formula 25 is, lyst. An amino compound of Formula 27 is then treated with a suitable reagent for forming separable diastereomeric carbamate derivatives of the amine, for example a compound of Formula 27 is treated with BOC-anhydride to afford the diastereomeric compounds of Formulas 28A (cis) and 28B (trans).

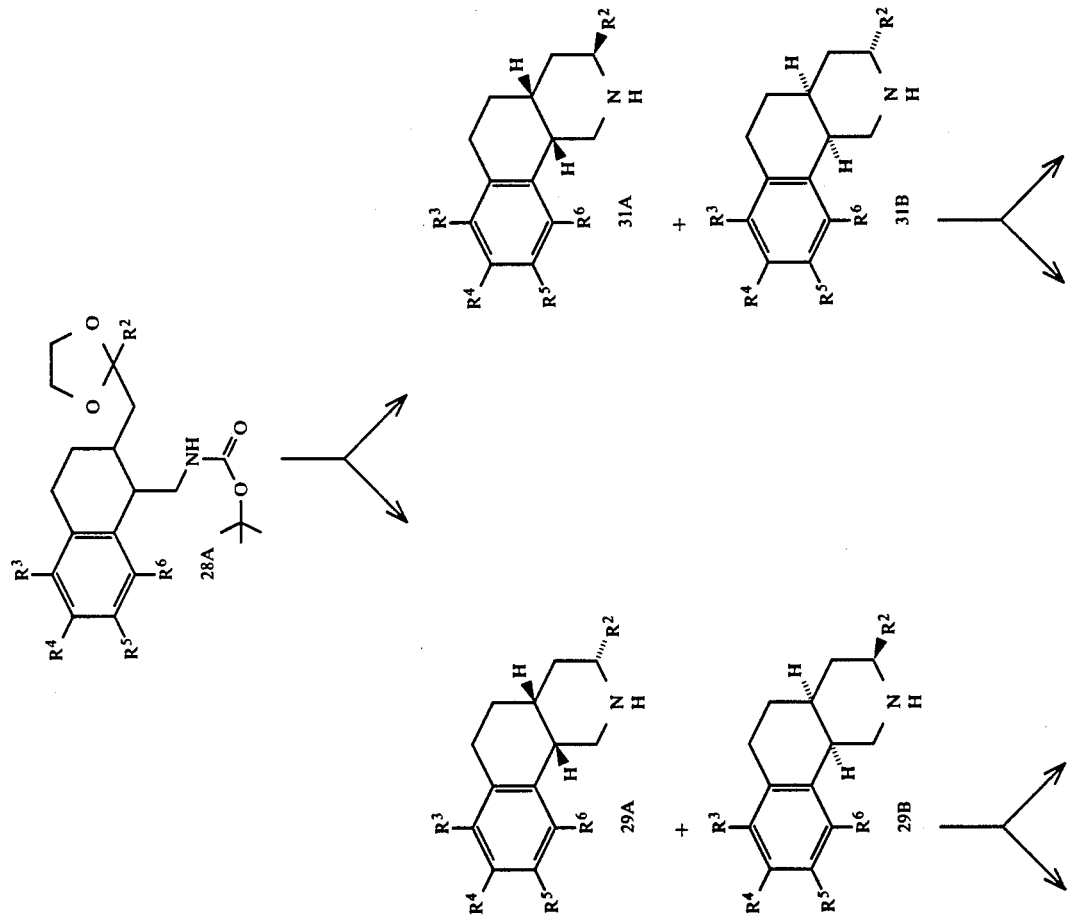

-continued
Scheme VB
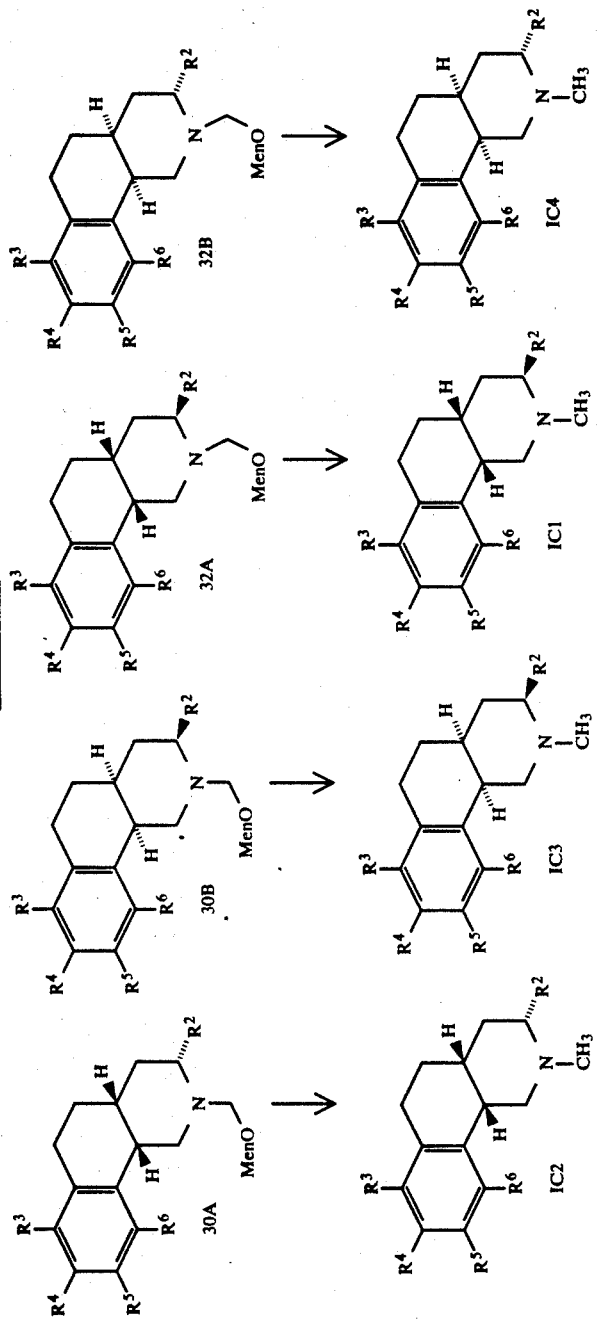

Scheme VB

According to reaction scheme VB, the cis diastereomer of a compound of Formula 28 (28A) is treated with a suitable acid, such as trifluoroacetic acid, for simultaneously cleaving the carbamate to afford the free amine and the ketal to form the ketone, which then condense intramolecularly to afford a cyclic imine compound which is, in turn, reduced, preferably with sodium cyanoborohydride, to afford the diastereomeric compounds of Formulas 29 (the cis-anti isomer) and 31 (the cis-syn isomer). The diastereomeric compounds of Formulas 29 and 31 are separated, for example, by chromatography. The diastereomeric compounds of Formula 29A and Formula 29B are then treated with a chloroformate derivative of an optically active alcohol, such as, for example menthyl chloroformate (as shown in reaction scheme VB) or alternately, the chloroformate derivative of fenchol, borneol, α-naphthylethanol, myrtanol or nopol, to afford the separable diastereomeric carbamates of Formulas 30A and 30B. The chloroformate derivatives are readily prepared by treating the optically active alcohol with phosgene using standard procedures. The carbamates of Formula 30 are separated and then treated with a suitable reducing agent, for example lithium aluminum hydride, to reduce the carbamate to the N-methyl derivative affording the enantiomeric compounds of Formulas IC2 and IC3. The diastereomeric compounds of Formula 31 are treated in an identical manner to the compounds of Formula 29 to afford the enantiomeric compounds of Formulas IC1 and IC4.

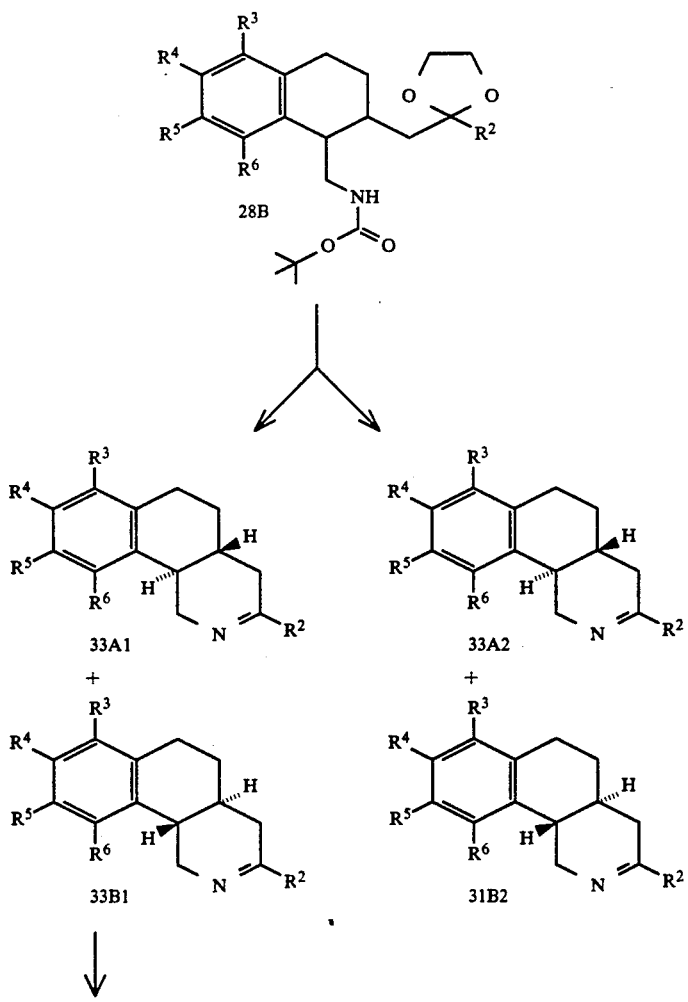

Scheme VC

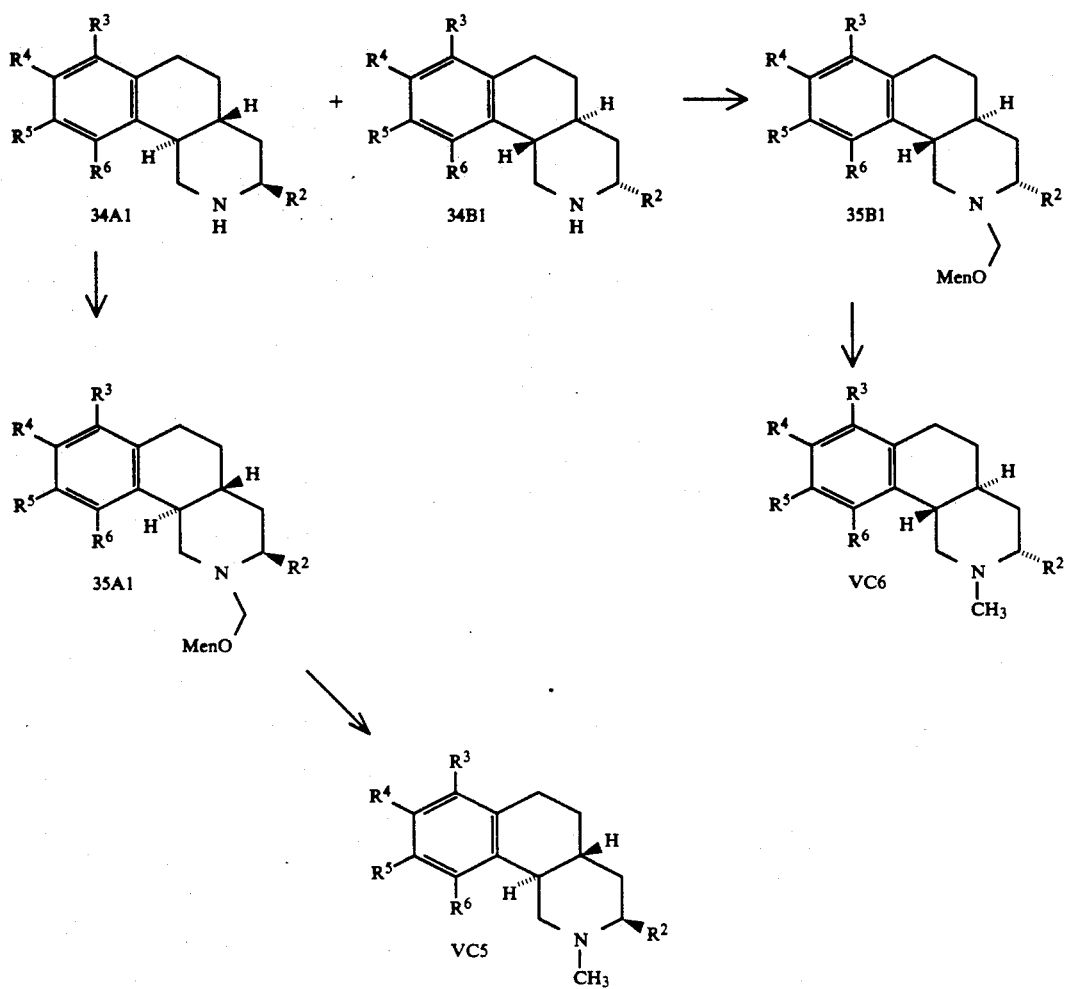

Scheme VC

According to reaction scheme VC, the trans diastereomer of a compound of Formula 28 (28B) is treated with a suitable acid, such as trifluoroacetic acid, for simultaneously cleaving the carbamate to afford the free amine and the ketal to form the ketone, which then condense intramolecularly to afford a cyclic imine compound of Formula 33. The imine is, in turn, reduced, preferably with sodium cyanoborohydride, to afford the enantiomeric compounds of Formula 34 (the trans-syn isomer). The compounds of Formula 34 are resolved as described in reaction scheme VB by treatment with a chloroformate derivative of an optically active alcohol to afford the separable diastereomeric carbamates of Formulas 35A1 and 35B1. The carbamates of Formula 30 are separated and then treated with a suitable reducing agent, for example, lithium aluminum hydride, to reduce the carbamate to the N-methyl derivative affording the enantiomeric compounds of Formulas IC5 and IC6.

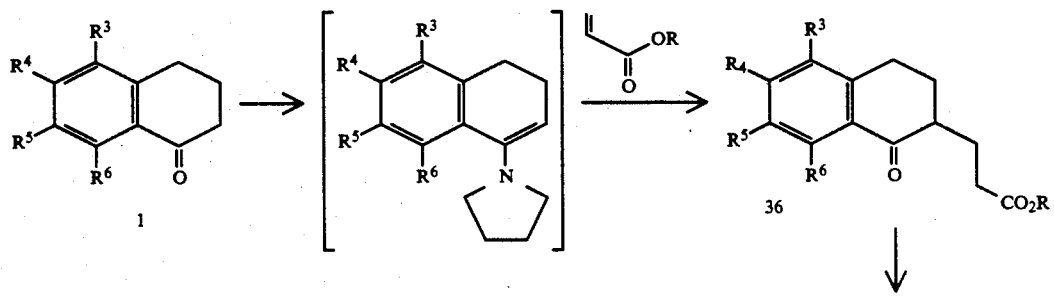

-continued
Scheme VI

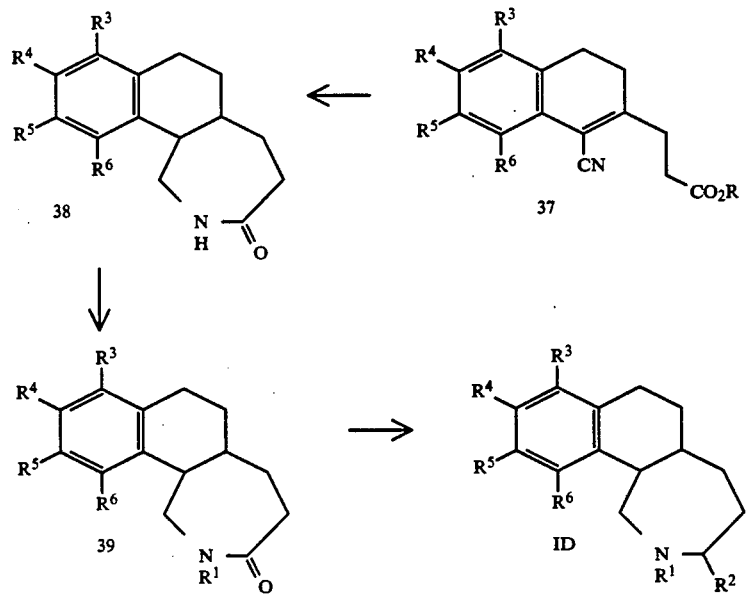

Scheme VI

According to reaction scheme VI, teralones of Formula 1 are condensed with an acrylate ester, for example, ethyl acrylate, in the presence of pyrrolidine and a suitable acid, such as p-toluenesulfonic acid, to afford the compounds of Formula 36. The compounds of Formula 36 are converted to the compounds of Formula 37 by treatment with a suitable cyano derivative, for example, diethylcyanophosphonate, followed by treatment with a suitable acid, for example p-toluenesulfonic acid in refluxing toluene. The compounds of Formula 37 are cyclized to the lactams of Formula 38 by reduction of the cyano group to the corresponding aminomethyl group which spontaneously condenses with the ester group to form the lactam. The lactams of Formula 38 are converted to the compounds of Formula VI' as described in reaction scheme IV for the conversion of the compounds of Formula 22 to the compounds of Formula ID.

Scheme VII

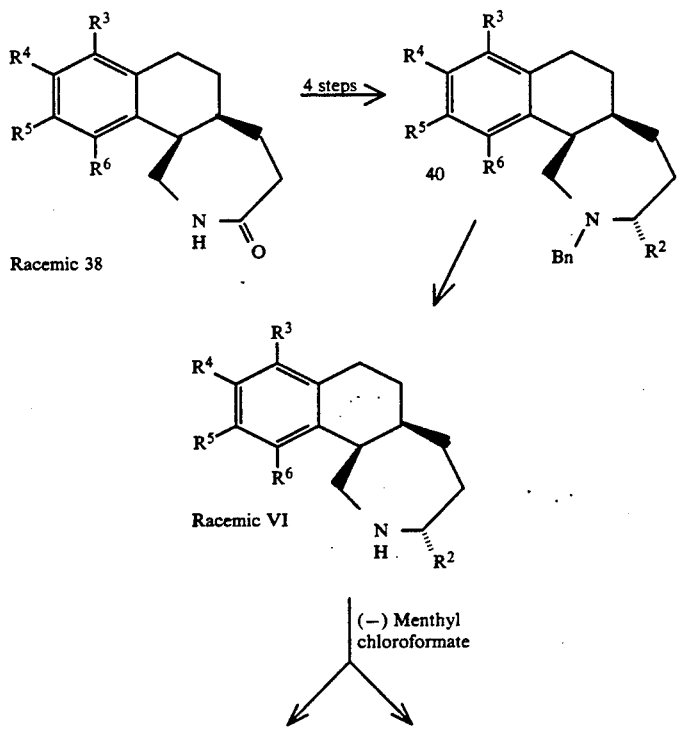

Scheme VII

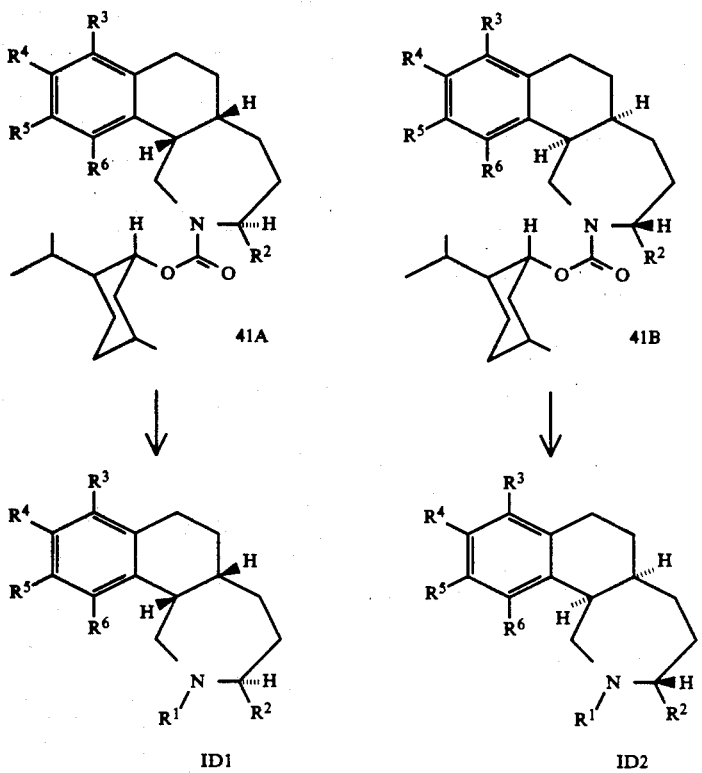

Scheme VII

According to reaction scheme VII, a racemic compound of Formula 38 is treated with a suitable base, such as, for example potassium t-butoxide, and benzyl bromide to give the N-protected compound, which is, in turn, treated with a Grignard reagent, as described previously in reaction scheme IV for the conversion of the compounds of Formula 22 to the compound of Formula IV, to afford a racemic compound of Formula VI. A racemic compound of Formula VI is then condensed with (−) menthyl chloroformate to afford the diastereomeric carbamates of Formulas 40A and 40B. The compounds of Formula 29 and 30 are treated with a suitable reducing agent, such as, for example, lithium aluminum hydride, to afford the optically active compounds of Formulas ID1 and ID2.

By "pharmaceutically acceptable" it is meant those salts which are, within the scope of sound medical judgement, suitable for use in contact with the tissues of humans and lower animals without undue toxicity, irritation, allergic response and the like, and are commensurate with a reasonable benefit/risk ratio, effective for their intended use in the treatment of depression and related mood and effective disorders. The salts can be prepared in situ during the final isolation and purification of the compounds of Formula (I), or separately by reacting the free base function with a suitable acid or cation. Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts and the like. Representative alkali or alkaline earth metal salts include sodium, calcium, potassium, magnesium salts and the like.

The term "affective disorder" as used herein refers to disorders that are characterized by changes in mood as the primary clinical manifestation, cf, R. J. Baldessarini in *Goodman and Gilman's The Pharmacological Basis of Therapeutics*, A. G. Gilman, L. S. Goodman, T. W. Rall and F. Murad, Eds., Macmillan, New York, 1985, pp 412–432.

The term "biogenic amine uptake" as used herein refers to the selective, systems for attenuating and terminating the affects of the biogenic amines by actively transporting them into nerve terminals and subsequently, into storage granules.

The term "depression" as used herein refers to "major depression" as defined in the seventh edition of Goodman and Gilman's "The Pharmacological Basis of Therapeutics". Major depression is distinguishable from normal grief, sadness and disappointment and is characterized by feelings of intense sadness and despair, mental showing and loss of concentration, pessimistic worry, agitation and self-deprecation. Physical changes also occur, including insomnia, anorexia and weight loss, decreased energy and libido, and disruption of hormonal circadian rhythms.

Protocol for Uptake Inhibition Assays

The compounds of formula (I) inhibit the uptake of biogenic amine neurotransmitters into nerve terminals and, therefore, are useful in treatment of affective disorders. Such diseases include major depression and the dipolar disorder, manic-depressive illness. The compounds of this invention may also be useful in the treatment of depression associated with other forms of mental illness, such as, for example, psychosis and dementia.

For the purpose of identifying compounds as biogenic amine uptake inhibitors capable of interacting with the uptake carrier, ligand-carrier binding assays were carried out as an initial sceen. The ability of the compounds of the invention to interact with biogenic amine uptake carriers and to inhibit the neuronal uptake of biogenic amines can be demonstrated in vitro using the following protocols.

Synaptosomal Preparation

Male Sprague-Dawley derived rats, weighing about 180-250 g each (purchased from Sasco Animal Laboratories, Oregon, Wis.) were sacrificed by decapitation. The brains were immediately removed, placed on a chilled glass plate and dissected according to a modification of the method of Glowinski and Iversen (J. Glowinski and L. L. Iversen, *J Neurochem*, 1966, 13: 655-669). First, the rhombencephalon was separated by a transverse section and discarded. The rest of the brain was divided into two portions by making another transverse section at the level of the optic chiasma. The hypothalamus, which was used for norepinephrine uptake studies, was removed from the posterior part by using the anterior commissure as the horizontal reference point and a line between the posterior hypothalamus and mammillary bodies as the caudal limit. The striatum, which was used for dopamine uptake studies, was also dissected from the posterior portion using the external wall of the lateral ventricle as the internal limit and the corpus collosum as the external limit. The frontal parts of the striatum were removed from the anterior portion of the cerebrum and combined with the striatal tissue from the posterior segment. The cortex, which was used for serotonin uptake studies, was composed of the rest of the anterior portion of the cerebrum and the cortical surfaces removed from the posterior segment. The hypothalamus and the striatum each weighed about 100 mg or slightly less, whereas the cortex weighed up to 800 mg. The tissues were placed in a cold Potter-Elvehjem glass homogenizer with 5 (cortex) or 10 (hypothalamus) or 20 (striatum) volumes of ice-cold 0.32M sucrose, pH 7, and homogenized by hand. The homogenate was centrifuged (on a Multifuge ®, American Scientific Products) at 2500 rpm for 10 minutes in a refrigerated room (~4° C.). The supernatant fraction containing the synaptosomes was decanted, mixed thoroughly and kept on crushed ice for use in the uptake studies.

Uptake Studies

Uptake studies were conducted according to the method of Snyder and Coyle (S. H. Snyder and J. T. Coyle, *J Pharmacol Exp Ther*, 1969, 165: 78-86) with minor modifications. Usually a 0.1 mL aliquot of the synaptosomal preparation was incubated in a mixture of 0.75 mL of modified Krebs-Ringer buffer, 0.05 mL of the drug being tested, and 0.1 mL of a 1 $\mu$M solution of the labeled (tritiated) amine (final concentration 0.1 $\mu$M), for a total volume of 1 mL. The modified Krebs-Ringer bicarbonate buffer used in these studies contained 118 mM sodium chloride, 4 mM potassium chloride, 1.3 mM calcium chloride, 1.12 mM potassium dihydrogen phosphate, 1.2 mM magnesium sulfate and 24 mM sodium bicarbonate, with the addition of 5 mM glucose, 0.15 mM disodium EDTA, 12.5 $\mu$M nialamide and 1 mM ascorbic acid. Uptake was initiated by the addition of the tritiated amine and the mixture was incubated at 37° C. in a Dubnoff Metabolic Shaking Incubator for 4 minutes. A preincubation period was not included since it had been reported that results were similar with and without preincubation of the synaptosomal preparation (G. Vosmer, et al. *Biochem Pharmacol*, 1980, 24: 2557-2562). Control incubations without the test drug were conducted at 37° C. to determine total uptake and at 0° C. (in a crushed ice bath) to correct for the diffusion of the tritiated amine into the synaptosomes and/or binding.

Filtration was used to terminate uptake and collect the synaptosomes (C. A. Csernansky, et al. *J Pharmacol Methods*, 1985, 13: 187-191). In the filtration technique, the incubation mixture was diluted with ice-cold 0.9% aqueous sodium chloride solution and filtered through GF/B glass microfiber filters (Whatman) under reduced pressure. The filters were subsequently washed four times with 5 mL of ice-cold 0.9% aqueous sodium chloride solution and transferred to glass scintillation vials. Soluene (500 mL) and HIONIC FLUOR (Packard) scintillation fluid (3.5 mL) were added, and the vials were placed in a mechanical shaker for approximately 1 hour. All the samples were cold- and dark-adapted and counted in a Tri-Carb ® (Packard) Model 460 Liquid Scintillation Spectrometer. Corrections were automatically made for quenching by the external standard method and for luminescence. All the results were based on total radioactivity since it has been shown and is generally accepted that at least 85% of the synaptosomal content of the tritiated amines was unmetabolized.

Uptake was calculated by subtracting the dpm (disintegrations per minute) in the 0° C. controls from the dpm in all other samples. Percent inhibition with the test drug was determined by comparison with the controls incubated at 37° C. $IC_{50}$ values, expressed as the molar concentration of drug that inhibited uptake of the tritiated amine by 50%, are shown in Table 2.

As used herein, the term "pharmaceutically acceptable carrier" means a non-toxic, inert solid, semi-solid or liquid filler, diluent, encapsulating material or formulation auxillary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations. Wetting agents, emulsifiers and lubricants such as sodium lauryl sulfate and magnesium stearate, as well as coloring agents, releasing agents, coating agents, sweetening, flavoring and perfuming agents, and preservatives can also be present in the composition, according to the judgement of the formulator.

The compounds of the present invention may be administered alone or in combination or in concurrent therapy with other agents.

The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a host in single or in divided doses can be in amounts, for example, from 0.01 to 25 mg/kg body weight or more usually from 0.1 to 15 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in multiple doses or in a single dose of from 10 mg to 1000 mg.

This invention also provides pharmaceutical compositions in unit dosage forms, comprising a therapeutically effective amount of a compound (or compounds) of this invention in combination with a conventional pharmaceutical carrier.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of a drug from subcutaneous or intramuscular injection. The most common way to accomplish this is to inject a suspension of crystalline or amorphous material with poor water solubility. The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. Depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsifying and suspending agents; sweetening, flavoring and perfuming agents.

If desired, the compounds of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use.

The active compounds can also be in micro-encapsulated form with one or more excipients as noted above.

Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

The foregoing may be better understood from the following examples, which are presented for the purpose of illustration and not intended to limit the scope of the inventive concept.

EXAMPLE 1 cis/trans
2,3,3a,4,5,9b-Hexahydro-7-methoxy-3-phenylmethyl-
1H-benz[e]isoindole hydrochloride

Step 1: 2-Phenylmethyl-1,3-dithiane

To a solution of 33.9 g (280 mmol) of phenylacetaldehyde and 35.6 g (330 mmol) of 1,3-propanedithiol in 300 mL of methylene chloride at 0° C., was added, dropwise over a period of 30 minutes, 10 mL of boron trifluoride etherate. The reaction mixture was allowed to warm to ambient temperature and stirred for 3 h at ambient temperature. The reaction mixture was made basic by the addition of 180 mL of 5% aqueous potassium hydroxide solution and the resultant mixture was stirred for 0.5 h. The layers were separated and the aqueous layer was extracted with methylene chloride. The combined organic extract was washed with 1N aqueous sodium hydroxide solution and brine, dried over anhydrous magnesium sulfate, filtered and the filtrate was distilled to afford 53.62 g (91% yield) of the title compound, b.p. 150° C. (2 mm Hg); $^1$H NMR (CDCl$_3$) δ1.75–1.95 (1H, m), 2.05–2.17 (1H, m), 2.75–2.91 (4H, m), 3.03 (2H, d, J=9 Hz), 4.25 (1H, t, J=9 Hz), 7.17–7.38 (5H, m).

Step 2: 1-Cyano-6-methoxy-3,4-dihydronaphthalene

Trimethylsilylcyanide (50.0 g, 510 mmol) was added to a suspension of 75.0 g (430 mmol) of 6-methoxy-α-tetralone (commercially available from Aldrich Chemical Company) in 75 mL of anhydrous tetrahydrofuran (THF) at ambient temperature. Lithium cyanide (100 mL of a 0.5M solution in N,N-dimethylformamide (DMF) was added to the resultant mixture in one portion. The reaction mixture was stirred at ambient temperature for 1.5 h and then the THF was removed under reduced pressure. The concentrate was partitioned between diethyl ether and water (5:1 v/v). The aqueous layer was extracted with diethyl ether and the combined organic extract was washed with brine, dried over anhydrous magnesium sulfate, filtered and concentrated under reduced pressure. The residue was dissolved in 400 mL of anhydrous toluene, containing 15 g of p-toluenesulfonic acid, previously refluxed in order to remove residual water by azeotropic distillation. The mixture was heated at reflux (with a Dean Stark trap) for 1 h. The resultant solution was cooled to ambient temperature and washed with cold 1N aqueous sodium hydroxide solution. The organic layer was separated, dried over anhydrous magnesium sulfate, filtered and concentrated in vacuo. The residue was purified on silica gel eluted with 10% ethyl acetate in hexane to afford 48.09 g (60% yield) of the title compound. The physical properties of the product were identical to the properties reported for this compound by F. Z. Basha, et al. in *J. Organic Chemistry*, 50: 4160-2 (1985).

Step 3: 1-Cyano-2-[1-(1,3-dithiane)-2-phenylethyl]-6-methoxy-1,2,3,4-tetrahydronaphthalene To a solution of 14.0 g (66.7 mmol) of 2-phenylmethyl-1,3-dithiane (from Step 1) in 250 mL of anhydrous THF at −20° C. under a nitrogen atmosphere was added 49 mL (73.4 mmol) of a 1.5M solution of n-butyl lithium in hexane. The reaction mixture was stirred for approximately 1 h at −20° C. and then was cooled to −78° C. A solution of 12 g (63.5 mmol) of 1-cyano-6-methoxy-3,4-dihydronaphthalene, from Step 2, in 250 mL of THF was added dropwise to the solution of 2-benzyl-2-lithio-1,3-dithiane, and immediately the clear colorless solution become a reddish purple color. The reaction mixture was warmed to 0° C., was stirred at 0° C. for 1 h, and then was cooled to −78° C. and the reaction was quenched by the addition of 100 mL of saturated aqueous ammonium chloride solution. Methylene chloride was added to the reaction mixture and the layers were separated. The organic layer was washed with brine, dried over anhydrous magnesium sulfate, filtered and concentrated in vacuo. The resultant oil was triturated with diethyl ether/hexane to afford 14.01 g (57% yield) of the cis isomer of the title compound. The material which was soluble in the diethyl ether/hexane was purified on silica gel eluted with 25% ethyl acetate in hexane to afford 9 g (36.6% yield) of a cis/trans mixture of the title compound; $^1$H NMR (CDCl$_3$) of cis isomer δ1.72–1.97 (2H, m), 2.02–2.18 (1H, m), 2.45–2.97 (7H, m), 3.03–3.15 (1H, m) 3.1 , 3.72 (2H, dd J=15 Hz), 3.78 (3H, s), 4.45 (1H, dd, J=4.6, 1.5 Hz), 6.69 (1H, d, J=3 Hz), 6.78 (1H, dd, J=9 Hz, 3 Hz), 7.21 (1H, d, J=9 Hz), 7.25–7.45 (5H, m).

Step 4: 1-Cyano-6-methoxy-2-[1-(1,3-dioxolane)-2-phenylethyl]-1,2,3,4-tetrahydronaphthalene A mixture of 6.04 g (15.3 mmol) of the cis isomer of 1-cyano-2-[1-(1,3-dithiane)-2-phenylethyl]-6-methoxy-1,2,3,4-tetrahydronaphthalene from Step 3, 40 mL of ethylene glycol, 40 mL of THF and 17.0 g (45.8 mmol) of mercury dichloride was stirred with a mechanical stirrer at 60° C. overnight. The mixture was filtered through Celite filter aid and the filter cake was washed with methylene chloride. The THF was evaporated and the residue was partitioned between water and methylene chloride (1:5, v/v). The aqueous layer was extracted twice with methylene chloride and discarded. The combined organic layers were washed twice with water and once with brine, dried over anhydrous magnesium sulfate, filtered and concentrated. The residue was absorbed onto silica gel and purified by flash chromatography on silica gel eluted with 25% ethyl acetate in hexane to afford 3.69 g (69% yield) of the title compound; MS DCl—NH3 M/Z: 350 (M+H)$^+$, 367 (M+NH4)$^+$; $^1$H NMR (CDCl$_3$) δ2.0–2.18 (3H, m), 2.68–2.83 (1H, m), 2.9–3.0 (1H, m), 2.95, 3.1 (2H, dd, J=15 Hz), 3.62–3.7 (1H, m), 3.72 (3H, s), 3.84–3.92 (1H, m), 4.02–4.13 (3H, m), 6.62 (1H, d, J=3.0 Hz), 6.72 (1H, dd, J=9.0 Hz, 3.0 Hz), 7.1 (1H, d, J=9.0 Hz), 7.2–7.3 (5H, m).

Step 5: 1-Aminomethyl-6-methoxy-2-[1-(1,3-dioxolane)-2-phenylethyl]-1,2,3,4-tetrahydronaphthalene 1-Cyano-6-methoxy-2-[1-(1,3-dioxolane)-2-phenylethyl]-1,2,3,4-tetrahydronaphthalene (3.7 g, 10.6 mmol) from Step 4 was dissolved in 135 mL of methanol and 15 mL of condensed ammonia and the resultant solution was treated for 24 h at ambient temperature with hydrogen gas (4 atmospheres) in the presence of 7.4 g of Raney nickel #28 catalyst. The hydrogenation mixture was filtered and concentrated in vacuo. The residue was absorbed onto silica gel and purified on silica gel eluted with ethyl acetate:formic acid:water (8:1:1, v/v/v) to give the formic acid salt of the desired product which was dissolved in water. The aqueous solution was made basic by the addition of sodium hydroxide and then extracted with methylene chloride. The organic phase was concentrated under reduced pressure to afford 3.15 g (84% yield) of the title compound: MS DCl—NH$_3$ M/Z: 354 (M+H)$^+$, 371 (M+NH$_4$)$^+$; $^1$H NMR (CDCl$_3$) δ1.53–1.7 (1H, m), 2.07–2.2 (2H, m), 2.52–2.87 (5H, m), 2.86, 2.97 (2H, dd, J=15 Hz), 3.30–3.50 (2H, m), 3.62–3.72 (1H, m), 3.75 (3H, s), 3.84–3.92 (1H, m), 6.67 (1H, d, J=3.0 Hz), 6.74 (1H, dd, J=9.0 Hz, 3.0 Hz), 7.17 (1H, d, J=9.0 Hz), 7.2–7.3 (5H, m).

Alternately, the title compound was purified by conversion to the corresponding hydrochloride salt by treatment of the residue from the hydrogenation reaction with methanol saturated with anhydrous hydrogen chloride. In one preparation, the hydrochloride salt of the title compound was recrystallized from diethyl ether/ethyl alcohol to afford the hydrochloride salt of the title compound in 78% yield.

Step 6: cis/trans 2,3,3a,4,5,9b-Hexahydro-7-methoxy-3-phenylmethyl-1H-benz[e]isoindole hydrochloride A solution of 3.15 g (8.21 mmol) of 1-aminomethyl-2-[1-(1,3-dioxolane)-2-phenylethyl[-6-methoxy-1,2,3,4-tetrahydronaphthalene, from Step 5, in 120 mL of THF and 60 mL of 3N aqueous hydrochloric acid solution was stirred overnight at ambient temperature. The reaction mixture was evaporated to near dryness and the residual oil was dissolved in 200 mL of methanol. To the methanol solution was added a few crystals of bromocresol green indicator, followed by 7 g of sodium cyanoborohydride. After 15 minutes, the solvent was evaporated and the residue was partitioned between methylene chloride and water (4/1, v/v). The layers were separated and the aqueous layer was extracted twice with methylene chloride. The combined organic layers were concentrated and the concentrated solution adsorbed onto silica gel. The silica gel was loaded onto a silica gel column and elution with ethyl acetate:formic acid:water (18:1:1, v/v/v) to afford 2.50 g (94% yield) of the formic acid salt of title compound as a 7/3 cis/trans mixture at the ring juncture. The free amine was prepared by dissolving the formic acid salt in water, adding sodium hydroxide to make the solution basic and extracting the basic solution with methylene chloride. The methylene chloride was removed under reduced pressure and the residue was dissolved in diethyl ether saturated with anhydrous hydrogen chloride. The desired hydrochloride salt was collected by filtration, m.p. 238–239; MS DCl—NH$_3$ M/Z: 294 (M+H)$^+$; $^1$H NMR (CDCl$_3$) mixture of cis: δ1.46–1.62 (1H, m), 1.83–1.95 (1H, m), 2.16–2.28 (1H, m), 2.63–2.97 (5H, m), 3.27–3.47 (2H, m), 3.59–3.69 (1H, m), 3.77 (3H, s), 6.67 (1H, d, J=3.0 Hz), 6.7 (1H, dd, J=9.0 Hz, 3.0 Hz), 6.97 (1H, d, J=9.0 Hz), 7.17–7.36 (5H, m). trans: δ1.42–1.62 (2H, m), 1.8–1.9 (2H, m), 2.63–2.97 (5H, m), 3.14–3.25 (1H, m), 3.47–3.57 (1H, m), 3.77 (3H, s), 6.69 (1H, d, J=3.0 Hz), 6.87 (1H, d, J=9.0 Hz), 7.0 (1H, dd, J=9.0 Hz, 3.0 Hz), 7.17–7.36 (5H, m). Analysis calculated for C$_{20}$H$_{24}$ClNO+0.5H$_2$O: C, 70.89; H, 7.44; N, 4.13. Found: C, 70.43; H, 7.19; N, 4.08.

EXAMPLE 2 cis-2,3,3a,4,5,9b-Hexahydro-7-methoxy-2-methyl-3-phenylmethyl-1H-benz[e]isoindole methanesulfonic acid salt A solution of 1.18 g (4.0 mmol) of 2,3,3a,4,5,9b-hexahydro-7-methoxy-3-phenylmethyl-1H-benz[e]isoindole (the product of Example 1) and 2.07 mL of formalin (37% aqueous formaldehyde solution) in 100 mL of methanol was hydrogenated at ambient temperature with 4 atmospheres of hydrogen for 24 h in the presence of 0.24 g of 20% palladium on carbon. The hydrogenation mixture was filtered and the filtrate was concentrated in vacuo. The residue was adsorbed on silica gel and chromatographed on silica gel eluted with diethyl ether:hexane presaturated with ammonia (7:2, v/v) to give 690 mg (56% yield) of the amine product which was converted to the title compound by treatment with 1.1 equivalents of methanesulfonic acid in acetone/diethyl ether solution, m.p. 149.5°–150.3° C.; MS DCl—NH$_3$ M/Z: 308 (M+H)$^+$; $^1$H NMR of the methanesulfonic acid salt (CDCl$_3$) δ1.8–2.1 (2H, m), 2.45–2.57 (1H, m), 2.6–2.78 (2H, m), 2.85–2.97 (1H, m), 2.79 (3H, s), 2.83 (3H, d, J=6 Hz), 3.2–3.4 (2H, m), 3.5–3.7 (2H, m), 3.77 (3H, s), 3.9–4.02 (1H, m), 6.65 (1H, d, J=3 Hz), 6.7 (1H, dd, J=9 Hz, 3 Hz), 6.88 (1H, d, J=9 Hz), 7.28–7.43 (5H, m). Analysis calculated for C$_{22}$H$_{29}$NO$_4$S: C, 65.48; H, 7.24; N, 3.47. Found: C, 65.53; H, 7.20; N, 3.42.

EXAMPLE 3 cis-2-Ethyl-2,3,3a,4,5,9b-hexahydro-7-methoxy-3-phenylmethyl-1H-benz[e]isoindole methanesulfonate salt 2,3,3a,4,5,9b-Hexahydro-7-methoxy-2-methyl-3-phenylmethyl-1H-benz[e]isoindole (0.97 g, 3.2 mmol), the product of Example 1, was dissolved in 10 mL of pyridine and approximately 10 mL of acetic anhydride was added to the resultant solution. The reaction mixture was stirred at ambient temperature for 0.5 h and then most of the pyridine was removed in vacuo. The concentrate was partitioned between ethyl acetate and dilute aqueous hydrochloric acid solution (4:1 v/v) and the layers were separated. The aqueous layer was extracted twice with ethyl acetate and the combined organic layers were washed with dilute aqueous sodium hydroxide solution, dried over anhydrous magnesium sulfate, filtered and concentrated in vacuo. The residue was dissolved in 20 mL of anhydrous THF and borane-THF complex (15 mL of a 1.0M solution in THF, 15 mmol) was added to the resultant solution. The reaction mixture was heated at reflux for 1 h. The THF was removed in vacuo and the residue was dissolved in 20 mL of methanol saturated with anhydrous hydrogen chloride. The solution was heated at reflux overnight and the solvent was removed in vacuo. The residue was partitioned between methylene chloride and 15% aqueous potassium hydroxide solution (4:1 v/v) and the layers were separated. The aqueous layer was extracted with two portions of methylene chloride and the combined organic layers were dried over anhydrous magnesium sulfate, filtered and concentrated in vacuo. The residue was purified on silica gel eluted with a 2:1 mixture of hexanes and diethyl ether saturated with ammonia to give 840 mg (~85% yield) of the product as the free amine. The amine product was dissolved in a solution of methanesulfonic acid in diethyl ether to give the title compound, m.p. 166.0°–167.1° C.; MS DCl—NH$_3$ M/Z: 322 (M+H)$^+$. Analysis calculated for C$_{23}$H$_{31}$NO$_4$S: C, 66.16; H, 7.48; N, 3.35. Found: C, 65.79; H, 7.44; N, 3.38.

EXAMPLE 4 cis-2,3,3a,4,5,9b-Hexahydro-7-methoxy-2-phenylethyl-3-phenylmethyl-1H-benz[e]isoindole methanesulfonic acid salt 2,3,3a,4,5,9b-Hexahydro-7-methoxy-2-methyl-3-phenylmethyl-1H-benz[e]isoindole (0.80 g, 2.73 mmol), the product of Example 1, was dissolved in 10 mL of methylene chloride and approximately 5 mL of pyridine was added to the resultant solution. The solution was cooled to 0° C. and approximately 2.5 mL of phenylacetyl chloride was added, dropwise, over a 3 minute period and the reaction mixture was stirred for 45 minutes at ambient temperature. Water (20 mL) was added to the reaction mixture to quench the reaction and the resultant mixture was stirred at ambient temperature for 0.5 h. the mixture was transferred to a separatory funnel and 1N aqueous hydrochloric acid solution and 4 mL of methylene chloride were added. The layers were separated and the aqueous layer was extracted with two portions of methylene chloride. The combined organic layers were washed with 1N aqueous hydrochloric acid solution and 1N dilute aqueous sodium hydroxide solution, dried over anhydrous magnesium sulfate, filtered and concentrated in vacuo. The residue was purified on silica gel eluted with hexane:ethyl acetate (5:2 v/v) to give the intermediate amide, 2,3,3a,4,5,9b-hexahydro-7-methoxy-2-phenylmethylcarbonyl-3-phenylmethyl-1H-benz[e]isoindole, which was dissolved in 10 mL of anhydrous THF. Borane (4 mL of a 1.0M solution in THF, 4 mmol) was added to the solution of the amide and the reaction mixture was heated at reflux for 1 h. The solvent was removed in vacuo and the residue was dissolved in methanol. Methanol saturated with anhydrous hydrogen chloride was added and the solution was heated at reflux for 16 h. The methanol was removed under reduced pressure and the residue was partitioned between 1N aqueous sodium hydroxide solution and methylene chloride (1:4, v/v). The aqueous layer was extracted with two portions of methylene chloride and the combined organic layers were dried over anhydrous magnesium sulfate and filtered. Silica gel was suspended in the filtrate and the solvent was evaporated from the suspension to give a powder which was loaded onto a silica gel column. The column was eluted with a 5:1 mixture of hexane and diethyl ether saturated with ammonia to give 530 mg (49% yield) of the free amine product. The methanesulfonate salt (the title compound) was formed by dissolving the free amine product in a diethyl ether solution of methanesulfonic acid, m.p. 179°–180° C.; MS DCl—NH$_3$ M/Z: 398 (M+H)$^+$; $^1$H NMR of methanesulfonic acid salt (CDCl$_3$) δ1.94–2.1 (2H, m), 2.4–2.77 (2H, m), 2.83 (3H, s), 2.83–3.1 (3H, m), 3.2–3.55 (6H, m), 3.7–3.8 (1H, m), 3.78 (3H, s), 3.83, 3.93 (1H, dd, J=15 Hz, 9 Hz), 6.64 (1H, d, J=3 Hz), 6.69 (1H, dd, J=3 Hz, J=9 Hz), 6.89 (1H, d, J=9 Hz), 7.07–7.42 (10H, m). Analysis calculated for C$_{29}$H$_{35}$NO$_4$S: C, 70.56; H, 7.15; N, 2.84. Found: C, 70.19; H, 7.19; N, 2.80.

EXAMPLE 5 cis-2,3,3a,4,5,9b-Hexahydro-7-methoxy-2-(3-chlorophenyl)ethyl-3-phenylmethyl-1H-benz[e]isoindole methanesulfonic acid salt 2,3,3a,4,5,9b-Hexahydro-7-methoxy-2-methyl-3-phenylmethyl-1H-benz[e]isoindole (0.50 g, 1.7 mmol), the product of Example 1, 1-hydroxybenzotriazole (0.276 g, 2.04 mmol), and 3-chlorophenylacetic acid (0.35 g, 2.04 mmol), commercially available from Aldrich Chemical Company, were dissolved in 5 mL of dry THF under a nitrogen atmosphere. Dicyclohexylcarbodiimide (0.422 g, 2.04 mmol) was added dropwise to the resultant solution. The reaction mixture was stirred at ambient temperature under a nitrogen atmosphere for 48 h. The reaction mixture was then filtered and the filtrate was concentrated in vacuo. The solid residue was dissolved in ethyl acetate and the ethyl acetate solution was washed with 1N aqueous hydrochloric acid solution and 1N aqueous sodium hydroxide solution, dried over anhydrous magnesium sulfate, filtered and concentrated in vacuo. The residue was dissolved in 20 mL of anhydrous THF and borane (3.5 mL of a 1.0M solution in THF, 3.5 mmol) was added to the resultant solution. The reaction mixture was heated at reflux under a nitrogen atmosphere for 2 h. Methanol saturated with anhydrous hydrogen chloride was added and the reaction mixture was heated at reflux for 3 h and then stirred at ambient temperature overnight. The solvents were evaporated in vacuo and the residue was made basic with 1N aqueous sodium hydroxide solution. The aqueous solution was extracted with three portions of methylene chloride and the combined methylene chloride layers were dried over anhydrous magnesium chloride, filtered and concentrated in vacuo to afford ~310 mg (42% yield) of the free base. The residue was dissolved in an diethyl ether solution of methanesulfonic acid and the solution was concentrated to give the title compound, m.p. 195°–196° C.; MS DCl—NH$_3$ M/Z: 432 (M+H)$^+$; $^1$H NMR of methanesulfonic acid salt (CDCl$_3$) δ1.92–2.1 (2H, m), 2.45–2.75 (2H, m), 2.82 (3H, s), 2.82–3.04 (3H, m), 3.07–3.57 (6H, m), 3.67–3.96 (2H, m), 3.74 (3H, s), 6.63 (1H, d, J=3 Hz), 6.68 (1H, dd, J=3 Hz, 9 Hz), 6.92 (1H, d, J=9 Hz), 6.97–7.45 (9H, m). Analysis calculated for C$_{29}$H$_{34}$NClO$_4$S: C, 65.96; H, 6.49; N, 2.65. Found: C, 65.45; H, 6.50; N, 2.62.

EXAMPLE 6 trans-2,3,3a,4,5,9b-Hexahydro-7-methoxy-3-phenylmethyl-1H-benz[e]isoindole methanesulfonic acid salt Step 1:
1-Cyano-6-methoxy-2-phenylmethylcarbonyl-1,2,3,4-tetrahydronaphthalene A mixture of 7.40 g (18.7 mmol) of 1-cyano-2-[1-(1,3-dithiane)-2-phenylethyl]-6-methoxy-1,2,3,4-tetrahydronaphthalene (the product of Step 3 of Example 1), 15.2 g (56 mmol) of mercuric chloride and 7.5 g (74.8 mmol) of calcium carbonate in 190 mL of 80% aqueous acetonitrile solution was heated at reflux temperature overnight while being stirred with a mechanical stirrer, and was then cooled in an ice/water bath. To the cooled reaction mixture was added approximately 50 mL of concentrated sodium sulfide (Na$_2$S) and the resultant mixture was stirred with a mechanical stirrer for 10 minutes at 0° C. The mixture was filtered through Celite filter aid and the filtrate was concentrated in vacuo. The residue was partitioned between water and methylene chloride (1:4, v/v) and the resultant emulsion was filtered through Celite filter aid. The layers of the filtrate were separated and the aqueous layer was extracted with three portions of methylene chloride. The organic layers were combined, dried over anhydrous magnesium sulfate, filtered and concentrated in vacuo. The residue was purified on silica gel eluted with 3:1 hexane:ethyl acetate, followed by 2:1 hexane:ethyl acetate to give 4.29 g (75% yield) of the title compound, m.p. 139°-142° C.; MS DCl—NH$_3$ M/Z: 323 (M+NH$_4$)$^+$; $^1$H NMR cis isomer (CDCl$_3$) δ1.66-1.72 (1H, m), 2.11-2.22 (1H, m), 2.66-2.89 (2H, m), 3.16-3.26 (1H, m), 3.76 (3H, s), 3.90 (2H, d), 4.29 (1H, d), 6.60 (1H, d, J=3 Hz), 6.78 (1H, dd, J=3 Hz, 9 Hz), 7.21-7.40 (6H, m); $^1$H NMR trans isomer (CDCl$_3$) δ2.04-2.22 (1H, m), 2.26-2.38 (1H, m), 2.73-2.98 (3H, m), 3.75 (3H, s), 3.87 (2H, s), 4.09 (1H, d), 6.62 (1H, d, J=3 Hz), 6.77 (1H, dd, J=9 Hz, 3 Hz), 7.15 (1H, d, J=9 Hz), 7.19-7.39 (5H, m).

Step 2:
trans-2,3,3a,4,5,9b-Hexahydro-7-methoxy-3-phenylmethyl-1H-benz[e]isoindole methanesulfonic acid salt A solution of 3.05 g (10 mmol) of 1-cyano-6-methoxy-2-phenylmethylcarbonyl-1,2,3,4-tetrahydronaphthalene, from Step 1, in 200 mL of methanol containing 30 mL of triethylamine was hydrogenated (4 atmospheres of H$_2$), at ambient temperature, in the presence of 12.09 g of Raney nickel #28. The reaction mixture was filtered and the filtrate concentrated under reduced pressure. The residue was purified on silica gel eluted with ethyl acetate:formic acid:water (19:0.5:0.5 v/v/v) to give 2.61 g (90% yield) of the title compound; MS DCl—NH$_3$ M/Z: 294 (M+H)$^+$; $^1$H NMR of trans isomer (CDCl$_3$) δ1.33-1.52 (2H, m), 1.74-1.89 (1H, m), 1.92 (1H, bs), 2.72 (3H, s), 2.77-2.86 (2H, m), 2.98-3.10 (2H, m), 3.22-3.36 (1H, m), 3.39-3.48 (1H, m), 3.61-3.74 (1H, m), 3.77 (3H, s), 3.91-4.02 (1H, m), 6.64 (1H, d, J=3 Hz), 6.68 (1H, dd, J=3 Hz, 9 Hz), 6.82 (1H, d, J=9 Hz), 7.21-7.40 (5H, m), 8.93 (1H, bs), 9.51 (1H, bs). Analysis calculated for C$_{21}$H$_{25}$NO$_3$: C, 64.76; H, 3.60; N, 6.99. Found: C, 64.58; H, 3.54; N, 6.71.

EXAMPLE 7
trans-2,3,3a,4,5,9b-Hexahydro-7-methoxy-2-methyl-3-phenylmethyl-1H-benz[e]isoindole Following the procedures described in Example 2, substituting the product of Example 6 for the product of Example 1, the title compound was prepared, m.p. 168.5°-169° C.; MS DCl—NH$_3$ M/Z: 308 (M+H)$^+$; $^1$H NMR (CDCl$_3$) δ1.19-1.37 (1H, m), 1.45-1.58 (1H, m), 1.75-1.95 (1H, m), 1.95-2.17 (1H, m), 2.67 (3H, s), 2.79-3.00 (2H, m), 3.00-3.18 (2H, m), 3.18-3.47 (2H, m), 3.55-3.72 (1H, m), 3.77 (3H, s), 4.02-4.19 (1H, m), 6.65-6.72 (2H, m), 6.78 (1H, d), 7.29 (1H, t), 7.36 (2H, d), 7.47 (2H, d). Analysis calculated for C$_{21}$H$_{25}$NO: C, 65.48; H, 3.47; N, 7.18. Found: C, 65.54; H, 3.42; N, 7.30.

EXAMPLE 8
cis-anti-2,3,3a,4,5,9b-Hexahydro-7-methoxy-2-methyl-3-phenylmethyl-1H-benz[e]isoindole methanesulfonic acid salt Following the procedures described in Examples 1 and 2 on a larger scale, a minor product was obtained from the final purification which was identified as the title compound, m.p. 140.5°-141.0° C.; MS DCl—NH$_3$ M/Z: 308 (M+H)$^+$; $^1$H NMR (CDCl$_3$) δ1.30-1.43 (1H, m), 1.51-1.62 (1H, m), 2.53-2.61 (1H, m), 2.62-2.79 (2H, m), 2.73 and 2.76 (2 singlets in a 1:1 ratio, N—CH$_3$), 2.90 (3H, s), 3.04-3.15 (1H, m), 3.18-3.27 (1H, m), 3.42-3.50 (1H, m), 3.77 (3H, s), 3.88-3.98 (1H, m), 4.28-4.37 (1H, m), 6.62 (1H, d, J=3 Hz), 6.74 (1H, dd, J=3 Hz, 9 Hz), 7.08 (1H, d, J=9 Hz), 7.25-7.41 (5H, m). Analysis calculated for C$_{22}$H$_{29}$NO$_4$S: C, 65.48; H, 7.24; N, 3.47. Found: C, 65.27; H, 7.29; N, 3.46.

EXAMPLE 9
cis-2,3,3a,4,5,9b-Hexahydro-2-methyl-3-phenylmethyl-1H-benz[e]isoindole methanesulfonic acid salt Step 1: 1-Cyano-3,4-dihydronaphthalene Following the procedures described in Step 2 of Example 1, replacing 6-methoxy-α-tetralone with α-tetralone (commercially available from Aldrich Chemical Company), the title compound was prepared. The physical properties of the product were identical to those reported for this compound by F. Z. Basha, et al. in *J Organic Chemistry*, 50: 4160-2 (1985).

Step 2;
1-Cyano-2-[1-(1,3-dithiane)-2-phenylethyl]-1,2,3,4-tetrahydronaphthalene Following the procedures described in Step 3 of Example 1 for the conjugate addition of 2-benzyl-1,3-dithiane (14.2 g, 67 mmol), replacing 1-cyano-6-methoxy-3,4-dihydronaphthalene with 10 g (64.4 mmol) of 1-cyano-3,4-dihydronaphthalene (the product of Step 1 of this Example), the title compound was prepared in 77% yield (18.25 g); MS DCl—NH$_3$ M/Z: 366 (M+H)$^+$.

Step 3:
1-Cyano-2-[1-(1,3-dioxolane)-2-phenylethyl]-1,2,3,4-tetrahydronaphthalene Following the procedures of Step 4 of Example 1, replacing 1-cyano-2-[1-(1,3-dithiane)-2-phenylethyl]-6-methoxy-1,2,3,4-tetrahydronaphthalene with 1-cyano-2-[1-(1,3-dithiane)-2-phenylethyl]-1,2,3,4-tetrahydronaphthalene, from Step 2 above, the title compound was prepared; MS DCl—NH$_3$ M/Z: 320 (M+H)$^+$, 337 (M+NH$_4$)$^+$; $^1$H NMR (CDCl$_3$) δ2.07-2.25 (3H, m), 2.75-2.9 (1H, m), 2.94-3.1 (1H, m), 2.97-3.13 (2H, dd, J=15 Hz), 3.65-3.75 (1H, m), 3.87-3.98 (1H, m), 4.08-4.19 (3H, m), 7.1-7.3 (9H, m).

Step 4:
1-Aminomethyl-2-[1-(1,3-dioxolane)-2-phenylethyl]-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 1-cyano-2-[1-(1,3-dioxolane)-2-phenylethyl]-1,2,3,4-tetrahydronaphthalene, from Step 3 above, the title compound was prepared in 55% yield; MS DCl—NH$_3$ M/Z: 324 (M+H)$^+$; $^1$H NMR (CDCl$_3$) δ1.4-1.6 (1H, m), 2.02-2.2 (2H, m), 2.5-3.0 (5H, m), 2.84, 2.95 (2H, dd, J=15 Hz), 3.34-3.47 (2H, m), 3.6-3.7 (1H, m), 3.8-3.9 (1H, m), 7.05-7.34 (9H, m).

Step 5:
2,3,3a,4,5,9b-Hexahydro-3-phenylmethyl-1H-benz[e]isoindole

Following the procedures described in Step 6 of Example 1, replacing 1-cyano-2-[1-(1,3-dioxolane)-2-phenylethyl]-6-methoxy-1,2,3,4-tetrahydronaphthalene with 1-cyano-2-[1-(1,3-dioxolane)-2-phenylethyl]-1,2,3,4-tetrahydronaphthalene, from Step 4 above, the title compound was prepared in 77% yield (3.15 g) as a mixture of unseparable diastereomers; MS DCl—NH$_3$ M/Z: 263 (M+H)$^+$; $^1$H NMR of the free base (CDCl$_3$)

δ1.45–1.64 (2H, m), 1.85–1.95 (1H, m), 2.5–3.0 (5H, m), 3.3–3.65 (3H, m), 6.9–7.4 (9H, m).

Step 6:
cis-2,3,3a,4,5,9b-Hexahydro-2-methyl-3-phenylmethyl-1H-benz[e]isoindole methanesulfonic acid salt Following the procedures described in Example 2, replacing the product of Example 1 with the product of Step 5 of this Example, 2,3,3a,4,5,9b-hexahydro-2-methyl-3-phenylmethyl-1H-benz[e]isoindole was prepared as a mixtures of diastereomers which were separated by chromatography on silica gel eluted with 2:1 hexane: diethyl ether (saturated with ammonia) to give 780 mg of the title compound (the less polar diastereomer) in 28% yield, m.p. 168.2°–169.2° C.; MS DCl—NH$_3$ M/Z: (M+H)+278; $^1$H NMR of the free base (CDCl$_3$) δ1.57–1.75 (1H, m), 1.9–2.02 (1H, m), 2.1–2.24 (1H, m), 2.4 (3H, s), 2.5–2.65 (1H, m), 2.7–2.82 (2H, m), 2.87 (3H, m), 3.17–3.24 (1H, m), 3.29–3.37 (1H, m), 7.0–7.35 (9H, m). Analysis calculated for C$_{21}$H$_{27}$NO$_3$S: C, 67.53; H, 7.28; N, 3.75. Found: C, 67.51; H, 7.36; N, 3.72.

EXAMPLE 10 trans-2,3,3a,4,5,9b-Hexahydro-2-methyl-3-phenylmethyl-1H-benz[e]isoindole methanesulfonic acid salt From Step 6 of Example 9, the title compound (the more polar diastereomer) was obtained, after chromatography, in 56% yield; MS DCl—NH$_3$ M/Z: 278 (M+H)+; $^1$H NMR of methanesulfonic acid salt (CDCl$_3$) δ1.45–1.6 (1H, m), 1.75–1.86 (1H, m), 2.04–2.19 (1H, m), 2.3–2.4 (1H, bs), 2.77 (3H, d, J=6 Hz), 2.84 (3H, s), 3.86–3.97 (2H, m), 3.1–3.27 (3H, m), 3.4–3.57 (2H, m), 4.03–4.15 (1H, m), 6.85 (1H, d, J=9 Hz), 7.1–7.43 (8H, m). Analysis calculated for C$_{21}$H$_{27}$NO$_3$S: C, 67.53; H, 7.28; N, 3.75. Found: C, 67.27; H, 7.29; N, 3.72.

EXAMPLE 11 cis-2,3,3a,4,5,9b-Hexahydro-3-(3-methylphenyl)methyl-1H-benz[e]isoindole hydrochloride Step 1: 2-(3-Methylphenyl)methyl-1,3-dithiane Following the procedures described in Step 1 of Example 1, replacing phenylacetaldehyde with 3-methylphenylacetaldehyde the title compound was prepared; MS DCl—NH$_3$ M/Z: 221 (M+H)+.

Step 2:
1-Cyano-2-[1-(1,3-dithiane)-2-(3-methylphenyl)ethyl]-1,2,3,4-tetrahydronaphthalene Following the procedures described in Step 3 of Example 1, replacing 1-cyano-6-methoxy-3,4-dihydronaphthalene with 11.63 g (74.9 mmol) of 1-cyano-3,4-dihydronaphthalene (the product of Step 1 of Example 9) and 2-phenylmethyl-1,3-dithiane with 16.5 g (75 mmol) of 2-(3-methylphenyl)methyl-1,3-dithiane (the product of Step 1 of this Example), the title compound was prepared in 65% yield (18.5 g), m.p. 125°–128° C.; MS DCl—NH$_3$ M/Z: 380 (M+H)+; $^1$H NMR of cis isomer (CDCl$_3$) δ1.72–2.0 (2H, m), 2.07–2.2 (1H, m), 2.35 (3H, s), 2.48–3.02 (7H, m), 3.67, 3.72 (2H, dd, J=15 Hz), 3.12–3.27 (1H, m), 4.48 (1H, dd, J=4.6 Hz, 1.5 Hz), 7.04–7.33 (8H, m).

Step 3:
1-Cyano-2-[1-(1,3-dioxolane)-2-(3-methylphenyl)ethyl]-1,2,3,4-tetrahydronaphthalene Following the procedures of Step 4 of Example 1, replacing 1-cyano-2-[1-(1,3-dithiane)-2-phenylethyl]-6-methoxy-1,2,3,4-tetrahydronaphthalene with 16 g (42 mmol) of 1-cyano-2-[1-(1,3-dithiane)-2-(3-methylphenyl)ethyl]-1,2,3,4-tetrahydronaphthalene (the product of Step 2 of this Example), the title compound was prepared in 60% yield (8.5 g); MS DCl—NH$_3$ M/Z: 334 (M+H)+, (M+NH$_4$)+351; $^1$H NMR (CDCl$_3$) δ2.04–2.23 (3H, m), 2.33 (3H, s), 2.7–2.9 (1H, m), 2.92–3.05 (1H, m), 2.93, 3.07 (2H, dd, J=15 Hz), 3.71–3.81 (1H, m), 3.92–4.02 (1H, m), 4.08–4.18 (3H, m), 7.02–7.28 (8H, m).

Step 4:
1-Aminomethyl-2-[1-(1,3-dioxolane)-2-(3-methylphenyl)ethyl]-1,2,3,4-tetrahydronaphthalene Following the procedures of Step 5 of Example 1, replacing 1-cyano-2-[1-(1,3-dioxolane)-2-(3-methylphenyl)ethyl]-6-methoxy-1,2,3,4-tetrahydronaphthalene with 8.5 g (25.5 mmol) of 1-cyano-2-[1-(1,3-dioxolane)-2-(3-methylphenyl)ethyl]-1,2,3,4-tetrahydronaphthalene (the product of Step 3 of this Example), the title compound was prepared 93% yield (8 g); MS DCl—NH$_3$ M/Z: 338 (M+H)+; $^1$H NMR (CDCl$_3$) δ1.54–1.7 (1H, m), 2.07–2.22 (2H, m), 3.02 (3H, s), 2.54–3.0 (5H, m), 2.83–2.93 (2H, dd, J=18.0 Hz), 3.3–3.52 (2H, m), 3.65–3.72 (1H, m), 3.82–3.9 (1H, m), 6.97–7.22 (8H, m).

Step 5:
cis-2,3,3a,4,5,9b-Hexahydro-3-(3-methylphenyl)methyl-1H-benz[e]isoindole hydrochloride Following the procedures of Step 6 of Example 1, replacing 1-aminomethyl-2-[1-(1,3-dioxolane)-2-phenylethyl]-7-methoxy-1,2,3,4-tetrahydronaphthalene with 1-aminomethyl-2-[1-(1,3-dioxolane)-2-(3-methylphenyl)ethyl]-1,2,3,4-tetrahydronaphthalene (the product of Step 4 of this Example), the title compound was prepared in 70% yield (5 g), m.p. 220°–222° C.; MS DCl—NH$_3$ M/Z: 278 (M+H)+. Analysis calculated for C$_{20}$H$_{24}$ClN: C, 76.53; H, 7.71; N, 4.46. Found: C, 76.29; H, 7.75; N, 4.45.

EXAMPLE 12 cis-2,3,3a,4,5,9b-Hexahydro-2-methyl-3-(3-methylphenyl)methyl-1H-benz[e]isoindole hydrochloride Following the procedures described in Example 2, replacing the product of Example 1 with 2.13 g (7.7 mmol) of the product of Example 11, the cis isomer of the title compound was prepared in 52% yield (1.16 g), m.p. 208°–210° C.; MS DCl—NH$_3$ M/Z: 292 (M+H)+; $^1$H NMR of free amine (CDCl$_3$) δ1.57–1.73 (1H, m), 1.93–2.03 (1H, m), 2.13–2.25 (1H, m), 2.35 (3H, s), 3.4 (3H, s), 2.5–2.97 (6H, m), 3.15–3.23 (1H, m), 3.26–3.75 (1H, m), 7.0–7.26 (8H, m). Analysis calculated for C$_{21}$H$_{26}$ClN+¼ H$_2$O: C, 75.88; H, 8.09; N, 4.21. Found: C, 75.82; H, 8.00; N, 4.33.

EXAMPLE 13 cis-2-Ethyl-2,3,3a,4,5,9b-hexahydro-3-(3-methylphenyl)methyl-1H-benz[e]isoindole hydrochloride Following the procedures described in Example 3, replacing the product of Example 1 with 1.1 g (3.97 mmol) of the product of Example 11, the title compound was prepared in 75% yield (0.82 g), m.p. 250°-252° C.; MS DCl—NH₃ M/Z: 306 (M+H)⁺; ¹H NMR (CDCl₃) δ1.03-1.18 (3H, t, J=7.5 Hz), 1.6-2.5 (5H, m), 2.13-2.23 (1H, m), 2.35 (3H, s), 2.5-3.0 (5H, m), 3.03-3.15 (1H, m), 3.2-3.33 (1H, m), 7.0-7.22 (8H, m). Analysis calculated for C₂₂H₂₈ClN: C, 76.26; H, 8.29; N, 4.04. Found: C, 75.98; H, 8.11; N, 3.86.

EXAMPLE 14 trans-2,3,3a,4,5,9b-Hexahydro-2-methyl-3-(3-methylphenyl)methyl-1H-benz[e]isoindole methanesulfonic acid salt

Step 1:
1-Cyano-2-(3-methylphenyl)methylcarbonyl-1,2,3,4-tetrahydronaphthalene Following the procedures described in Step 1 of Example 6, replacing 1-cyano-2-[1-(1,3-dithiane)-2-phenylethyl]-6-methoxy-1,2,3,4-tetrahydronaphthalene with 2.35 g (6.2 mmol) of 1-cyano-2-[1-(1,3-dithiane)-2-(3-methylphenyl)ethyl]-1,2,3,4-tetrahydronaphthalene (the product of Step 2 of Example 11) the title compound was prepared in 67% yield (1.2 g) as a 2:1 mixture of the cis and trans isomers; MS DCl—NH₃ M/Z: 290 (M+H)⁺.

Step 2:
2,3,3a,4,5,9b-Hexahydro-3-(3-methylphenyl)methyl-1H-benz[e]isoindole Following the procedures described in Step 2 of Example 6, replacing 1-cyano-6-methoxy-2-phenylmethylcarbonyl-1,2,3,4-tetrahydronaphthalene (the product of Step 1 of Example 6) with the product of Step 1 above, 1-cyano-2-(3-methylphenyl)methylcarbonyl-1,2,3,4-tetrahydronaphthalene, the title compound was prepared; MS DCl—NH₃ M/Z: 278 (M+H)⁺.

Step 3:
trans-2,3,3a,4,5,9b-Hexahydro-2-methyl-3-(3-methylphenyl)methyl-1H-benz[e]isoindole methanesulfonic acid salt Following the procedures described in Example 7, replacing the product of Example 6 with the product of Step 2 of this Example, the title compound was prepared, m.p. 128°-130° C.; MS DCl—NH₃ M/Z: 292 (M+H)⁺; ¹H NMR (CDCl₃) δ1.45-1.6 (1H, m), 1.73-1.87 (1H, m), 2.02-2.2 (1H, m), 2.37 (3H, s), 2.77 (3H, d, J=6 Hz), 2.85 (3H, s), 2.9-3.3 (2H, m), 3.05-3.23 (3H, m), 3.35-3.45 (1H, m), 3.53-3.63 (1H, m), 4.03-4.18 (1H, m), 6.88-6.92 (1H, d, J=9 Hz), 7.07-7.3 (7H, m). Analysis calculated for C₂₂H₂₉NO₃S+H₂O: C, 65.16; H, 7.70; N, 3.45. Found: C, 64.73; H, 7.23; N, 3.39.

EXAMPLE 15 cis-3-(3-Fluorophenyl)methyl-2,3,3a,4,5,9b-hexahydro-1H-benz[e]isoindole hydrochloride

Step 1: 2-(3-Fluorophenyl)methyl-1,3-dithiane 1,3-Dithiane (12 g, 0.1 mol) was dissolved in 150 mL of anhydrous THF under a nitrogen atmosphere. The resultant solution was cooled to −78° C. and n-butyllithium (44 mL of a 2.5M solution of in hexane, 0.11 mol) was added. The reaction mixture was warmed to −23° C. and then stirred at −23° C. for 0.5 h. The reaction mixture was recooled to −78° C. and 25 g (0.135 mol) of 3-fluorobenzyl bromide was added over a 15 minute period. The reaction mixture was stirred for 3 h at ambient temperature and then diluted with methylene chloride, washed with aqueous ammonium chloride solution and brine, dried over anhydrous magnesium sulfate, filtered and concentrated under reduced pressure. The residue was distilled to afford 15.2 g (66.7% yield) of the title compound, b.p. 135°-140° C. (0.5 mm Hg); MS DCl—NH₃ M/Z: 229 (M+H)⁺; ¹H NMR (CDCl₃) δ1.77-1.95 (1H, m), 2.05-2.18 (1H, m), 2.8-2.9 (4H, m), 3.02 (2H, d, J=7.5 Hz), 4.23 (1H, t, J=7.5 Hz), 6.9-7.1 (3H, m), 7.23-7.33 (1H, m).

Step 2:
1-Cyano-2-[1-(13-dithiane)-2-(3-fluorophenyl)ethyl]-1,2,3,4-tetrahydronaphthalene Following the procedures described in Step 3 of Example 1, replacing 1-cyano-6-methoxy-3,4-dihydronaphthalene with 8.37 g (54 mmol) of 1-cyano-3,4-dihydronaphthalene (the product of Step 1 of Example 9) and 2-phenylmethyl-1,3-dithiane with 13.68 g (60 mmol) of 2-(3-fluorophenyl)methyl-1,3-dithiane (the product of Step 1 of this Example), the title compound was prepared in 45% yield (10.4 g); MS DCl—NH₃ M/Z: 384 (M+H)⁺; ¹H NMR (CDCl₃) δ1.72-2.20 (3H, m), 2.48-3.0 (7H, m), 3.1-3.2 (1H, m), 3.07, 3.75 (2H, dd, J=15 Hz), 4.5 (1H, dd, J=4.6 Hz, 1.5 Hz), 6.94-7.03 (1H, m), 7.14-7.34 (7H, m).

Step 3:
1-Cyano-2-[1-(1,3-dioxolane)-2-(3-fluorophenyl)ethyl]-1,2,3,4-tetrahydronaphthalene Following the procedures described in Step 4 of Example 1, replacing 1-cyano-2-[1-(1,3-dithiane)-2-phenylethyl]-6-methoxy-1,2,3,4-tetrahydronaphthalene with 10.4 g (27 mmol) of 1-cyano-2-[1-(13-dithiane)-2-(3-fluorophenyl)ethyl]-1,2,3,4-tetrahydronaphthalene, from Step 2 of this Example, the title compound was prepared in 52% yield (4.7 g); MS DCl—NH₃ M/Z: 338 (M+H)⁺.

Step 4:
1-Aminomethyl-2-[1-(1,3-dioxolane)-2-(3-fluorophenyl)ethyl]-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 4.7 g (14 mmol) of 1-cyano-2-[1-(1,3-dioxolane)-2-(3-fluorophenyl)ethyl]-1,2,3,4-tetrahydronaphthalene, from Step 3 of this Example, the title compound was prepared in 86% yield (4.1 g); MS DCl—NH₃ M/Z: 342 (M+H)⁺; ¹H NMR (CDCl₃) δ1.5-1.7 (1H, m), 2.07-2.23 (2H, m), 2.57-3.04 (5H, m), 2.85, 3.02 (2H, dd, J=15 Hz), 3.37-3.53 (2H, m), 3.67-3.74 (1H, m), 3.82-3.91 (1H, m), 6.88-7.3 (8H, m).

Step 5:
cis-3-(3-Fluorophenyl)methyl-2,3,3a,4,5,9b-hexahydro-1H-benz[e]isoindole hydrochloride Following the procedures described in Step 6 of Example 1, replacing 1-aminomethyl-2-[1-(1,3-dioxolane)-2-phenylethyl]-6-methoxy-1,2,3,4-tetrahydronaphthalene with 4.1 g (12 mmol) of 1-aminomethyl-2-[1-(1,3-dioxolane)-2-(3-fluorophenyl)ethyl]-1,2,3,4-tetrahydronaphthalene, from Step 4 of this Example, the title compound was prepared in 33% yield (1.3 g), m.p. 255°-258° C.; MS DCl—NH₃ M/Z: 282 (M+H)⁺; ¹H NMR (CDCl₃) δ1.45-1.63 (1H, m), 1.83-1.95 (1H, m), 2.2-2.33 (1H, m), 2.53-3.0 (5H, m), 3.33-3.53 (2H, m), 3.0-3.68 (1H, m), 6.85-7.2 (7H, m), 7.2-7.32 (1H, m).

Analysis calculated for $C_{20}H_{21}ClFN$: C, 71.80; H, 6.66; N, 4.41. Found: C, 71.65; H, 6.68; N, 4.41.

EXAMPLE 16 cis-3-(3-Fluorophenyl)methyl-2,3,3a,4,5,9b-hexahydro-2-methyl-1H-benz[e]isoindole hydrochloride Following the procedures described in Example 2, replacing the product of Example 1 with the product of Example 15, the title compound was prepared in 65% yield (0.8 g), m.p. 208°–210° C.; MS DCl—$NH_3$ M/Z: 296 $(M+H)^+$; $^1H$ NMR of the free base ($CDCl_3$) δ1.57–1.73 (1H, m), 1.87–1.97 (1H, m), 2.13–2.24 (1H, m), 2.38 (3H, s), 2.5–2.65 (1H, m), 2.68–2.88 (2H, m), 2.87–3.0 (3H, m), 3.15–3.23 (1H, m), 3.29–3.39 (1H, m), 6.87–7.3 (8H, m). Analysis calculated for $C_{20}H_{23}ClFN$: C, 72.39; H, 6.99; N, 4.22. Found: C, 71.91; H, 6.95; N, 4.12.

EXAMPLE 17

3-(4-Fluorophenyl)methyl-2,3,3a,4,5,9b-hexahydro-1H-benz[e]isoindole methanesulfonic acid salt

Step 1: 2-(4-Fluorophenyl)methyl-1,3-dithiane 1,3-Dithiane (20 g, 166 mmol) was dissolved in 250 mL of anhydrous THF under a nitrogen atmosphere. The resultant solution was cooled to −78° C. and n-butyllithium (128 mL of a 1.5M solution in hexane, 199 m mol) was added. The reaction mixture was warmed to 0° C. and then stirred at 0° C. for 0.5 h. The reaction mixture was recooled to −78° C. and 25 g (0.135 mol) of 3-fluorobenzyl bromide was added over a 15 minute period. The reaction mixture was stirred for 3 h at ambient temperature and then the reaction was quenched with aqueous ammonium chloride solution. The layers were separated and the aqueous layer was extracted with ethyl acetate. The combined organic extracts were dried over anhydrous magnesium sulfate, filtered and concentrated under reduced pressure. The residue was distilled to afford 35.5 g (94% yield) of the title compound, b.p. 125°–145° C. (0.75 mm Hg); MS DCl—$NH_3$ M/Z: 229 $(M+H)^+$; $^1H$ NMR ($CDCl_3$) δ1.76–1.95 (1H, m), 2.05–2.19 (1H, m), 2.78–2.98 (4H, m), 2.99 (2H, d, J=9 Hz), 4.21 (1H, t, J=9 Hz), 6.93–7.05 (2H, m), 7.16–7.25 (2H, m).

Step 2: 1-Cyano-2-[1-(13-dithiane)-2-(4-fluorophenyl)ethyl]-1,2,3,4-tetrahydronaphthalene 2-(4-Fluorophenyl)methyl-1,3-dithiane (16.2 g, 70.9 mmol), from Step 1, was dissolved in 100 mL of anhydrous THF and the resultant solution was cooled to 0° C. n-Butyl lithium (28.4 mL of a 2.5M solution in hexane) was added and the resultant solution was added to a solution of 10 g (64.4 mmol) of 1-cyano-3,4-dihydronaphthalene (the product of Step 1 of Example 9) in 100 mL of anhydrous THF at −78° C. The reaction mixture was allowed to warm to ambient temperature, stirred at ambient temperature for 2 h and then the reaction was quenched with concentrated aqueous ammonium chloride solution. The resultant layers were separated and the aqueous layer was extracted with two portions of ethyl acetate. The combined organic extracts were washed with brine, dried over anhydrous magnesium sulfate, filtered and concentrated in vacuo. The residue was purified by chromatography on silica gel eluted with 8:1 hexane:ethyl acetate to give 8.4 g (34% yield) of the title compound as a yellow foam; MS DCl—$NH_3$ M/Z: 384 $(M+H)^+$, 401 $(M+NH_4)^+$; $^1H$ NMR ($CDCl_3$) δ1.56–2.19 (4H, m), 2.42–3.22 (7H, m), 3.04, 3.71 (2H, dd, J=15 Hz), 4.51 (1H, dd, J=5 Hz, 1.5 Hz), 6.88–7.44 (8H, m).

Step 3: 1-Cyano-2-[1-(1,3-dioxolane)-2-(4-fluorophenyl)ethyl]-1,2,3,4-tetrahydronaphthalene Following the procedures described in Step 4 of Example 1, replacing 1-cyano-2-[1-(1,3-dithiane)-2-phenylethyl]-6-methoxy-1,2,3,4-tetrahydronaphthalene with 8.4 g (21.9 mmol) of 1-cyano-2-[1-(13-dithiane)-2-(4-fluorophenyl)ethyl]-1,2,3,4-tetrahydronaphthalene, from Step 2 of this Example, the title compound was prepared; MS DCl—$NH_3$ M/Z: 338 $(M+H)^+$, 355 $(M+NH_4)^+$.

Step 4: 1-Aminomethyl-2-[1-(1,3-dioxolane)-2-(4-fluorophenyl)ethyl]-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 4.7 g (14 mmol) of 1-cyano-2-[1-(1,3-dioxolane)-2-(4-fluorophenyl)ethyl]-1,2,3,4-tetrahydronaphthalene, from Step 3 of this Example, the title compound was prepared.

Step 5: 3-(4-Fluorophenyl)methyl-2,3,3a,4,5,9b-hexahydro-1H-benz[e]isoindole methanesulfonic acid salt 1-Aminomethyl-2-[1-(1,3-dioxolane)-2-(4-fluorophenyl)ethyl]1,2,3,4-tetrahydronaphthalene (3.35 g (9.8 mmol), from Step 4 of this Example, was dissolved in 120 mL of THF and 60 mL of 3N aqueous hydrochloric acid solution was added to the resultant solution. The reaction mixture was heated at 80° C. for 1 h. The solvents were removed in vacuo and 250 mL of methanol was added to the residue. A solution of sodium cyanoborohydride (1.85 g, 29.4 mmol) in 40 mL of methanol was added dropwise to the resultant solution. After removing the solvent in vacuo, the residue was dissolved in water and 45% aqueous sodium hydroxide solution was added until the solution was basic on litmus paper. The resultant layers were separated and the aqueous layer was extracted with three portions of methylene chloride. The combined organic extracts were dried over anhydrous magnesium sulfate, filtered and concentrated under reduced pressure. The residue was purified by chromatography on silica gel eluted with ethyl acetate:water:formic acid (18:1:1) to give the formic acid salt of the title compound. The formic acid salt was treated with a solution of methanesulfonic acid in acetone/diethyl ether to give the title compound; MS DCl—$NH_3$ M/Z: 282$(M+H)^+$; $^1$NMR ($CDCl_3$) δ1.45–1.63 (1H, m), 1.83–1.95 (1H, m), 2.2–2.33 (1H, m), 2.53–3.0 (5H, m), 3.33–3.53 (2H, m), 3.0–3.68 (1H, m), 6.85–7.2 (7H, m), 7.2–7.32 (1H, m). Analysis calculated for $C_{21}H_{26}FNO_3S$: C, 63.64; H, 6.41; N, 3.71. Found: C, 63.37; H, 6.45; N, 3.65.

EXAMPLE 18 cis-3-(4-Fluorophenyl)methyl-2,3,3a,4,5,9b-hexahydro-2-methyl-1H-benz[e]isoindole methanesulfonic acid salt Following the procedures described in Example 2, replacing the product of Example 1 with the product of Step Example 17, the title compound was prepared as a mixture of the cis and trans isomers. The cis-anti product was isolated by chromatography on silica gel eluted with 2:1 hexane:diethyl ether saturated with ammonia and converted to the methanesulfonic acid salt; MS DCl—NH$_3$ M/Z: 296 (M+H)$^+$; $^1$H NMR (CDCl$_3$) δ1.82–2.09 (2H, m), 2.47–3.01 (3H, m), 2.79 (3H, s), 2.84 (3H, d, J=5 Hz), 3.18–3.40 (3H, m), 3.57–3.71 (2H, m), 3.92–4.06 (1H, m), 6.94–7.22 (6H, m), 7.33–7.42 (2H, m). Analysis calculated for C$_{21}$H$_{26}$FNO$_3$S: C, 64.43; H, 6.69; N, 3.58. Found: C, 64.34; H, 6.73; N, 3.55.

EXAMPLE 19 trans-2,3,3a,4,5,9b-Hexahydro-3-(3-methoxyphenyl)-methyl-1H-benz[e]isoindole hydrochloride Step 1: 2-(3-Methoxyphenyl)methyl-1,3-dithiane Following the procedures described in Step 1 of Example 1, replacing phenylacetaldehyde with 21.6 g (158.6 mmol) of 3-methoxyphenylacetaldehyde, the title compound was prepared in 28% yield (17.5 g), m.p. 54°–56° C.; MS DCl—NH$_3$ M/Z: 391 (M+H)$^+$.

Step 2:
1-Cyano-2-[1-(13-dithiane)-2-(3-methoxyphenyl)ethyl]-1,2,3,4-tetrahydronaphthalene Following the procedures described in Step 2 of Example 17, replacing 2-(4-fluorophenyl)methyl-1,3-dithiane with 18.57 g (77.37 mmol) of 2-(3-methoxyphenyl)methyl-1,3-dithiane, from Step 1, the title compound was prepared in 35% yield (9.2 g); MS DCl—NH$_3$ M/Z: 396 (M+H)$^+$, 413 (M+NH$_4$)$^+$.

Step 3:
1-Cyano-2-(3-methoxyphenyl)methylcarbonyl-1,2,3,4-tetrahydronaphthalene

Following the procedures described in Step 1 of Example 6, replacing 1-cyano-2-[1-(1,3-dithiane)-2-phenylethyl]-6-methoxy-1,2,3,4-tetrahydronaphthalene with 8.85 g (22.4 mmol) of 1-cyano-2-[1-(1,3-dithiane)-2-(3-methoxyphenyl)ethyl]-1,2,3,4-tetrahydronaphthalene (the product of Step 2) the title compound was prepared in 67% yield (4 g); MS DCl—NH$_3$ M/Z: 306 (M+H)$^+$, 323 (M+NH$_4$)$^+$; $^1$H NMR (CDCl$_3$) δ2.1–2.28 (1H, m), 2.3–2.42 (1H, m), 2.77–3.5 (3H, m), 3.8 (3H, s), 3.85–3.92 (2H, m), 4.08–4.2 (1H, m), 6.77–6.9 (3H, m), 7.1–7.3 (5H, m).

Step 4:
trans-2,3,3a,4,5,9b-Hexahydro-3-(3-methoxyphenyl)-methyl-1H-benz[e]isoindole hydrochloride Following the procedures described in Step 2 of Example 6, replacing 1-cyano-6-methoxy-2-phenylmethyl-carbonyl-1,2,3,4-tetrahydronaphthalene (the product of Step 1 of Example 6) with 4 g (13.15 mmol) of the product of Step 3 above, 1-cyano-2-(3-methylphenyl)methylcarbonyl-1,2,3,4-tetrahydronaphthalene, the desired compound was prepared as the hydrochloride salt in 60% yield (2.2 g), m.p. 210°–212 ° C.; MS DCl—NH$_3$ M/Z: 294 (M+H)$^+$; $^1$H NMR (CDCl$_3$) δ1.5–1.78 (1H, m), 1.88–1.98 (1H, m), 2.68–2.78 (1H, m), 2.88–3.0 (4H, m), 3.14–3.25 (1H, m), 3.5–3.6 (1H, m), 3.8 (3H, s), 6.72–7.0 (4H, m), 7.05–7.25 (4H, m). Analysis calculated for C$_{20}$H$_{24}$ClNO: C, 72.83; H, 6.98; N, 4.24. Found: C, 72.74; H, 7.38; N, 4.19.

EXAMPLE 20 trans-2,3,3a,4,5,9b-Hexahydro-3-(3-methoxyphenyl)-methyl-2-methyl-1H-benz[e]isoindole hydrochloride A solution of 1.3 g (4.43 mmol) of 2,3,3a,4,5,9b-hexahydro-3-(3-methylphenyl)methyl-1H-benz[e]isoindole (the product of Example 19) and 5 mL of formalin (37% aqueous formaldehyde solution) in 95 mL of methanol was hydrogenated at ambient temperature and 4 atmospheres of hydrogen for 24 h in the presence of 0.65 g of 20% palladium on carbon. The hydrogenation mixture was filtered and the filtrate was concentrated in vacuo. The residue was adsorbed on silica gel and chromatographed on silica gel eluted with ethyl acetate:formic acid:water (18:1:1) to give the formic acid salt of the desired product which was converted to the free the amine product. The amine was converted to the title compound by treatment with hydrogen chloride in methanol solution, m.p. 188°–19° C.; MS DCl—NH$_3$ M/Z: 208 (M+H)$^+$; $^1$H NMR of the methanesulfonic acid salt (CDCl$_3$) δ1.43–1.5 (1H, m), 1.74–1.84 (1H, m), 2.0–2.15 (1H, m), 2.72 (3H, s), 2.88–2.98 (2H, m), 3.04–3.18 (3H, m), 3.3–3.52 (2H, m), 3.75–3.85 (1H, m), 3.82 (3H, s), 6.78–6.92 (4H, m), 7.08–7.3 (4H, m). Analysis calculated for C$_{21}$H$_{26}$ClNO: C, 73.63; H, 7.28; N, 4.07. Found: C, 72.82; H, 7.62; N, 4.00.

EXAMPLE 21 cis-2,3,3a,4,5,9b-Hexahydro-6-methoxy-3-phenylmethyl-1H-benz[e]isoindole methanesulfonic acid salt Step 1: 1-Cyano-5-methoxy-3,4-dihydronaphthalene Following the procedures described in Step 2 of Example 1, replacing 6-methoxy-α-tetralone with 5-methoxy-α-tetralone (commercially available from Aldrich Chemical Company), the title compound was prepared.

Step 2:
1-Cyano-2-[1-(1,3-dithiane)-2-phenylethyl]-5-methoxy-1,2,3,4-tetrahydronaphthalene 2-Benzyl-1,3-dithiane (18.7 g, 89 mmol), the product of Step 1 of Example 1, was dissolved in 200 mL of anhydrous THF under a nitrogen atmosphere and the resultant solution was cooled to 0° C. To the stirred solution was slowly added n-butyllithium (35.6 mL of a 2.5M solution in hexane) and the resultant solution was stirred for 1.5 h at 0° C. The solution was then cooled to −78° C. and a solution of 15 g (81 mmol) of 1-cyano-5-methoxy-3,4-dihydronaphthalene (the product of Step 1 of this Example) in 150 mL of anhydrous THF was added in a continuous stream via cannula. The reaction mixture was allowed to warm to ambient temperature and, after stirring at ambient temperature for 3 h, the reaction was quenched by the addition of saturated aqueous ammonium chloride solution. The resultant layers were separated and the aqueous layer was extracted with ethyl acetate. The combined organic layers were dried over anhydrous magnesium sulfate, filtered and concentrated in vacuo. Trituration with diethyl ether gave 17.4 of the title compound. The ether solution was concentrated and the residue was purified by chromatography on silica gel eluted with 6:1 hexane:ethyl acetate to give another 11.4 g of the title compound, for a total of 28.8 g (90% yield) of the desired product; MS DCl—NH$_3$ M/Z: 396 (M+H)$^+$; $^1$H NMR (CDCl$_3$) δ1.70–2.18 (3H, m), 2.49–2.78 (6H, m), 2.85–2.96 (1H, m), 3.07–3.19 (1H, m), 3.12, 3.72 (2H, dd, J=15 Hz), 3.84 (3H, s), 4.49 (1H, dd, J=1.5 Hz, 4.5 Hz), 6.78 (1H, d, J=8 Hz), 6.91 (1H, d, J=8 Hz), 7.20 (1H, t, J=8 Hz), 7.24–7.43 (5H, m).

Step 3:
1-Cyano-2-[1-(1,3-dioxolane)-2-phenylethyl]-5-methoxy-1,2,3,4-tetrahydronaphthalene A mixture of 12 g (30.3 mmol) of 1-cyano-2-[1-(1,3-dithiane)-2-phenylethyl]-5-methoxy-1,2,3,4-tetrahydronaphthalene from Step 2, 25 g (91 mmol) of mercury chloride and 75 mL of ethylene glycol in 75 mL of THF was refluxed under a nitrogen atmosphere for 7 h. The reaction mixture was allowed to cool to ambient temperature, diluted with 600 mL of methylene chloride and filtered through Celite filter aid. The filter cake was washed with methylene chloride and the combined filtrates were concentrated to give a mixture of a yellow oil and a purple semi-solid material. The oil was separated and partitioned between methylene chloride and water (4:1 v/v). The organic layer was saved and the aqueous layer was extracted with methylene chloride. The purple material was also partitioned between methylene chloride and water (4:1 v/v). The organic layer was again saved and the aqueous layer was extracted with two portions of methylene chloride. All of the organic layers were then combined, washed with two portions of water and then absorbed onto silica gel. The silica gel was dried under reduced pressure (on the rotory evaporator) and loaded onto a silica gel column which was then eluted with 6:1 hexane:ethyl acetate to give 6.2 g (58%) of the title compound; MS DCl—NH$_3$ M/Z: 350 (M+H)+, 367 (M+H$_4$)+; $^1$H NMR (CDCl$_3$) δ1.97–2.60 (4H, m), 2.92–3.21 (1H, m), 2.98, 3.12 (2H, dd, J=15 Hz), 3.50–4.18 (5H, m), 3.81 (3H, s), 6.73 (1H, d, J=8 Hz), 6.82 (1H, d, J=8 Hz), 7.05–7.39 (6H, m).

Step 4:
1-Aminomethyl-2-[1-(1,3-dioxolane)-2-phenylethyl]-5-methoxy-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 1-cyano-2-[1-(1,3-dioxolane)-2-phenylethyl]-5-methoxy-1,2,3,4-tetrahydronaphthalene, from Step 3 above, the title compound was prepared; MS DCl—NH$_3$ M/Z: 354 (M+H)+.

Step 5:
cis-2,3,3a,4,5,9b-Hexahydro-6-methoxy-3-phenylmethyl-1H-benz[e]isoindole methanesulfonic acid salt 1-Aminomethyl-2-[1-(1,3-dioxolane)-2-phenylethyl]-5-methoxy-1,2,3,4-tetrahydronaphthalene (6.0 g, 17.0 mmol), from Step 4, was dissolved in 240 mL of THF, 120 mL of 3N aqueous hydrochloric acid solution was added at ambient temperature and the resultant solution was heated at reflux temperature overnight. The solvents were removed in vacuo and the residue was dissolved in 150 mL of methanol. To the resultant methanol solution was added a solution of 3 g in 40 mL of methanol, dropwise over a 20 minute period. The reaction mixture was stirred at ambient temperature for 15 minutes and then concentrated in vacuo. The residue was partitioned between 15% aqueous potassium hydroxide solution and methylene chloride (1:5 v/v) and the aqueous layer was extracted with two portions of methylene chloride. The combined organic layers were concentrated in vacuo. The residue was treated with methanol saturated with anhydrous hydrogen chloride and the solution was concentrated in vacuo. The residue was dried with toluene three times and then dissolved in hot acetone. The crystals which precipitated upon cooling to ambient temperature were dissolved in aqueous potassium hydroxide solution and the aqueous solution was extracted with four portions of methylene chloride. The combined organic layers were dried over anhydrous magnesium sulfate, filtered and concentrated in vacuo. The free base was converted to the title compound using 1.1 equivalents of methanesulfonic acid in diethyl ether/acetone, m.p. 129.5°–131.0° C.; MS DCl—NH$_3$ M/Z: 294 (M+H)+; $^1$H NMR of the free base (CDCl$_3$) δ1.36–1.54 (1H, m), 1.69 (1H, bs), 1.87–1.99 (1H, m), 2.12–2.41 (2H, m), 2.71–3.12 (4H, m), 3.28–3.49 (2H, m), 3.58–3.68 (1H, m), 3.81 (3H, s), 6.65 (1H, d, J=8 Hz), 6.68 (1H, d, J=8 Hz), 7.08 (1H, t, J=8 Hz), 7.16–7.34 (5H, m). Analysis calculated for C$_{21}$H$_{27}$NO$_4$S: C, 64.79; H, 6.99; N, 4.00. Found: C, 64.63; H, 6.99; N, 3.49.

EXAMPLE 22 cis-2,3,3a,4,5,9b-Hexahydro-6-methoxy-2-methyl-3-phenylmethyl-1H-benz[e]isoindole methanesulfonic acid salt Following the procedures described in Example 2, replacing the product of Example 1 with the product of Example 21, the title compound was prepared, m.p. 170°–171° C.; MS DCl—NH$_3$ M/Z: 308 (M+H)+; $^1$H NMR of the free base (CDCl$_3$) δ1.51–1.68 (1H, m), 1.97–2.30 (3H, m), 2.40 (3H, s), 2.72–3.08 (5H, m), 3.16–3.35 (2H, m), 3.80 (3H, s), 6.64 (1H, d, J=8 Hz), 6.66 (1H, d, J=8 Hz), 7.08 (1H, t, J=8 Hz), 7.18–7.36 (5H, m). Analysis calculated for C$_{22}$H$_9$NO$_4$S: C, 65.48; H, 7.24; N, 3.47. Found: C, 65.22; H, 7.22; N, 3.42.

EXAMPLE 23 cis-2-Ethyl-2,3,3a,4,5,9b-hexahydro-6-methoxy-3-phenylmethyl-1H-benz[e]isoindole methanesulfonic acid salt Following the procedures described in Example 3, replacing the product of Example 1 with 2.52 g (8.59 mmol) of the free amine product of Example 21, the title compound was prepared, m.p. 166.0°–167.1° C.; MS DCl—NH$_3$ M/Z: 322 (M+H)+; $^1$H NMR of the free base (CDCl$_3$) δ1.08 (3H, t, J=7.5 Hz), 1.54–1.72 (1H, m), 1.97–2.43 (4H, m), 2.74–3.39 (8H, m), 3.80 (3H, s), 6.64 (1H, d, J=8 Hz), 6.67 (1H, d, J=8 Hz), 7.08 (1H, t, J=8 Hz), 7.16–7.35 (5H, m). Analysis calculated for C$_{23}$H$_{31}$NO$_4$S: C, 66.16; H, 7.48; N, 3.35. Found: C, 65.79; H, 7.44; N, 3.38.

EXAMPLE 24 cis-3-(3-Fluorophenyl)methyl-2,3,3a,4,5,9b-hexahydro-6-methoxy-2-methyl-1H-benz[e]isoindole hydrochloride Step 1:
1-Cyano-2-[1-(1,3-dithiane)-2-(3-fluorophenyl)ethyl]-5-methoxy-1,2,3,4-tetrahydronaphthalene Following the procedures described in Step 3 of Example 1, replacing 1-cyano-6-methoxy-3,4-dihydronaphthalene with 1-cyano-5-methoxy-3,4-dihydronaphthalene (the product of Step 1 of Example 21) and 2-phenylmethyl-1,3-dithiane with 2-(3-fluorophenyl)methyl-1,3-dithiane (the product of Step 1 of Example 15), the title compound was prepared in 4.8

(68%) yield. m.p. 78°–88° C.; MS DCl—NH₃ M/Z: 414 (M+H)⁺; ¹H NMR (CDCl₃) δ1.72–2.14 (3H, m), 2.5–3.05 (8H, m), 3.1, 3.72 (2H, dd, J=15 Hz), 3.85 (3H, s), 4.49 (1H, dd, J=4.6, 1.5 Hz), 6.8 (1H, d, J=9 Hz), 6.92 (1H, dd, J=9 Hz), 6.9–7.3 (5H, m).

Step 2:
1-Cyano-2-[1-(1,3-dioxolane)-2-(3-fluorophenyl)ethyl]-5-methoxy-1,2,3,4-tetrahydronaphthalene Following the procedures described in Step 4 of Example 1, replacing 1-cyano-2-[1-(1,3-dithiane)-2-phenylethyl]-6-methoxy-1,2,3,4-tetrahydronaphthalene with 1-cyano-2-[1-(13-dithiane)-2-(3-fluorophenyl)ethyl]-5-methoxy-1,2,3,4-tetrahydronaphthalene, from Step 1 of this Example, the title compound was prepared in 46% yield m.p. 80°–82° C.; MS DCl—NH₃ M/Z: 368 (M+H)⁺; ¹H NMR (CDCl₃) δ1.95–2.28 (3H, m), 2.42–2.58 (1H, m), 2.95–3.07 (1H, m), 2.97, 3.14 (2H, dd, J=15 Hz), 3.68–3.75 (1H, m), 3.82 (3H, s), 3.88–3.98 (1H, m), 4.05–4.17 (3H, m), 6.75 (1H, d, J=9.0 Hz), 6.84 (1H, d, J=9 Hz), 6.88–7.25 (5H, m).

Step 3:
1-Aminomethyl-2-[1-(1,3-dioxolane)-2-(3-fluorophenyl)ethyl]-5-methoxy-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 1-cyano-2-[1-(1,3-dioxolane)-2-(3-fluorophenyl)ethyl]-5-methoxy-1,2,3,4-tetrahydronaphthalene, from Step 2 of this Example, the title compound was prepared; MS DCl—NH₃ M/Z: 3724(M+H)⁺, 389 (M+NH₄)⁺; ¹H NMR (CDCl₃) δ1.62–2.55 (4H, m), 2.83–3.1 (1H, m), 2.92, 3.07 (2H, dd, J=15 Hz), 3.6–3.8 (7H, m), 3.84 (3H, s), 6.62–7.3 (7H, m).

Step 4:
3-(3-Fluorophenyl)methyl-2,3,3a,4,5,9b-hexahydro-6-methoxy-1H-benz[e]isoindole Following the procedures described in Step 6 of Example 1, replacing 1-aminomethyl-2-[1-(1,3-dioxolane)-2-phenylethyl]-6-methoxy-1,2,3,4-tetrahydronaphthalene with 1-aminomethyl-2-[1-(1,3-dioxolane)-2-(3-fluorophenyl)ethyl]-5-methoxy-1,2,3,4-tetrahydronaphthalene, from Step 3 of this Example, the title compound was prepared; MS DCl—NH₃ M/Z: 312 (M+H)⁺; ¹H NMR (CDCl₃) δ1.38–1.55 (1H, m), 1.85–2.0 (1H, m), 2.18–2.3 (1H, m), 2.78–3.02 (5H, m), 3.0–3.15 (1H, m), 3.3–3.4 (1H, m), 3.55–3.7 (1H, m), 3.8 (3H, s), 6.60–6.75 (2H, m), 6.85–7.15 (4H, m), 7.2–7.3 (1H, m).

Step 5:
cis-3-(3-Fluorophenyl)methyl-2,3,3a,4,5,9b-hexahydro-6-methoxy-2-methyl-1H-benz[e]isoindole hydrochloride Following the procedures described in Example 2, replacing the product of Example 1 with 1.6 g (5.46 mmol) of the product of Step 4 of this Example, the title compound was prepared in 34% yield (0.6 g), m.p. 226°–228° C.; MS DCl—NH₃ M/Z: 326 (M+H)⁺; ¹H NMR (CDCl₃) δ1.9–2.03 (1H, m), 2.15–2.3 (1H, m), 2.3–2.5 (2H, m), 2.83 (3H, s), 3.0–3.13 (1H, m), 3.2–3.48 (3H, m), 3.5–3.68 (2H, m), 3.73 (3H, s), 3.88–4.00 (1H, m), 6.5–6.7 (2H, m), 6.9–7.1 (4H, m), 7.15–7.4 (1H, m). Analysis calculated for C₂₁H₂₅ClF+0.25H₂O·NO₂: C, 68.84; H, 7.02; N, 3.82. Found: C, 68.51; H, 7.00; N, 3.73.

EXAMPLE 25 cis-2-Ethyl-3-(3-fluorophenyl)methyl-2,3,3a,4,5,9b-hexahydro-6-methoxy-1H-benz[e]isoindole hydrochloride Following the procedures described in Example 3, replacing the product of Example 1 with the product of Step 4 of Example 24, the title compound was prepared, m.p. 197°–200° C.; MS DCl—NH₃ M/Z: 340 (M+H)⁺; ¹H NMR (CDCl₃) δ1.5 (3H, t, J=7.5 Hz), 1.58–1.7 (1H, m), 2.05–2.4 (3H, m), 2.75–3.15 (8H, m), 3.2–3.3 (1H, m), 3.8 (3H, s), 6.6–6.7 (2H, m), 6.88–7.15 (4H, m), 7.2–7.3 (1H, m). Analysis calculated for C₂₂H₂₇ClFNO+H₂O: C, 67.07; H, 7.35; N, 3.56. Found: C, 66.75; H, 6.92; N, 3.39.

EXAMPLE 26 trans-3-(3-Fluorophenyl)methyl-2,3,3a,4,5,9b-hexahydro-7-methoxy-1H-benz[e]isoindole hydrochloride Step 1:
1-Cyano-2-[1-(13-dithiane)-2-(3-fluorophenyl)ethyl]-6-methoxy-1,2,3,4-tetrahydronaphthalene Following the procedures described in Step 3 of Example 1, replacing 2-phenylmethyl-1,3-dithiane with 16.2 g of 2-(3-fluorophenyl)methyl-1,3-dithiane, the product of Step 1 of Example 15, the title compound was prepared; MS DCl—NH₃ M/Z: 414 (M+H)⁺; ¹H NMR (CDCl₃) of cis isomer δ1.82–1.97 (2H, m), 2.02–2.18 (1H, m), 2.44–2.97 (7H, m), 3.03–3.15 (1H, m) 3.05, 3.72 (2H, dd J=15 Hz), 3.78 (3H, s), 4.45 (1H, dd, J=4.6, 1.5 Hz), 6.70 (1H, d, J=3 Hz), 6.8 (1H, dd, J=9 Hz, 3 Hz), 6.93–7.30 (5H, m).

Step 2:
1-Cyano-2-(3-fluorophenyl)methylcarbonyl-6-methoxy-1,2,3,4-tetrahydronaphthalene Following the procedures described in Step 1 of Example 6, replacing 1-cyano-2-[1-(13-dithiane)-2-phenylethyl]-6-methoxy-1,2,3,4-tetrahydronaphthalene with 6 g (14.53 mmol) of the product of Step 1 of this Example, the title compound was prepared in 57% yield (2.67 g) as a mixture of cis and trans isomers; MS DCl—NH₃ M/Z: 341 (M+NH₄)⁺.

Step 3:
trans-3-(3-Fluorophenyl)methyl-2,3,3a,4,5,9b-hexahydro-7-methoxy-1H-benz[e]isoindole hydrochloride Following the procedures described in Step 2 of Example 6, replacing 1-cyano-6-methoxy-2-phenylmethylcarbonyl-1,2,3,4-tetrahydronaphthalene with 2.6 g (8 mmol) of the product of Step 2 of this Example, the title compound was prepared in 72% yield (1.8 g), m.p. 244°–246° C.; MS DCl—NH₃ M/Z: 312(M+H)⁺; ¹H NMR of the free amine (CDCl₃) δ1.44–1.6 (2H, m), 1.75–1.95 (2H, m), 2.68–2.97 (5H, m), 3.16–3.27 (1H, m), 3.48–3.6 (1H, m), 3.77 (3H, s), 6.6–7.3 (7H, m).

EXAMPLE 27 trans-3-(3-Fluorophenyl)methyl-2,3,3a,4,5,9b-hexahydro-7-methoxy-2-methyl-1H-benz[e]isoindole hydrochloride Following the procedures described in Example 7, replacing the product of Example 6 with 1.8 g (5.8 mmol) of the product of Example 26, the desired compound was prepared in 53% yield (1 g) as the hydrochloride salt; MS DCl—NH₃ M/Z: 326 (M+H)⁺; ¹H NMR (CDCl₃) δ1.35–1.75 (3H, m), 2.48 (3H, s), 2.53–2.63 (1H, m), 2.7–3.25 (7H, m), 3.75 (3H, s), 6.6–7.28 (7H, m). Analysis calculated for C₂₁H₂₅ClFNO: C, 69.70; H, 6.96; N, 3.87. Found: C, 69.21; H, 6.87; N, 3.83.

EXAMPLE 28 cis-3-(3-Fluorophenyl)methyl-2,3,3a,4,5,9b-hexahydro-7-methoxy-2-methyl-1H-benz[e]isoindole hydrochloride

Step 1:
1-Cyano-2-[1-(1,3-dioxolane)-2-(3-fluorophenyl)ethyl]-6-methoxy-1,2,3,4-tetrahydronaphthalene Following the procedures described in Step 4 of Example 1, replacing 1-cyano-2-[1-(13-dithiane)-2-phenylethyl]-6-methoxy-1,2,3,4-tetrahydronaphthalene with 1-cyano-2-[1-(13-dithiane)-2-(3-fluorophenyl)ethyl]-6-methoxy-1,2,3,4-tetrahydronaphthalene (the product of Step 1 of Example 26, the title compound was prepared; MS DCl—NH₃ M/Z: 368 (M+H)+; ¹H NMR (CDCl₃) δ2.0–2.15 (3H, m), 2.70–2.85 (1H, m), 2.92–3.1 (1H, m), 2.98, 3.14 (2H, dd, J=15 Hz), 3.65–3.75 (1H, m), 3.78 (3H, s), 3.88–3.92 (1H, m), 4.05–4.18 (3H, m), 6.65 (1H, d, J=3.0 Hz), 6.73 (1H, dd, J=9.0 Hz, 3.0 Hz), 6.9–7.3 (5H, m).

Step 2:
1-Aminomethyl-2-[1-(1,3-dioxolane)-2-(3-fluorophenyl)ethyl]-6-methoxy-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 2.7 g (7.35 mmol) of 1-cyano-2-[1-(1,3-dioxolane)-2-(3-fluorophenyl)ethyl]-6-methoxy-1,2,3,4-tetrahydronaphthalene from Step 1 of this Example, the title compound was prepared in 77% yield (2.1 g); MS DCl—NH₃ M/Z: 372 (M+H)+.

Step 3:
cis-3-(3-Fluorophenyl)methyl-2,3,3a,4,5,9b-hexahydro-7-methoxy-1H-benz[e]isoindole Following the procedures described in Step 6 of Example 1, replacing 1-aminomethyl-2-[1-(1,3-dioxolane)-2-phenylethyl]-6-methoxy-1,2,3,4-tetrahydronaphthalene with 2.4 g (6.5 mmol) of 1-aminomethyl-2-[1-(1,3-dioxolane)-2-(3-fluorophenyl)ethyl]-6-methoxy-1,2,3,4-tetrahydronaphthalene the title compound was prepared in 39.5% yield (0.9 g); MS DCl—NH₃ M/Z: 312 (M+H)+; ¹H NMR (CDCl₃) δ1.5–2.1 (3H, m), 2.2–2.4 (1H, m), 2.57–2.99 (4H, m), 3.28–3.57 (2H, m), 3.68–3.78 (1H, m), 3.77 (3H, s), 6.64 (1H, d, J=3 Hz), 6.7 (1H, dd, J=9 Hz, 3 Hz), 6.95 (1H, d, J=9 Hz), 6.85–7.3 (4H, m).

Step 4:
cis-3-(3-Fluorophenyl)methyl-2,3,3a,4,5,9b-hexahydro-7-methoxy-2-methyl-1H-benz[e]isoindole hydrochloride Following the procedures described in Example 2, replacing 2,3,3a,4,5,9b-hexahydro-7-methoxy-3-phenylmethyl-1H-benz[e]isoindole hydrochloride with 2.6 g (8 mmol) of the product of Step 3 of this Example, the desired product was prepared in 48% yield (0.35 g) as the hydrochloride salt; MS DCl—NH₃ M/Z: 326 (M+H)+; ¹H NMR (CDCl₃) δ1.6–1.8 (1H, m), 1.86–1.98 (1H, m), 2.13–2.27 (1H, m), 2.43 (3H, s), 2.5–2.67 (1H, m), 2.72–3.08 (5H, m), 3.2–3.4 (2H, m), 3.77 (3H, s), 6.6–7.3 (2H, m), 6.88–7.13 (4H, m), 7.23–7.33 (1H, m). Analysis calculated for C₂₁H₂₅ClFNO: C, 69.7; H, 6.9; N, 3.87. Found: C, 69.48; H, 7.13; N, 3.75.

EXAMPLE 29 cis-2,3,3a,4,5,9b-Hexahydro-7-methoxy-3-(3-methoxyphenyl)methyl-2-methyl-1H-benz[e]isoindole methanesulfonic acid salt

Step 1:
1-Cyano-2-[1-(1,3-dithiane)-2-(3-methoxyphenyl)ethyl]-6-methoxy-1,2,3,4-tetrahydronaphthalene Following the procedures described in Step 2 of Example 17, replacing 2-(4-fluorophenyl)methyl-1,3-dithiane with 5.01 g (20.8 mmol) of 2-(3-methoxyphenyl)methyl-1,3-dithiane (the product of Step 1 of Example 19), the title compound was prepared in 77% yield (6.8 g); MS DCl—NH₃ M/Z: 426 (M+H)+; ¹H NMR (CDCl₃) δ1.71–1.98 (2H, m), 2.02–2.18 (1H, m), 2.45–2.60 (2H, m), 2.63–3.16 (6H, m), 3.08, 3.71 (2H, dd, J=15 Hz), 3.79 (3H, s), 3.81 (3H, s), 4.44 (1H, dd, J=1.5 Hz, 4.5 Hz), 6.65–6.90 (3H, m), 6.96–7.01 (2H, m), 7.13–7.26 (2H, m).

Step 2:
1-Cyano-2-[1-(1,3-dioxolane)-2-(3-methoxyphenyl)ethyl]-6-methoxy-1,2,3,4-tetrahydronaphthalene Following the procedures described in Step 4 of Example 1, replacing 1-cyano-2-[1-(13-dithiane)-2-phenylethyl]-6-methoxy-1,2,3,4-tetrahydronaphthalene with 6.5 g (15.3 mmol) of 1-cyano-2-[1-(1,3-dithiane)-2-(3-methoxyphenyl)ethyl]-6-methoxy-1,2,3,4-tetrahydronaphthalene (the product of Step 1 of this Example), the title compound was prepared in 63% yield (3.69 g); MS DCl—NH₃ M/Z: 380 (M+H)+, 397 (M+NH₄)+; ¹H NMR (CDCl₃) δ2.02–2.22 (3H, m), 2.69–2.85 (1H, m), 2.91–3.09 (1H, m), 2.94, 3.08 (2H, dd, J=15 Hz), 3.62–3.84 (1H, m), 3.76 (3H, s), 3.78 (3H, s), 3.92–4.18 (4H, m), 6.60–6.95 (5H, m), 7.08–7.22 (2H, m).

Step 3:
1-Aminomethyl-2-[1-(1,3-dioxolane)-2-(3-methoxyphenyl)ethyl]-6-methoxy-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 3.7 g of 1-cyano-2-[1-(1,3-dioxolane)-2-(3-methoxyphenyl)ethyl]-6-methoxy-1,2,3,4-tetrahydronaphthalene (the product of Step 2 of this Example), the title compound was prepared in 84% yield (3.15 g); ¹H NMR (CDCl₃) δ1.37 (2H, bs), 1.51–1.68 (1H, m), 2.05–2.21 (2H, m), 2.53–3.07 (7H, m), 3.40–3.56 (2H, m), 3.65–3.95 (2H, m), 3.78 (6H, s), 6.62–6.80 (3H, m), 6.84–6.93 (2H, m), 7.03–7.21 (2H, m).

Step 4:
2,3,3a,4,5,9b-Hexahydro-7-methoxy-3-(3-methoxyphenyl)methyl-1H-benz[e]isoindole Following the procedures described in Step 6 of Example 1, replacing 1-aminomethyl-2-[1-(1,3-dioxolane)-2-phenylethyl]-6-methoxy-1,2,3,4-tetrahydronaphthalene with 3.15 g (8.21 mmol) of 1-aminomethyl-2-[1-(1,3-dioxolane)-2-(3-methoxyphenyl)ethyl]-6-methoxy-1,2,3,4-tetrahydronaphthalene (the product of Step 3 of this Example), the title compound was prepared in 94% yield (2.5 g); MS DCl—NH₃ M/Z 324 (M+H)+; ¹H NMR (CDCl₃) δ1.48–2.36 (3H, m), 2.59–3.05 (5H, m), 3.23–3.90 (3H, m), 3.79 (3H, s), 3.82 (3H, s), 6.64–7.07 (6H, m), 7.20–7.31 (1H, m).

Step 5:
cis-2,3,3a,4,5,9b-Hexahydro-7-methoxy-3-(3-methoxyphenyl)methyl-2-methyl-1H-benz[e]isoindole methanesulfonic acid salt Following the procedures described in Example 2, replacing the product of Example 1 with 2,3,3a,4,5,9b-hexahydro-7-methoxy-3-(3-methoxyphenyl)methyl-1H-benz[e]isoindole from Step 4 of this Example, the desired compound was prepared as the methanesulfonic acid salt; MS DCl—NH$_3$ M/Z: 338 (M+H)$^+$; $^1$H NMR of the free base (CDCl$_3$) δ1.52–1.72 (1H, m), 1.88–2.01 (1H, m), 2.12–2.24 (1H, m), 2.37 (3H, s), 2.49–2.97 (6H, m), 3.10–3.32 (2H, m), 3.74 (3H, s), 3.82 (3H, s), 6.58–6.97 (6H, m), 7.18–7.27 (1H, m). Analysis calculated for C$_{23}$H$_{31}$NO$_5$S: C, 63.71; H, 7.21; N, 3.28. Found: C, 63.57; H, 7.27; N, 3.23.

EXAMPLE 30
cis-2,3,3a,4,5,9b-Hexahydro-7-methoxy-2-methyl-3-(3-phenyl-1-propyl)-1H-benz[e]isoindole methanesulfonic acid salt

Step 1: 2-(3-Phenyl)propyl-1,3-dithiane

Following the procedures described in Step 1 of Example 1, replacing phenylacetaldehyde with 4-phenylbutanal, the title compound was prepared, b.p. 130°–138° C. (0.3 mm Hg); MS DCl—NH$_3$ M/Z: 239 (M+H)$^+$; $^1$H NMR (CDCl$_3$) δ1.58–2.5 (6H, m), 2.6–3.4 (6H, m), 4–4.4 (1H, m), 7.2–7.7 (5H, m).

Step 2:
1-Cyano-2-[1-(1,3-dithiane)-4-phenylbutyl]-6-methoxy-1,2,3,4-tetrahydronaphthalene To a solution of 5.4 g (22.7 mmol) of 2-(3-phenyl-1-propyl)-1,3-dithiane (from Step 1) in 100 mL of anhydrous THF, at 0° C. under a nitrogen atmosphere, was added 16 mL of a 1.5M solution of n-butyllithium (24 mmol) in hexane. The pale pink solution was stirred for approximately 2 h at 0° C. and then was cooled to −78° C. To the solution of 2-(3-phenyl-1-phenyl)-2-lithio-1,3-dithiane was then added, via cannula, a solution of 4 g (21.6 mmol) of 1-cyano-6-methoxy-3,4-dihydronaphthalene, (the product of Step 2 of Example 1), in 100 mL of THF, at −78° C. The pale yellow colored reaction mixture was allowed to warm to −20° C., was stirred at −20° C., under nitrogen, for 1.5 h, and then the reaction was quenched by the addition of 50 mL of saturated aqueous ammonium chloride solution. Methylene chloride was added and the layers were separated. The organic layer was dried over anhydrous magnesium sulfate, filtered and concentrated in vacuo. The residue was dissolved in diethyl ether/methylene chloride and purified by flash chromatography on silica gel eluted with 1:1 hexane:diethyl ether to afford 6.14 g (67% yield) of the title compound; MS DCl—NH$_3$ M/Z: 424 (M+H)$^+$, 441 (M+H$_4$)$^+$; $^1$H NMR (CDCl$_3$) δ1.42–1.58 (1H, m), 1.67–2.04 (6H, m), 2.12–2.24 (1H, m), 2.57–2.9 (9H, m), 3.78 (3H, s), 4.45 (1H, d, J=4.5 Hz), 6.67 (1H, d), 6.78 (1H, dd), 7.13–7.33 (6H, m).

Step 3:
1-Cyano-2-[1-(1,3-dioxolane)-4-phenylbutyl]-6-methoxy-1,2,3,4-tetrahydronaphthalene Following the procedures described in Step 4 of Example 1, replacing 1-cyano-2-[1-(13-dithiane)-2-phenylethyl]-6-methoxy-1,2,3,4-tetrahydronaphthalene with 4.23 g (10 mmol) of 1-cyano-2-[1-(1,3-dithiane)-4-phenylbutyl]-6-methoxy-1,2,3,4-tetrahydronaphthalene (the product of Step 2 of this Example), the title compound was prepared in 51% yield (1.91 g); MS DCl—NH$_3$ M/Z: 378 (M+H)$^+$, 395 (M+H$_4$)$^+$; $^1$H NMR (CDCl$_3$) δ1.6–2.17 (6H, m), 2.53–3.03 (5H, m), 3.77 (3H, s), 3.9–4.35 (5H, m), 6.63 (1H, d, J=3 Hz), 6.75 (1H, dd, J=9 Hz), 7.1–7.4 (6H, m).

Step 4:
1-Aminomethyl-2-[1-(1,3-dioxolane)-4-phenylbutyl]-6-methoxy-1,2,3,4-tetrahydronaphthalene Following the procedures described in Step 5 of Example 1, omitting the final chromatographic purification and replacing 1-cyano-2-[1-(1,3-dioxolane)-2-phenylethyl]-6-methoxy-1,2,3,4-tetrahydronaphthalene with 1.57 g (4.2 mmol) of 1-cyano-2-[1-(1,3-dioxolane)-4-phenyl-butyl]-6-methoxy-1,2,3,4-tetrahydronaphthalene (the product of Step 3 of this Example), the title compound was prepared in 95% yield (1.5 g); MS DCl—NH$_3$ M/Z: 382 (M+H)$^+$; $^1$H NMR (CDCl$_3$) δ1.3–1.9 (7H, m), 2.05–2.21 (1H, m), 2.5–3 (6H, m), 3.77 (3H, s), 3.8–4.05 (4H, m), 6.6–6.7 (2H, m), 7.00–7.3 (6H, m).

Step 5:
2,3,3a,4,5,9b-Hexahydro-7-methoxy-3-(3-phenylpropyl)-1H-benz[e]isoindole A solution of 1.5 g (3.9 mmol) of 1-aminomethyl-2-[1-(1,3-dioxolane)-4-phenylbutyl]-6-methoxy-1,2,3,4-tetrahydronaphthalene (the product of Step 4 of this Example), in 30 mL of THF and 5 mL of 3N aqueous hydrochloric acid was stirred at ambient temperature for 1 h. At this time, according to TLC analysis, on silica gel plates eluted with 20:1:1 ethyl acetate:water:formic acid, the reaction had gone to completion. The solvent was evaporated in vacuo and residual water removed by azeotropic distillation with benzene. The residue was dissolved in 40 mL of methanol and 1 g of sodium cyanoborohydride was added to the resultant solution followed by a few crystals of bromocresol green indicator. The pH of the solution was adjusted with methanolic hydrogen chloride until the color of the solution changed from yellow to greenish blue. The solvent was removed in vacuo and the residue was dissolved in 2N aqueous hydrochloric acid in order to quench any excess sodium cyanoborohydride and the resultant aqueous solution was extracted with diethyl ether. The aqueous layer from the ether extraction was then extracted with methylene chloride. The ether extracts and the methylene chloride extracts were combined and concentrated to afford 0.67 g (54% yield) of the title compound as a mixture of the cis and trans isomers; MS DCl—NH$_3$ M/Z: 322 (M+H)$^+$.

Step 6:
cis-2,3,3a,4,5,9b-Hexahydro-7-methoxy-2-methyl-3-(3-phenylpropyl)-1H-benz[e]isoindole methanesulfonic acid salt Following the procedures described in Example 2, replacing the product of Example 1 with 350 mg (1.1 mmol) of 2,3,3a,4,5,9b-Hexahydro-7-methoxy-3-(3-phenylpropyl)-1H-benz[e]isoindole, the product of Step 5 of this Example, the title compound was prepared in 89% yield (301 mg), m.p. 129°–131° C.; MS DCl—NH$_3$ M/Z: 336 (M+H)$^+$; Analysis calculated for $C_{24}H_{33}NO_4S + H_2O$: C, 64.11; H, 7.85; N, 3.12. Found: C, 63.98; H, 7.36; N, 2.96.

EXAMPLE 31 cis-5,6-Dimethoxy-2,3,3a,4,5,9b-hexahydro-3-phenylmethyl-1H-benz[e]isoindole hydrochloride

Step 1:
1-Cyano-5,6-dimethoxy-2-[1-(1,3-dithiane)-2-phenylethyl]-1,2,3,4-tetrahydronaphthalene Following the procedures described in Step 3 of Example 1, replacing 1-cyano-6-methoxy-3,4-dihydronaphthalene with 15.72 g (75 mmol) of 1-cyano-5,6-dimethoxy-3,4-dihydronaphthalene (prepared as described by F. Z. Basha, et al. in *J. Organic Chemistry*, 50: 4160-2 (1985)), the title compound was prepared in 44% yield (14 g), m.p. 78°-80° C.; MS DCl—NH$_3$ M/Z: 440 (M+H)+; $^1$H NMR (CDCl$_3$) of cis isomer δ1.72-1.97 (2H, m), 1.97-2.15 (1H, m), 2.45-2.97 (7H, m), 3.13, 3.74 (2H, dd J=15 Hz), 3.15-3.28 (1H, m), 3.83 (3H, s), 3.89 (3H, s), 4.47 (1H, dd, J=4.6, 1.5 Hz), 6.83 (1H, d, J=9 Hz), 7.04 (1H, d, J=9 Hz), 7.12-7.45 (5H, m).

Step 2:
1-Cyano-5,6-dimethoxy-2-[1-(1,3-dioxolane)-2-phenylethyl]-1,2,3,4-tetrahydronaphthalene Following the procedures described in Step 4 of Example 1, replacing 1-cyano-2-[1-(13-dithiane)-2-phenylethyl]-6-methoxy-1,2,3,4-tetrahydronaphthalene with 13.5 g of 1-cyano-5,6-dimethoxy-2-[1-(1,3-dithiane)-2-phenylethyl]-1,2,3,4-tetrahydronaphthalene (the product of Step 1 of this Example), the title compound was prepared in 61% yield (7.3 g), m.p. 122°-125° C.; MS DCl—NH$_3$ M/Z: 380 (M+H)+, 397 (M+NH$_4$)+.

Step 3:
1-Aminomethyl-5,6-dimethoxy-2-[1-(1,3-dioxolane)-2-phenylethyl]-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 7.3 g (19.26 mmol) of 1-cyano-5,6-dimethoxy-2-[1-(1,3-dioxolane)-2-phenyl-ethyl]-1,2,3,4-tetrahydronaphthalene (the product of Step 2 of this Example), the title compound was prepared in 89% yield (6.5 g); MS DCl—NH$_3$ M/Z: 384 (M+H)+.

Step 4:
cis-6,7-Dimethoxy-2,3,3a,4,5,9b-hexahydro-3-phenylmethyl-1H-benz[e]isoindole hydrochloride Following the procedures described in Step 6 of Example 1, replacing 1-aminomethyl-2-[1-(1,3-dioxolane)-2-phenylethyl]-6-methoxy-1,2,3,4-tetrahydronaphthalene with 6.5 g (17 mmol) of 1-aminomethyl-5,6-dimethoxy-2-[1-(1,3-dioxolane)-2-phenylethyl]-1,2,3,4-tetrahydronaphthalene (the product of Step 3 of this Example), the title compound was prepared, m.p. 225°-226° C.; MS DCl—NH$_3$ M/Z: 324 (M+H)+; $^1$H NMR of the free amine (CDCl$_3$) d 1.4-1.57 (1H, m), 1.9-2.01 (1H, m), 2.15-2.25 (1H, m), 2.35-2.5 (1H, m), 2.78-3.17 (3H, m), 3.08-3.2 (1H, m), 3.28-3.48 (2H, m), 3.64-3.74 (1H, m), 3.8 (3H, s), 3.84 (3H, e), 6.73 (1H, d, J=9 Hz), 6.78 (1H, d, J=9 Hz), 7.17-7.34 (5H, m). Analysis calculated for $C_{21}H_{26}ClNO_2$: C, 70.08; H, 2.28; N, 3.89. Found: C, 69.94; H, 7.33; N, 3.88.

EXAMPLE 32 cis-6,7-Dimethoxy-2,3,3a,4,5,9b-hexahydro-2-methyl-3-phenylmethyl-1H-benz[e]isoindole hydrochloride Following the procedures described in Example 2, replacing the product of Example 1 with 2.1 g (6.5 mmol) of the product of Example 31, the title compound was prepared in 50% yield (1.2 g), m.p. 243°-244° C.; MS DCl—NH$_3$ M/Z: 338(M+H)+; $^1$H NMR (CDCl$_3$) δ1.5-1.68 (1H, m), 1.96-2.1 (3H, m), 2.43 (3H, s), 2.77-3.33 (7H, m), 3.76 (3H, s), 3.84 (3H, s), 6.73 (1H, d, J=9 Hz), 6.76 (1H, d, J=9 Hz), 7.16-7.36 (5H, m). Analysis calculated for $C_{22}H_{28}ClNO_2 + 0.5 H_2O$: C, 69.01; H, 7.63; N, 3.66. Found: C, 68.99; H, 7.52; N, 3.67.

EXAMPLE 33 trans-6,7-Dimethoxy-2,3,3a,4,5,9b-hexahydro-3-(3-methylphenyl)methyl-1H-benz[e]isoindole methanesulfonic acid salt

Step 1:
1-Cyano-5,6-dimethoxy-2-[1-(1,3-dithiane)-2-(3-methylphenyl)ethyl-1,2,3,4-tetrahydronaphthalene Following the procedures described in Step 3 of Example 1, replacing 2-phenylmethyl-1,3-dithiane with 2-(3-methylphenyl)methyl-1,3-dithiane (the product of Step 1 of Example 11) and 1-cyano-6-methoxy-3,4-dihydronaphthalene with 1-cyano-5,6-dimethoxy-3,4-dihydronaphthalene (the product of Step 1 of Example 31), the title compound was prepared.

Step 2:
1-Cyano-5,6-dimethoxy-2-(3-methylphenyl)methylcarbonyl-1,2,3,4-tetrahydronaphthalene Following the procedures described in Step 1 of Example 6, replacing 1-cyano-2-[1-(13-dithiane)-2-phenylethyl]-6-methoxy-1,2,3,4-tetrahydronaphthalene with 8 g (18.8 mmol) of 1-cyano-5,6-dimethoxy-2-[1-(1,3-dithiane)-2-(3-methylphenyl)ethyl]-1,2,3,4-tetrahydronaphthalene (the product of Step 1 of this Example), the title compound was prepared in 73% yield (4.7 g); MS DCl—NH$_3$ M/Z: 367 (M+NH$_4$)+; $^1$H NMR (CDCl$_3$) δ2.0-2.45 (2H, m), 2.35 (2H, s), 2.63-3.08 (4H, m), 3.8 (3H, s), 3.86 (3H, s), 4.08-4.15 (1H, m), 6.8 (1H, d, J=9 Hz), 6.9-7.28 (5H, m).

Step 3:
trans-6,7-Dimethoxy-2,3,3a,4,5,9b-hexahydro-3-(3-methylphenyl)methyl-1H-benz[e]isoindole methanesulfonic acid salt Following the procedures described in Step 2 of Example 6, replacing 1-cyano-6-methoxy-2-phenylmethylcarbonyl-1,2,3,4-tetrahydronaphthalene with 4.7 g (12.84 mmol) of 1-cyano-5,6-dimethoxy-2-(3-methylphenyl)methyl-carbonyl-1,2,3,4-tetrahydronaphthalene (the product of Step 2 of this Example), the title compound was prepared in 44% yield (0.45 g), m.p. 145°-146° C.; MS DCl—NH$_3$ M/Z: 324 (M+H)+; $^1$H NMR (CDCl$_3$) δ1.32-1.86 (3H, m), 2.3 (3H, s), 2.63-2.82 (1H, m), 2.88-3.3 (5H, m), 3.4-3.8 (2H, m), 3.8 (3H, s), 3.86 (3H, s), 6.58 (1H, d, J=9 Hz), 6.72 (1H, d, J=9 Hz), 7.0-7.22 (4H, m). Analysis calculated for $C_{23}H_{31}NO_5S + 0.25 H_2O$: C, 63.06; H, 7.25; N, 3.20. Found: C, 63.01; H, 7.17; N, 3.17.

EXAMPLE 34 trans-6,7-Dimethoxy-2,3,3a,4,5,9b-hexahydro-2-methyl-3-(3-methylphenyl)methyl-1H-benz[e]isoindole hydrochloride Following the procedures described in Example 7, replacing the product of Example 6 with 1.17 g (3.62 mmol) of the product of Example 33, the desired product was prepared and converted to the hydrochloride salt (the title compound), m.p. 100°-104° C.; MS DCl—NH$_3$ M/Z: 352 (M+H)$^+$. Analysis calculated for C$_{23}$H$_{30}$ClNO$_2$+H$_2$O: C, 68.05; H, 7.95; N, 3.45. Found: C, 64.47; H, 7.57; N, 3.34.

EXAMPLE 35 trans-2,3,3a,4,5,9b-Hexahydro-2-methyl-6,7-methylenedioxy-3-(3-methylphenyl)methyl-1H-benz[e]isoindole methanesulfonic acid salt

Step 1:
1-Cyano-2-[1-(1,3-dithiane)-2-(3-methylphenyl)ethyl]-5,6-methylenedioxy-1,2,3,4-tetrahydronaphthalene Following the procedures described in Step 2 of Example 17, replacing 2-(4-fluorophenyl)methyl-1,3-dithiane with 6.19 g (27.6 mmol) of 2-(3-methylphenyl)methyl-1,3-dithiane and 1-cyano-3,4-dihydronaphthalene with 5 g (25.1 mmol) of 1-cyano-5,6-methylenedioxy-3,4-dihydronaphthalene (prepared as described by F. Z. Basha, et al. in *J. Organic Chemistry*, 50: 4160-2 (1985)), the title compound was prepared in 77% yield (8.11 g); MS DCl—NH$_3$ M/Z: 424 (M+H)$^+$, 441 (M+NH$_4$)$^+$.

Step 2:
1-Cyano-5,6-methylenedioxy-2,3-(3-methylphenyl)methylcarbonyl-1,2,3,4-tetrahydronaphthalene Following the procedures described in Step 1 of Example 6, replacing 1-cyano-2-[1-(13-dithiane)-2-phenylethyl]-6-methoxy-1,2,3,4-tetrahydronaphthalene with 8.11 g (19.15 mmol) of 1-cyano-2-[1-(1,3-dithiane)-2-(3-methylphenyl)ethyl]-5,6-methylenedioxy-1,2,3,4-tetrahydronaphthalene from Step 1, the title compound was prepared in 69% yield (4.43 g); MS DCl—NH$_3$ M/Z: 351 (M+H)$^+$; $^1$H NMR (CDCl$_3$) δ2.04-2.22 (1H, m), 2.32-2.44 (1H, m), 2.35 (3H, s), 2.61-2.74 (1H, m), 2.87-2.98 (2H, m), 3.85 (2H, s), 4.11 (1H, d, J=4.5 Hz), 5.97 (2H, d, J=2 Hz, 8 Hz), 6.69 (1H, d, J=8 Hz), 6.77 (1H, d, J=8 Hz), 6.99-7.12 (3H, m), 7.23 (1H, t, J=8 Hz).

Step 3:
2,3,3a,4,5,9b-Hexahydro-6,7-methylenedioxy-3-(3-methylphenyl)methyl-1H-benz[e]isoindole methanesulfonic acid salt Following the procedures described in Step 2 of Example 6, replacing 1-cyano-6-methoxy-2-phenylmethylcarbonyl-1,2,3,4-tetrahydronaphthalene with 4.43 g (13.3 mmol) of 1-cyano-5,6-methylenedioxy-2-(3-methylphenyl)methyl-carbonyl-1,2,3,4-tetrahydronaphthalene (the product of Step 2 of this Example), the title compound was prepared in 90% yield (3.83 g), m.p. 163°-169° C.; MS DCl—NH$_3$ M/Z: 322 (M+H)$^+$; $^1$H NMR (CDCl$_3$) δ1.40-1.61 (2H,m), 1.82 (1H, bs), 1.91-2.01 (1H, m), 2.35 (3H, s), 2.58-2.97 (6H, m), 3.11-3.22 (1H, m), 3.46-3.54 (1H, m), 5.92 (2H, s), 6.42 (1H, dd, J=8 Hz, 2 Hz), 6.62 (1H, d, J=8 Hz), 7.0-7.10 (3H, m), 7.15-7.23 (1H, m). Analysis calculated for C$_{22}$H$_{27}$NO$_5$S+0.25H$_2$O: C, 62.61; H, 6.57; N, 3.32. Found: C, 62.62; H, 6.42; N, 3.25.

Step 4:
trans-2,3,3a,4,5,9b-Hexahydro-2-methyl-6,7-methylenedioxy-3-(3-methylphenyl)methyl-1H-benz[e]isoindole methanesulfonic acid salt Following the procedures described in Example 2, replacing the product of Example 1 with 2.27 g (7.07 mmol) of 2,3,3a,4,5,9b-hexahydro-6,7-methylenedioxy-3-(3-methylphenyl)methyl-1H-benz[e]isoindole from Step 3 of this Example, the title compound was prepared, m.p. 161.5-162.5° C.; MS DCl—NH$_3$ M/Z: 336 (M+H)$^+$; $^1$NMR (CDCl$_3$) δ1.23-1.78 (3H, m), 2.33 (3H, s), 2.47 (3H, s), 2.51-3.23 (8H, m), 5.90 (2H, s), 6.37 (1H, dd, J=2 Hz, 8 Hz), 6.61 (1H, d, J=8 Hz), 6.97-7.08 (3H, m), 7.17 (1H, t, J=8 Hz). Analysis calculated for C$_{23}$H$_{29}$NO$_5$: C, 64.02; H, 6.77; N, 3.25. Found: C, 63.73; H, 6.49; N, 3.21.

EXAMPLE 36 trans-3-(3-Fluorophenyl)methyl-2,3,3a,4,5,9b-hexahydro-2-methyl-6,7-methylenedioxy-1H-benz[e]isoindole methanesulfonic acid salt

Step 1:
1-Cyano-2-[1-(1,3-dithiane)-2-(3-fluorophenyl)ethyl]-5,6-methylenedioxy-1,2,3,4-tetrahydronaphthalene Following the procedures described in Step 3 of Example 1, replacing 1-cyano-6-methoxy-3,4-dihydronaphthalene with 6.7 g (33.6 mmol) of 1-cyano-5,6-methylenedioxy-3,4-dihydronaphthalene (prepared as described by F. Z. Basha, et al. in *J. Organic Chemistry*, 1985, 50: 4160-2 and 2-phenylmethyl-1,3-dithiane with 13 g (56.9 mmol) of 2-(4-fluorophenyl)methyl-1,3-dithiane, the title compound was prepared in 44% yield (6.3 g); MS DCl—NH$_3$ M/Z: 428 (M+H)$^+$.

Step 2:
1-Cyano-2-(3-fluorophenyl)methylcarbonyl-5,6-methylenedioxy-1,2,3,4-tetrahydronaphthalene Following the procedures described in Step 1 of Example 6, replacing 1-cyano-2-[1-(13-dithiane)-2-phenylethyl]-6-methoxy-1,2,3,4-tetrahydronaphthalene with 6.3 g (14.7 mmol) of 1-cyano-2-[1-(1,3-dithiane)-2-(3-fluorophenyl)ethyl]-5,6-methylenedioxy-1,2,3,4-tetrahydronaphthalene from Step 1, the title compound was prepared in 29% yield (1.43 g); MS DCl—NH$_3$ M/Z: 355 (M+H)+; $^1$H NMR of trans isomer (CDCl$_3$) δ2.08-2.25 (1H, m), 2.34-2.46 (1H, m), 2.63-2.78 (1H, m), 2.87-3.00 (2H, m), 3.91 (2H, s), 4.15 (1H, d, J=4 Hz), 5.97 (2H, dd, J=1 Hz, 6 Hz), 6.70 (1H, d, J=8 Hz), 6.78 (1H, d, J=8 Hz), 6.92-7.04 (3H, m), 7.27-7.37 (1H, m); $^1$H NMR of cis isomer (CDCl$_3$) δ1.70-1.86 (1H, m), 2.16-2.28 (1H, m), 2.63-3.04 (2H, m), 3.16-3.25 (1H, m), 3.92 (2H, d, J=3.5 Hz), 4.28 (1H, d, J=10 Hz), 5.93-5.99 (2H, m), 6.65-6.90 (2H, m), 6.88-7.06 (3H, m), 7.28-7.37 (1H, m).

Step 3:
3-(3-Fluorophenyl)methyl-2,3,3a,4,5,9b-hexahydro-6,7-methylenedioxy-1H-benz[e]isoindole methanesulfonic acid salt Following the procedures described in Step 2 of Example 6, replacing 1-cyano-6-methoxy-2-phenylmethylcarbonyl-1,2,3,4-tetrahydronaphthalene with 1.43 g (13.3 mmol) of 1-cyano-5,6-methylenedioxy-2-(3-methylphenyl)methyl-carbonyl-1,2,3,4-tetrahydronaphthalene (the product of Step 2 of this Example), the title compound was prepared in 30% yield (0.42 g); MS DCl—NH$_3$ M/Z: 326 (M+H)+.

Step 4: trans 3-(3-Fluorophenyl)methyl-2,3,3a,4,5,9b-hexahydro-2-methyl-6,7-methylenedioxy-1H-benz[e]isoindole methanesulfonic acid salt Following the procedures described in Example 2, replacing the product of Example 1 with 3-(3-fluorophenyl)methyl-2,3,3a,4,5,9b-hexahydro-6,7-methylenedioxy-1H-benz[e]isoindole from Step 3 of this Example, the title compound was prepared, m.p. 188°–189° C.; MS DCl—NH$_3$ M/Z: 340 (M+H)+; $^1$H NMR (CDCl$_3$) δ1.29–1.64 (2H, m), 1.68–1.80 (1H, m), 2.45 (3H, s), 2.51–2.95 (6H, m), 2.97–3.22 (2H, m), 5.90 (2H, s), 6.36 (1H, dd, J=2 Hz, 8 Hz), 6.60 (1H, d, J=8 Hz), 6.85–7.08 (3H, m), 7.18–7.28 (1H, m). Analysis calculated for C$_{22}$H$_{26}$FNO$_5$S: C, 60.67; H, 6.02; N, 3.22. Found: C, 60.39; H, 6.02; N, 3.17.

EXAMPLE 37 cis-2,3,3a,4,5,9b-Hexahydro-6-methoxy-9-methy-3-phenylmethyl-1H-benz[e]isoindole hydrochloride Step 1: 1-Cyano-5-methoxy-8-methyl-3,4-dihydronaphthalene Following the procedures described in Step 2 of Example 1, replacing 6-methoxy-α-tetralone with 5-methoxy-8-methyl-α-tetralone (prepared as described by F. Z. Basha, et al. in *J. Organic Chemistry*, 50: 4160-2 (1985)), the title compound was prepared.

Step 2: 1-Cyano-2-[1-(1,3-dithiane)-2-phenylethyl]-5-methoxy-8-methyl-1,2,3,4-tetrahydronaphthalene Following the procedures described in Step 2 of Example 17, replacing 1-cyano-6-methoxy-3,4-dihydronaphthalene with 8.2 g (41 mmol) of 1-cyano-5-methoxy-8-methyl-3,4-dihydronaphthalene (the product of Step 1 of this Example), the title compound was prepared in 74% yield (1.6 g), m.p. 200°–202° C.; MS DCl—NH$_3$ M/Z: 410 (M'H)+; $^1$H NMR (CDCl$_3$) δ1.72–2.2 (3H, m), 2.38 (3H, s), 2.43–2.95 (7H, m), 3.07–3.2 (1H, m), 3.16, 3.75 (2H, dd, J=15 Hz), 3.82 (3H, s), 4.5 (1H, dd, J=4.6 Hz, 1.5 Hz), 6.72 (1H, d, J=9 Hz), 7.04 (1H, d, J=9 Hz), 7.25–7.43 (5H, m).

Step 3: 1-Cyano-2-[1-(1,3-dioxolane)-2-phenylethyl]-5-methoxy-8-methyl-1,2,3,4-tetrahydronaphthalene Following the procedures described in Step 4 of Example 1, replacing 1-cyano-2-[1-(13-dithiane)-2-phenylethyl]-6-methoxy-1,2,3,4-tetrahydronaphthalene with 12.8 g (31.3 mmol) of 1-cyano-2-[1-(1,3-dithiane)-2-phenylethyl]-5-methoxy-8-methyl-1,2,3,4-tetrahydronaphthalene (the product of Step 2 of this Example), the title compound was prepared in 62.5% yield (7.1 g); MS DCl—NH$_3$ M/Z: 364 (M+H)+; $^1$H NMR (CDCl$_3$) δ1.97–2.28 (3H, m), 2.32 (3H, s), 2.42–2.62 (1H, m), 2.94–3.07 (1H, m), 3.0, 3.13 (2H, dd, J=15 Hz), 3.6–4.18 (5H, m), 3.8 (3H,s), 6.67 (1H, d, J=9 Hz), 7.0 (1H, d, J=9 Hz), 7.17–7.35 (5H, m).

Step 4: 1-Aminomethyl-2-[1-(1,3-dioxolane)-2-phenylethyl]-5-methoxy-8-methyl-1,2,3,4-tetrahydronaphthalene Following the procedures described in Step 5 of Example 1, replacing 1-cyano-2-[1-(1,3-dioxolane)-2-phenylethyl]-6-methoxy-1,2,3,4-tetrahydronaphthalene with 6.9 g (19 mmol) of 1-cyano-2-[1-(1,3-dioxolane)-2-phenylethyl]-5-methoxy-8-methyl-1,2,3,4-tetrahydronaphthalene (the product of Step 3 of this Example), the title compound was prepared in 52% yield (3.6 g), m.p. 134°–136° C.; MS CDl—NH$_3$ M/Z: 368 (M+H)+.

Step 5: cis-2,3,3a,4,5,9b-Hexahydro-6-methoxy-9-methyl-3-phenylmethyl-1H-benz[e]isoindole hydrochloride Following the procedures described in Step 6 of Example 1, replacing 1-aminomethyl-2-[1-(1,3-dioxolane)-2-phenylethyl]-6-methoxy-1,2,3,4-tetrahydronaphthalene with 1.8 g (5.1 mmol) of 1-aminomethyl-2-[1-(1,3-dioxolane)-2-phenylethyl]-5-methoxy-8-methyl-1,2,3,4-tetrahydronaphthalene (the product of Step 4 of this Example), the title compound was prepared in 62% yield (1.1 g), m.p. 240°–242° C.; MS DCl—NH$_3$ M/Z: 308 (M+H)+; $^1$H NMR (CDCl$_3$) δ1.48–1.56 (1H, m), 1.9–2.45 (3H, m), 2.24 (3H, s), 2.74–3.15 (4H, m), 3.3–3.72 (3H, m), 3.8 (3H, s), 6,62 (1H, d, J=9 Hz), 6.95 (1H, d, J=9 Hz), 7.18–7.4 (5H, m). Analysis calculated for C$_{21}$H$_{26}$ClNO+0.25H$_2$O: C, 72.40; H, 7.67; N, 4.02. Found: C, 72.53; H, 7.52; N, 4.09.

EXAMPLE 38 cis-2,9-Dimethyl-2,3,3a,4,5,9b-hexahydro-6-methoxy-3-phenylmethyl-1H-benz[e]isoindole hydrochloride Following the procedures described in Example 2, replacing the product of Example 1 with 0.6 g (1.75 mmol) of the product of Example 37, the title compound was prepared in 65% yield (0.4 g), m.p. 183°–185° C.; MS DCl—NH$_3$ M/Z: 322 (M+H)+; $^1$H NMR of free base (CDCl$_3$) δ1.5–1.82 (2H, m), 1.98–2.32 (2H, m), 2.18 (3H, s), 6.6 (1H, d, J=9 Hz), 6.93 (1H, d, J=9 Hz), 7.17–7.35 (5H, m). Analysis calculated for C$_{22}$H$_{28}$ClNO+0.5H$_2$O: C, 72.01; H, 7.69; N, 3.82. Found: C, 71.98; H, 7.83; N, 3.85.

EXAMPLE 39 cis-2-Ethyl-9-(4-(4-fluorophenyl)butyloxy)-2,3,3a,4,5,9b-hexahydro-6-methoxy-3-phenylmethyl-1H-benz[e]isoindole methanesulfonic acid salt Step 1: 1-Cyano-2-[1-(1,3-dithiane)-2-phenylethyl]-8-(4-(4-fluorophenyl)-1-n-butoxy)-5-methoxy-1,2,3,4-tetrahydronaphthalene Following the procedures described in Step 2 of Example 17, replacing 1-cyano-3,4-dihydronaphthalene with 4.3 g (12.2 mmol) of 1-cyano-8-(4-(4-fluorophenyl)-1-n-butyoxy)-5-methoxy-3,4-dihydronaphthalene and 2-(4-fluorophenyl)methyl-1,3-dithiane with 2.7 g (12.8 mmol) of 2-phenylmethyl-1,3-dithiane, (the product of Step 1 of Example 1), the title compound was prepared in 73% yield (5 g); MS DCl—NH$_3$ M/Z: 562 (M+H)+; $^1$H NMR (CDCl$_3$) δ1.8–1.95 (5H, m), 2.0–2.12 (1H, m), 2.4–2.75 (10H, m), 2.83–2.93 (1H, m), 3.08–3.2 (2H, m), 3.78 (3H, s), 3.9–4.0 (1H, m), 4.05–4.13 (1H, m), 4.68–4.75 (1H, m), 6.65–6.75 (2H, m), 7.2–7.35 (7H, m), 7.38–7.45 (2H, m).

Step 2:
1-Cyano-2-[1-(1,3-dioxolane)-2-phenylethyl]-8-(4-(4-fluorophenyl)-1-n-butoxy)-5-methoxy-1,2,3,4-tetrahydronaphthalene Following the procedures described in Step 4 of Example 1, replacing 1-cyano-2-[1-(1,3-dithiane)-2-phenylethyl]-6-methoxy-1,2,3,4-tetrahydronaphthalene with 5.0 g (8.9 mmol) of 1-cyano-2-[1-(1,3-dithiane)-2-phenylethyl]-8-(4-(4-fluorophenyl)-1-n-butoxy)-5-methoxy-1,2,3,4-tetrahydronaphthalene, from Step 1, the title compound was prepared 44% yield (2.0 g) as a clear colorless oil; MS DCl—NH$_3$ M/Z: 516 (M+H)+; $^1$H NMR (CDCl$_3$) δ0.85–0.93 (1H, m), 1.23–1.32 (1H, m), 1.8–1.9 (3H, m), 1.92–2.0 (1H, m), 2.13–2.25 (1H, m), 2.43–2.58 (1H, m), 2.65–2.75 (2H, m), 2.95–3.15 (3H, m), 3.63–3.73 (1H, m), 3.68 (3H, s), 3.85–4.2 (5H, m), 4.27–4.32 (1H, m), 6.6–6.7 (2H, m), 7.15–7.33 (9H, m).

Step 3:
1-Aminomethyl-2-[1-(1,3-dioxolane)-2-phenylethyl]-8-(4-(4-fluorophenyl)-1-n-butoxy)-5-methoxy-1,2,3,4-tetrahydronaphthalene Following the procedures described in Step 5 of Example 1, replacing 1-cyano-6-methoxy-2-[1-(1,3-dioxolane)-2-phenylethyl]-1,2,3,4-tetrahydronaphthalene with 1.1 g (2.1 mmol) of 1-cyano-2-[1-(1,3-dioxolane)-2-phenylethyl]-8-(4-(4-fluorophenyl)-1-n-butoxy)-5-methoxy-1,2,3,4-tetrahydronaphthalene, from Step 2, the title compound was prepared; MS DCl—NH$_3$ M/Z: 520 (M+H)+; $^1$H NMR (CDCl$_3$) δ1.75–1.9 (4H, m), 1.92–2.05 (1H, m), 2.63–2.73 (2H, m), 2.81–2.95 (3H, m), 3.15–3.7 (10H, m), 3.75 (1H, s), 3.78 (3H, s), 3.95–4.02 (1H, m), 6.6–6.65 (2H, m), 7.1–7.28 (8H, m), 7.3–7.4 (1H, m).

Step 4:
9-(4-(4-Fluorophenyl)-1-n-butoxy)-2,3,3a,4,5,9b-hexahydro-6-methoxy-3-phenylmethyl-1H-benz[e]isoindole hydrochloride Following the procedures described in Step 6 of Example 1, replacing 1-aminomethyl-6-methoxy-2-[1-(1,3-dioxolane)-2-phenylethyl]-1,2,3,4-tetrahydronaphthalene with 1.25 g (2.3 mmol) of 1-aminomethyl-2-[1-(1,3-dioxolane)-2-phenylethyl]-8-(4-(4-fluorophenyl)-1-n-butoxy)-5-methoxy-1,2,3,4-tetrahydronaphthalene, from Step 3, the title compound was prepared in 85% yield (0.9 g); MS DCl—NH$_3$ M/Z: 460 (M+H)+; $^1$H NMR (CDCl$_3$) δ1.55–1.68 (4H, m), 1.7–1.98 (5H, m), 2.0–2.15 (1H, m), 2.25–2.4 (1H, m), 2.62–3.12 (4H, m), 3.35–3.48 (1H, m), 3.55–3.65 (2H, m), 3.78 (3H, s), 3.82–3.95 (2H, m), 6.53–6.62 (2H, m), 7.13–7.33 (9H, m).

Step 5:
cis-2-Ethyl-9-(4-(4-fluorophenyl)butyloxy)-2,3,3a,4,5,9b-hexahydro-6-methoxy-3-phenylmethyl-1H-benz[e]isoindole methanesulfonic acid salt Following the procedures described in Example 3, replacing the product of Example 1 with 0.90 g (2.0 mmol) of 9-(4-(4-fluorophenyl)-1-n-butoxy)-2,3,3a,4,5,9b-hexahydro-6-methoxy-3-phenylmethyl-1H-benz[e]isoindole hydrochloride, from Step 4, the title compound was prepared as white needle-like crystals, m.p. 145°–146° C.; MS DCl—NH$_3$ M/Z: 488 (M+H)+; $^1$H NMR (CDCl$_3$) δ1.25 (3H, t, J=8 Hz), 1.72–1.85 (5H, m), 2.0–2.4 (3H, m), 2.62–2.83 (2H, m), 2.78 (3H, s), 3.08–3.73 (8H, m), 3.75 (3H, s), 6.56 (1H, d, J=9 Hz), 6.65 (1H, d, J=9 Hz), 7.1–7.4 (9H, m). Analysis calculated for C$_{33}$H$_{42}$FNO$_5$S: C, 67.90; H, 7.25; N, 2.40. Found: C, 68.34; H, 7.39; N, 2.35.

EXAMPLE 40
trans-3-(3-Fluorophenyl)methyl-2,3,3a,4,5,9b-hexahydro-2-methyl-6,7,8-trimethoxy-1H-benz[e]isoindole hydrochloride

Step 1:
1-Cyano-2-[1-(13-dithiane)-2-(3-fluorophenyl)ethyl]-5,6,7-trimethoxy-1,2,3,4-tetrahydronaphthalene Following the procedures described in Step 3 of Example 1, replacing 1-cyano-6-methoxy-3,4-dihydronaphthalene with 9 g (36.73 mmol) of 1-cyano-5,6,7-trimethoxy-3,4-dihydronaphthalene (prepared as described by F. Z. Basha, et al. in *J. Organic Chemistry*, 50: 4160–2 (1985)), the title compound was prepared in 29% yield (6.5 g), m.p. 65°–67° C.; MS DCl—NH$_3$ M/Z: 474 (M+H)+; $^1$H NMR (CDCl$_3$) δ1.68–1.82 (2H, m), 2.18–2.30 (1H, m), 2.55–2.88 (4H, m), 3.13–3.26 (1H, m), 3.85 (6H, s), 3.88 (3H, s), 3.89–4.0 (5H, m), 4.32 (1H, d, J=9 Hz), 6.72 (1H, s), 6.92–7.08 (3H, m), 7.28–7.4 (1H, m).

Step 2:
1-Cyano-2-(3-fluorophenyl)methylcarbonyl-5,6,7-trimethoxy-1,2,3,4-tetrahydronaphthalene Following the procedures described in Step 1 of Example 6, replacing 1-cyano-2-[1-(13-dithiane)-2-phenylethyl]-6-methoxy-1,2,3,4-tetrahydronaphthalene with 6.5 g (13.7 mmol) of 1-cyano-2-[1-(13-dithiane)-2-(3-fluorophenyl)ethyl]-5,6,7-trimethoxy-1,2,3,4-tetrahydronaphthalene (the product of Step 1 of this Example), the title compound was prepared in 45% yield, m.p. 120°–122° C.

Step 3:
trans-3-(3-Fluorophenyl)methyl-2,3,3a,4,5,9b-hexahydro-6,7,8-trimethoxy-1H-benz[e]isoindole Following the procedures described in Step 2 of Example 6, replacing 1-cyano-6-methoxy-2-phenylmethylcarbonyl-1,2,3,4-tetrahydronaphthalene with 0.94 g (2.46 mmol) of 1-cyano-2-(3-fluorophenyl)methylcarbonyl-5,6,7-trimethoxy-1,2,3,4-tetrahydronaphthalene (the product of Step 2 of this Example) the title compound was prepared in 49% yield (0.45 g); MS DCl—NH$_3$ M/Z: 372 (M+H)+; $^1$H NMR (CDCl$_3$) δ1.33–1.6 (2H, m), 1.82–1.95 (1H, m), 2.6–3.0 (7H, m), 3.13–3.28 (1H, m), 3.52–3.62 (1H, m), 3.8 (3H, s), 3.82 (3H, s), 3.85 (3H, s), 6.28 (1H, s), 6.82–7.1 (3H, m), 7.2–7.3 (1H, m).

Step 4:
trans-3-(3-Fluorophenyl)-methyl-2,3,3a,4,5,9b-hexahydro-2-methyl-6,7,8-trimethoxy-1H-benz[e]isoindole hydrochloride Following the procedures described in Example 7, replacing the product of Example 6 with 0.8 g (2.16 mmol) of the product of Step 4 of this Example, the title compound was prepared in 60% yield (0.53 g), m.p. 241°–242° C.; MS DCl—NH$_3$ M/Z: 386 (M+H)+. Analysis calculated for C$_{23}$H$_{29}$ClFNO$_3$+0.5H$_2$O: C, 64.10; H, 7.02; N, 3.25. Found: C, 64.49; H, 6.83; N, 3.21.

EXAMPLE 41

3-(3-Fluorophenyl)methyl-2,3,3a,4,5,9b-hexahydro-2-methyl-6,7,9-trimethoxy-1H-benz[e]isoindole hydrochloride Step 1:

1-Cyano-2-[1-(13-dithiane)-2-(3-fluorophenyl)ethyl]-5,6,8-trimethoxy-1,2,3,4-tetrahydronaphthalene Following the procedures described in Step 3 of Example 1, replacing 1-cyano-6-methoxy-3,4-dihydronaphthalene with 8.3 g (33.9 mmol) of 1-cyano-5,6,8-trimethoxy-3,4-dihydronaphthalene (prepared as described by F. Z. Basha, et al. in *J. Organic Chemistry*, 50: 4160–2 (1985)), the title compound was prepared in 27% yield (4.4 g); MS DCl—$NH_3$ M/Z 474 (M+H)$^+$, $^1$H NMR ($CDCl_3$) δ1.7–2.1 (3H, m), 2.38–2.8 (7H, m), 2.88–3.28 (3H, m), 3.78 (3H, s), 3.88 (3H, s), 3.92 (3H, s), 4.57–4.63 (1H, m), 6.42 (1H, s), 6.9–7.12 (1H, m), 7.13–7.3 (3H, m).

Step 2:

1-Cyano-2-(3-fluorophenyl)methylcarbonyl-5,6,8-trimethoxy-1,2,3,4-tetrahydronaphthalene Following the procedures described in Step 1 of Example 6, replacing 1-cyano-2-[1-(13-dithiane)-2-phenylethyl]-6-methoxy-1,2,3,4-tetrahydronaphthalene with 4.4 g (9.3 mmol) of 1-cyano-2-[1-(13-dithiane)-2-(3-fluorophenyl)ethyl]-5,6,8-trimethoxy-1,2,3,4-tetrahydronaphthalene (the product of Step 1 of this Example), the title compound was prepared in 61% yield (2.3 g), m.p. 58°–62° C.; MS DCl—$NH_3$ M/Z: 401 (M+$NH_4$)$^+$; $^1$H NMR ($CDCl_3$) δ1.95–2.12 (1H, m), 2.33–3.48 (1H, m), 2.33–2.48 (1H, m), 2.6–2.8 (2H, m), 3.08–3.2 (1H, m), 3.75 (3H, s), 3.88 (6H, s), 3.93 (2H, d, J=1.5 Hz), 4.38 (1H, dd, J=1.5 Hz, 4.5 Hz), 6.4 (1H, s), 6.93–7.2 (3H, m), 7.28–7.38 (1H, m).

Step 3:

3-(3-Fluorophenyl)methyl-2,3,3a,4,5,9b-hexahydro-6,7,9-trimethoxy-1H-benz[e]isoindole hydrochloride Following the procedures described in Step 2 of Example 6, replacing 1-cyano-6-methoxy-2-phenylmethylcarbonyl-1,2,3,4-tetrahydronaphthalene with 2.3 g (6 mmol) of 1-cyano-2-(3-fluorophenyl)methylcarbonyl-5,6,8-trimethoxy-1,2,3,4-tetrahydronaphthalene (the product of Step 2 of this Example) the title compound was prepared in 55% yield (1.25 g) as the free amine and then converted to the hydrochloride salt, m.p. 135°–138° C.; MS DCl—$NH_3$ M/Z: 372 (M+H)$^+$. Analysis calculated for $C_{22}H_{26}ClFNO_3 + H_2O$: C, 62.19; H, 6.59; N, 3.30. Found: C, 62.29; H, 6.93; N, 3.21.

Step 4:

3-(3-Fluorophenyl)-methyl-2,3,3a,4,5,9b-hexahydro-2-methyl-6,7,9-trimethoxy-1H-benz[e]isoindole hydrochloride Following the procedures described in Example 7, replacing the product of Example 6 with 0.52 g (1.36 mmol) of the product of Step 3 of this Example, the title compound was prepared in 58% yield (0.3 g), m.p. 195°–200° C.; MS DCl—$NH_3$ M/Z: 386 (M+H)$^+$. Analysis calculated for $C_{23}H_{29}ClFNO_3 + 1.5H_2O$: C, 61.53; H, 7.18; N, 3.12. Found: C, 61.91; H, 6.66; N, 3.06.

EXAMPLE 42

6,7-Dimethoxy-9-fluoro-3-(3-fluorophenyl)methyl-2,3,3a,4,5,9b-hexahydro-2-methyl-1H-benz[e]isoindole hydrochloride Step 1: 1-Cyano-5,6-dimethoxy-3,4-dihydronaphthalene Following the procedures described in Step 2 of Example 1, replacing 6-methoxy-α-tetralone with 5,6-dimethoxy-8-fluoro-α-tetralone, the title compound was prepared. 5,6-Dimethoxy-8-fluoro-α-tetralone was prepared as described by J. F. DeBernardis and F. Z. Basha in Example Number 62 through Example Number 67 in U.S. Pat. No. 4,634,705, (issued Jan. 6, 1987).

Step 2:

1-Cyano-5,6-dimethoxy-2-[1-(1,3-dithiane)-2-(3-fluorophenyl)ethyl]-8-fluoro-1,2,3,4-tetrahydronaphthalene Following the procedures described in Step 3 of Example 1, replacing 1-cyano-6-methoxy-3,4-dihydronaphthalene with 13.4 g (57.5 mmol) of 1-cyano-8-fluoro-5,6-dimethoxy-3,4-dihydronaphthalene (the product of Step 1 of this Example), and replacing 2-phenylmethyl-1,3-dithiane with 15.73 g (69 mmol) of 2-(3-fluorophenyl)methyl-1,3-dithiane (the product of Step 1 of Example 15), the title compound was prepared in 18% yield; MS DCl—$NH_3$ M/Z: 462 (M+H)$^+$; $^1$H NMR ($CDCl_3$) d 172–2.12 (3H, m), 2.4–3.04 (7H, m), 3.07, 3.74 (2H, dd, J=15 Hz), 3.17–3.2 (1H, m), 3.8 (3H, s), 3.85 (3H, s), 4.6 (1H, dd. J=4.5 Hz, 1.5 Hz), 6.6 (1H, t, J=9 Hz), 6.9–7.3 (4H, m).

Step 3:

1-Cyano-5,6-dimethoxy-8-fluoro-2-(3-fluorophenyl)methylcarbonyl-1,2,3,4-tetrahydronaphthalene Following the procedures described in Step 1 of Example 6, replacing 1-cyano-2-[1-(13-dithiane)-2-phenylethyl]-6-methoxy-1,2,3,4-tetrahydronaphthalene with 5.5 g (11.8 mmol) of 1-cyano-5,6-dimethoxy-2-[1-(13-dithiane)-2-(3-fluorophenyl)ethyl]-8-fluoro-1,2,3,4-tetrahydronaphthalene (the product of Step 2 of this Example), the title compound was prepared in 36% yield (1.36 g); MS DCl—$NH_3$ M/Z: 389 (M+$NH_4$)$^+$.

Step 4:

6,7-Dimethoxy-9-fluoro-3-(3-fluorophenyl)methyl-2,3,3a,4,5,9b-hexahydro-1H-benz[e]isoindole Following the procedures described in Step 2 of Example 6, replacing 1-cyano-6-methoxy-2-phenylmethylcarbonyl-1,2,3,4-tetrahydronaphthalene with 1.36 g (3.67 mmol) of 1-cyano-5,6-dimethoxy-8-fluoro-2-(3-fluorophenyl)methylcarbonyl-1,2,3,4-tetrahydronaphthalene (the product of Step 3 of this Example) the title compound was prepared in 30% yield (0.42 g); MS DCl—$NH_3$ M/Z: 360 (M+H)$^+$.

Step 5:

6,7-Dimethoxy-9-fluoro-3-(3-fluorophenyl)methyl-2,3,3a,4,5,9b-hexahydro-2-methyl-1H-benz[e]isoindole hydrochloride Following the procedures described in Example 7, replacing the product of Example 6 with 0.39 g (1.09 mmol) of the product of Step 4 of this Example, the title compound was prepared; MS DCl—$NH_3$ M/Z: 374 (M+H)$^+$. Analysis calculated for $C_{22}H_{26}ClF_2NO_2$: C, 64.46; H, 6.39; N, 3.42. Found: C, 64.01; H, 6.51; N, 3.36.

EXAMPLE 43 cis-7-Bromo-2,3,3a,4,5,9b-hexahydro-3-phenylmethyl-1H-benz[e]isoindole methanesulfonic acid salt

Step 1:
7-Bromo-1-cyano-2-[1-(1,3-dithiane)-2-phenylethyl]-1,2,3,4-tetrahydronaphthalene To a solution of 10.2 g (42.3 mmol) of 2-phenylmethyl-1,3-dithiane (from Step 1 of Example 1) in 100 mL of anhydrous THF at 0° C. under nitrogen atmosphere, was added 17 mL of a 1.5M solution of n-butyl lithium (42.3 mmol) in hexane. The reaction mixture was stirred for approximately 1 h and 15 min at 0° C. and then was cooled to −78° C. The solution of 2-benzyl-2-lithio-1,3-dithiane was then added, dropwise over a 15 min period, to a solution of 9 g (38.4 mmol) of 6-bromo-1-cyano-3,4-dihydronaphthalene (prepared as described by F. Z. Basha, et al. in *J Organic Chemistry*, 50: 4160–2 (1985)) in 100 mL of THF, at −78° C. The reaction mixture was allowed to warm to ambient temperature, was stirred at ambient temperature, under nitrogen for 2.5 h, and then was cooled to −78° C. and quenched by the addition of 50 mL of saturated aqueous ammonium chloride solution. The layers were separated and the aqueous layer extracted with two portions of ethyl acetate. The combined organic layer was washed with brine, dried over anhydrous magnesium sulfate, filtered and concentrated in vacuo. The resultant oil was triturated with diethyl ether/hexane and the solid purified by chromatography on silica gel eluted with 8:1 hexane:ethyl acetate to afford 15.46 g (90% yield) of the compound; MS DCl—$NH_3$ M/Z: 444, 446(M+H)+;$^1$H NMR ($CDCl_3$) δ1.62–1.99 (2H, m), 2.05–2.19 (1H, m), 2.49–3.18 (9H, m), 3.71 (1H, d), 4.38–4.48 (1H, m), 7.07–7.45 (8H, m).

Step 2:
1-Aminomethyl-6-bromo-2-[1-(1,3-dithiane)-2-phenylethyl]-1,2,3,4-tetrahydronaphthalene 6-Bromo-1-cyano-2-[1-(1,3-dithiane)-2-phenylethyl]-1,2,3,4-tetrahydronaphthalene 1 g (2.25 mmol), from Step 1, was dissolved in 10 mL of anhydrous THF. To the resultant solution at ambient temperature, was added 2.3 mL (2.3 mmol, 1 equivalent) of a 1.0M solution of borane in THF and the reaction mixture was heated at reflux temperature for 5 h. The reaction mixture was concentrated in vacuo and the residue was dissolved in methanol. Methanol saturated with anhydrous hydrogen chloride was added and the reaction mixture heated at reflux temperature overnight. The solvent was removed under reduced pressure and the residue partitioned between 15% potassium hydroxide and methylene chloride (1:4). The resultant layers were separated and the aqueous layer was extracted with two portions of methylene chloride. The combined methylene chloride extracts were dried over anhydrous magnesium sulfate, filtered and adsorbed onto silica gel. The silica gel was loaded on a silica gel column and eluted with ethyl acetate:formic acid:water (25:1:1 v/v/v) to give 650 mg (64% yield) of the desired product as the formic acid salt; MS DCl—$NH_3$ M/Z: 448, 450 (M+H)+; $^1$H NMR ($CDCl_3$) δ1.84–2.32 (5H, m), 2.68–3.02 (6H, m), 3.29–3.51 (3H, m), 3.47 (1H, d), 3.94 (1H, d), 6.96 (1H, d), 7.15–7.33 (7H, m).

Step 3:
1-(N-Acetyl)aminomethyl-6-bromo-2-[1-(1,3-dithiane)-2-phenylethyl]-1,2,3,4-tetrahydronaphthalene 1-Aminomethyl-6-bromo-2-[1-(1,3-dithiane)-2-phenylethyl]-1,2,3,4-tetrahydronaphthalene (6.15 g (13.7 mmol) from Step 2 was dissolved in 20 mL of pyridine and acetic anhydride (1.9 mL, 20.6 mmol) was added to the resultant solution, under a nitrogen atmosphere. The reaction mixture was heated for approximately 1 h at 50° C. The reaction mixture was allowed to cool to ambient temperature and it was stirred at ambient temperature for 0.5 h and then poured on to a slurry of ice and concentrated hydrochloric acid. The resultant aqueous mixture was extracted with three portions of methylene chloride and the combined organic layers were dried over anhydrous magnesium sulfate, filtered and concentrated in vacuo to give 5.73 g (85% yield) of the title compound; MS DCl—$NH_3$ M/Z: 490, 492 (M+H)+.

Step 4:
1-(N-Acetyl)aminomethyl-6-bromo-2-phenylmethylcarbonyl-1,2,3,4-tetrahydronaphthalene N-Bromosuccinimide (NBS; 16.6 g (93.5 mmol) was dissolved in 500 mL of 97:3 acetone:water and the resultant mixture was cooled to 0° C. 1-(N-acetyl)aminomethyl-6-bromo-2-[1-(1,3-dithiane)-2-phenylethyl]-1,2,3,4-tetrahydronaphthalene (5.73 g, 11.68 mmol) from Step 3 was dissolved in 100 mL of 97:3 acetone:water and the resultant solution was added to the NBS solution over a 10 min period. The reaction mixture was stirred at 0° C. for 10 min and then poured onto a slurry of ice and sodium sulfite. The resultant phases were separated. The organic layer was concentrated under reduced pressure and the residue dissolved in water. The solid phase was dissolved in water and combined with the aqueous solution of the residue from the organic phase. The combined aqueous solution was extracted with three portions of methylene chloride. The combined organic extracts were dried over anhydrous magnesium sulfate, filtered and concentrated under reduced pressure to afford the title compound, which was carried on to the next step without purification; MS DCl—$NH_3$ M/Z: 400, 402 (M+H)+, 417, 419 (M+$NH_4$)+.

Step 5:
cis-7-Bromo-2,3,3a,4,5,9b-hexahydro-3-phenylmethyl-1H-benz[e]isoindole methanesulfonic acid salt 1-(N-Acetyl)-aminomethyl-6-bromo-2-phenylmethylcarbonyl-1,2,3,4-tetrahydronaphthalene from Step 4 was dissolved in 100 mL of THF and 200 mL of 6N aqueous hydrochloric acid solution was added to the resultant solution. The reaction mixture was heated at reflux temperature overnight and then concentrated under reduced pressure to 30 mL, The aqueous concentrate was dissolved in 300 mL of methanol and 2.14 g (34 mmol) of sodium cyanoborohydride in 50 mL of methanol was added, dropwise, over a 10 minute period. The reaction mixture was stirred at ambient temperature for 1 h and then concentrated in vacuo. The residue was dissolved in water and the solution was made basic by the addition of concentrated aqueous sodium hydroxide solution. The aqueous solution was extracted with three portions of methylene chloride and the combined organic layers were dried over anhydrous magnesium sulfate, filtered and concentrated in vacuo.

The concentrated solution was adsorbed onto silica gel. The dried silica gel was loaded onto a silica gel column and eluted with ethyl acetate:formic acid:water (18:1:1) to give 1.7 g (40% yield) of the formic acid salt of the desired product. The formic acid salt was converted to the methanesulfonic acid salt via the free amine to give the title compound, m.p. 134.5°–135° C.; MS DCl—NH$_3$ M/Z: 442, 444 (M+H)$^+$; $^1$H NMR (CDCl$_3$) δ1.42–1.60 (1H, m), 2.02–2.13 (1H, m), 2.56–2.71 (1H, m), 2.68 (3H, m), 2.71–2.88 (1H, m), 2.88–3.10 (4H, m), 3.24 (1H, dd), 3.60–3.80 (2H, m), 4.10–4.20 (1H, m), 7.06 (1H, d), 7.27–7.44 (7H, m). Analysis calculated for C$_{20}$H$_{24}$BrNO$_3$S: C, 54.80; H, 5.52; N, 3.20. Found: C, 54.54; H, 5.49; N, 3.14.

EXAMPLE 44 cis-7-Bromo-2,3,3a,4,5,9b-hexahydro-2-methyl-3-phenylmethyl-1H-benz[e]isoindole methanesulfonic acid salt Ethyl formate (8 mL) was added to a solution of 7-bromo-2,3,3a,4,5,9b-hexahydro-3-phenylmethyl-1H-benz[e]isoindole, from Example 43, in 30 mL of toluene. The reaction mixture was heated at reflux temperature under a nitrogen atmosphere for 3 h. The solvent and excess ethyl formate were evaporated in vacuo and the residue was dissolved in 30 mL of dry THF under a nitrogen atmosphere. Borane (5 mL of a 1.00M solution in THF) was added and the reaction mixture was heated at reflux temperature for 1.5 h. Methanol saturated with anhydrous hydrogen chloride was added to the reaction mixture and the reflux was continued for 5 h. The reaction mixture was then allowed to cool to ambient temperature and was stirred at ambient temperature for approximately 64 h. The solvents were removed in vacuo and the residue was made basic by the addition of 1N aqueous sodium hydroxide solution and the resultant aqueous mixture was extracted with three portions of methylene chloride. The combined organic extract was dried over anhydrous magnesium sulfate, filtered and concentrated in vacuo. The residue was purified on silica gel eluted with ethyl acetate:water:formic acid (18:1:1 v/v/v) to give 630 mg (76% yield) of the title compound; MS DCl—NH$_3$ M/Z: 356, 358 (M+H)$^+$; $^1$H NMR (CDCl$_3$) δ1.81–2.01 (2H, m), 2.45–2.57 (1H, m), 2.61–2.74 (1H, m), 2.80 (3H, s), 2.83, 2.85 (2 s, N—CH$_3$), 2.88–2.97 (1H, m), 3.19–3.39 (3H, m), 3.51–3.72 (3H, m), 3.92–4.04 (1H, m), 6.86 (1H, d), 7.23–7.41 (7H, m). Analysis calculated for C$_{21}$H$_{26}$BrNO$_3$S: C, 55.75; H, 5.79; N, 3.10. Found: C, 55.51; H, 5.86; N, 3.04.

EXAMPLE 45 cis-3-(2-Chloro-5-N-ethyl-N-methylaminophenyl)methyl-2,3,3a,4,5,9b-hexahydro-2-methyl-1H-benz[e]isoindole hydrochloride Step 1: 2-(3-Nitrophenyl)-1-nitro-2-ethene A mixture of 30.22 g (200 mmol) of 3-nitrobenzaldehyde, 14 g of ammonium acetate and 25 mL of nitromethane in 230 mL of glacial acetic acid was heated at reflux temperature for 3 h and then poured onto ice. The resultant aqueous mixture was made basic by the addition of 45% aqueous potassium hydroxide solution. The precipitate was filtered and crystallized from ethyl acetate/hexane to give 14 g (43% yield) of the title compound; MS DCl—NH$_3$ M/Z: 165 (M+H)$^+$; $^1$H NMR (CDCl$_3$) δ7.7 (2H, dd, J=15 Hz), 7.88 (1H, d), 8.06 (1H, d), 8.37 (1H, d, J=15 Hz), 8.42 (1H, d).

Step 2: 2-(3-Nitrophenyl)-1-nitroethane

A solution of 14 g (72 mmol) of 2-(3-nitrophenyl)-1-nitro-2-ethene, from Step 1, in 200 mL of dioxane was added dropwise to a stirred suspension of 6 g (157 mmol) of sodium borohydride in a mixture of 140 mL of dioxane and 60 mL of ethanol. The reaction mixture was stirred at ambient temperature for 2 h. The excess sodium borohydride was destroyed with acid. The reaction mixture was concentrated in vacuo and the residue was partitioned between methylene chloride and water (4:1). The organic layer was dried over anhydrous magnesium sulfate, filtered and concentrated. The residue was purified on silica gel eluted with 20% methylene chloride in hexane to afford 6.5 g (45.8% yield) of the title compound; MS DCl—NH$_3$ M/Z: 214 (M+NH$_4$)$^+$; $^1$H NMR (CDCl$_3$) δ3.45 (2H, t, J=7.5 Hz), 4.7 (2H, t, J=7.5 Hz), 7.5–7.58 (2H, m), 8.11–8.18 (2H, m).

Step 3: 1-(1-Carbomethoxy-1,2,3,4-tetrahydro-2-naphthyl)-2-(3-nitrophenyl)-1-nitroethane To a mixture of 2 g (10.6 mmol) of 1-carbomethoxy-3,4-dihydronaphthalene, from Step 1 of Example 46, and 2.08 g (10.6 mmol) of 2-(3-nitrophenyl)-1-nitroethane, from Step 2, in 1 mL of acetonitrile was added 0.2 mL of 1,8-diazabicyclo[5.4.0]undec-7-ene (DBU). The reaction mixture was stirred at ambient temperature for 0.5 h and then diluted with ethyl acetate. The reaction mixture was washed with 2N aqueous hydrochloric acid solution. The organic layer was separated, dried over anhydrous magnesium sulfate, filtered and concentrated in vacuo to give 3.96 g (97% yield) of the title compound as a mixture of diastereomers which was taken on without purification to the next step; MS DCl—NH$_3$ M/Z: 402 (M+NH$_4$)$^+$; $^1$H NMR (CDCl$_3$) δ1.52–1.86 (1H, m), 2.1–2.35 (1H, m), 2.42–2.65 (1H, m), 2.78–3.15 (2H, m), 3.2–3.33 (1H, m), 3.38–3.55 (1H, m), 3.78–3.81 (3H, s), 3.91–4.18 (1H, m), 4.68–4.88 (1H, m), 7.12–7.42 (4H, m), 7.48–7.58 (2H, m), 8.01–8.18 (2H, m).

Step 4: 3-(3-Acetaminophenyl)methyl-2,3,3a4,5,9b-hexahydro-1H-oxo-benz[e]isoindole A mixture of 3.96 g (10.6 mmol) of 1-(1-carbomethoxy-1,2,3,4-tetrahydro-2-naphthyl)-2-(3-nitrophenyl)-1-nitroethane, from Step 3, and 12 g of zinc in 400 mL of glacial acetic acid was heated at reflux temperature overnight. The reaction mixture was concentrated in vacuo and the residue was partitioned between ethyl acetate and water (4:1). The ethyl acetate solution was dried over anhydrous magnesium sulfate, filtered and concentrated in vacuo. The residue was purified by chromatography on silica gel eluted with 90% hexane in ethyl acetate to afford 2.36 g (70% yield) of the title compound as a mixture of isomers; MS DCl—NH$_3$ M/Z:335 (M+H)$^+$,352 (M+NH$_4$)$^+$.

Step 5: 3-(5-Acetamino-2-chlorophenyl)methyl-2,3,3a,4,5,9b-hexahydro-1H-oxo-benz[e]isoindole To a suspension of 2.0 g (6 mmol) of 3-(3-acetaminophenyl)methyl-2,3,3a,4,5,9b-hexahydro-1H-oxo-benz[e]isoindole, from Step 4, in 20 mL of chloroform, cooled to −45° C., was added 0.75 mL of t-butylhypochlorite. The reaction mixture was stirred at −45° C.

for 2 h, and at 0° C. for 1 h. The reaction mixture was poured into water and the resultant aqueous mixture was extracted with methylene chloride. The organic layer was dried over anhydrous magnesium sulfate, filtered and concentrated in vacuo to afford 1.9 g (86% yield) of the title compound as a mixture of diastereomers; MS DCl—NH₃ M/Z:369 (M+H)⁺,386 (M+NH₄)⁺.

Step 6:
3-(5-(N-Ethyl)amino-2-chlorophenyl)methyl-2,3,3a,4,5,9b-hexahydro-1H-oxo-benz[e]isoindole 3-(5-Acetamino-2-chlorophenyl)methyl-2,3,3a,4,5,9b-hexahydro-1H-oxo-benz[e]isoindole (2.4 g, 6.5 mmol), from Step 5, was dissolved in 150 mL of anhydrous THF. To the resultant solution was added 35 mL of a 1M solution of borane in THF (35 mmol). The reaction mixture was heated at reflux temperature for 4 h. The solvent was removed in vacuo and the residue was partitioned between methylene chloride and dilute aqueous sodium hydroxide solution. The organic layer was separated, dried over anhydrous magnesium sulfate, filtered and concentrated in vacuo. The residue was purified by chromatography on silica gel eluted with ethyl acetate:formic acid:water (18:1:1) to give 0.8 g (36% yield) of the title compound; MS DCl—NH₃ M/Z: 348 (M+H)⁺; ¹H NMR (CDCl₃) δ1.12–1.45 (3H, m), 1.5–1.8 (1H, m), 1.88–1.98 (1H, m), 2.1–2.4 (1H, m), 2.5–2.9 (3H, m), 3.02–3.25 (2.5H, m), 3.45–3.51 (1.5H, m), 3.63–3.72 (0.5H, m), 3.78–3.88 (0.5H, m), 6.44–6.51 (1H, m), 6.52–6.6 (1H, dd), 6.95–7.18 (5H, m).

Step 7:
cis-3-(3-Chloro-4-N-ethyl-N-methylaminophenyl)methyl-2,3,3a,4,5,9b-hexahydro-2-methyl-1H-benz[e]isoindole hydrochloride To 0.8 g (2.35 mmol) of 3-(5-(N-ethyl)amino-2-chlorophenyl)methyl-2,3,3a,4,5,9b-hexahydro-1H-oxo-benz[e]isoindole, from Step 6, was added 25 mL of methanol, 6 mL of formalin (37% aqueous formaldehyde solution) and 0.5 g of sodium cyanoborohydride. The reaction mixture was stirred at ambient temperature for 0.5 h and then concentrated in vacuo. The residue was partitioned between methylene chloride and dilute aqueous sodium hydroxide solution. The organic layer was separated, dried over anhydrous magnesium sulfate, filtered and concentrated in vacuo. The residue was purified by chromatography on silica gel eluted with 2:1 diethyl ether:hexane saturated with ammonium hydroxide to give the free amine of the desired product as the major isomer. The amine was converted to the hydrochloride salt which was recrystallized from acetone/diethyl ether to give 0.22 g (25.5% yield) of the title compound, m.p. 145°–148° C.; MS DCl—NH₃ M/Z: 369 (M+H)⁺; ¹H NMR (CDCl₃) δ1.12 (3H, t), 1.65–1.72 (1H, m), 2.05–2.12 (1H, m), 2.2–2.3 (1H, m), 2.48 (3H, s), 2.59–2.72 (1H, m), 2.8 (3H, s), 2.78–3.1 (5H, m), 3.15–3.28 (1H, m), 3.3–3.48 (3H, m), 6.52 (1H, dd), 6.7 (1H, bs), 7.0–7.15 (4H, m), 7.18 (1H, d).

EXAMPLE 46
3-(3-Chlorophenyl)methyl-2,3,3a,4,5,9b-hexahydro-2-methyl-1H-benz[e]isoindole Step 1: 1-Carbomethoxy-3,4-dihydronaphthalene 1-Cyano-3,4-dihydronaphthalene (1 g, 6.45 mmol), the product of Step 1 of Example 9, was added to 10 mL of a 77% solution of concentrated sulfuric acid in methanol. The reaction mixture was heated at 95° C. for 2 h and then poured onto ice. The aqueous mixture was filtered and the filtrate was extracted with three portions of ethyl acetate. The combined organic extract was washed with brine, dried over anhydrous magnesium sulfate, filtered and concentrated in vacuo. The residue was purified on silica gel eluted with 20% ethyl acetate in hexane to afford 0.54 g (45% yield) of the title compound as a colorless oil; MS DCl—NH₃ M/Z: 189 (M+H)⁺, 206 (M+NH₄)⁺; ¹H NMR (CDCl₃) δ2.37–2.45 (2H, m), 2.73–2.82 (2H, t, J=7.5 Hz), 3.85 (3H, s), 7.13–7.25 (4H, m), 7.78 (1H, d, J=7.5 Hz).

Step 2: 2-(3-Chlorophenyl)-1-nitroethene

A mixture of 28.11 g (200 mmol) of 3-chlorobenzaldehyde, 15.4 g of ammonium acetate and 32.5 mL of nitromethane in 230 mL of glacial acetic acid was heated at reflux temperature for 3 h and then poured onto ice. The resultant aqueous mixture was made basic by the addition of 45% aqueous potassium hydroxide. The precipitate was filtered and crystallized from ethyl acetate/hexane to give 5 g of the title compound. The filtrate was concentrated to afford an additional 13.5 g of product.

Step 3: 2-(3-Chlorophenyl)-1-nitroethane

A solution of 13.5 g (72 mmol) of 2-(3-Chlorophenyl)-1-nitroethene, from Step 2, in 200 mL of dioxane was added dropwise to a stirred suspension of 6 g (157 mmol) of sodium borohydride in a mixture of 140 mL of dioxane and 60 mL of ethanol. The reaction mixture was stirred at ambient temperature for 2 h and then the excess borohydride was quenched with acid. The reaction mixture was concentrated in vacuo and the residue was partitioned between methylene chloride and water (4:1). The organic layer was dried over anhydrous magnesium sulfate, filtered and concentrated under reduced pressure. The residue was purified on silica gel eluted with 20% methylene chloride in hexane to afford 6.3 g (48% yield) of the title compound; MS DCl—NH₃ M/Z: 203 (M+NH₄)⁺; ¹H NMR (CDCl₃) δ3.3 (2H, t, J=7.5 Hz), 4.6 (2H, t, J=7.5 Hz), 7.05–7.3 (4H, m).

Step 4:
1-(1-Carbomethoxy-1,2,3,4-tetrahydro-2-naphthyl)-2-(3-chlorophenyl)-1-nitroethane To a mixture of 0.47 g (2.5 mmol) of 1-carbomethoxy-3,4-dihydronaphthalene, from Step 1, and 0.45 g (2.5 mmol) of 2-(3-chlorophenyl)-1-nitroethane, from Step 3, was added 180 μL (1.25 mmol) of 1,8-diazabicyclo[5.4.0]undec-7-ene (DBU) in 5 mL of acetonitrile. The reaction mixture was stirred at ambient temperature for 45 min and then diluted with methylene chloride. The resultant mixture was poured into 2N aqueous hydrochloric acid solution and the layers were separated. The organic layer was dried over anhydrous magnesium sulfate, filtered and concentrated in vacuo to give 1.1 g of oil. The oil was purified by chromatography on silica gel eluted with 10% ethyl acetate in hexane to give isomeric products. The title compound was obtained in 45% yield (0.17 g); MS DCl—NH₃ M/Z: 391 (M+H)⁺; ¹H NMR (CDCl₃) δ1.48–1.52 (1H, m), 2.1–2.2 (1H, m), 2.71–3.22 (6H, m), 3.75 (3H, s), 4.65–4.75 (1H, m), 6.97–7.28 (8H, m).

Step 5:
3-(3-Chlorophenyl)methyl-2,3,3a,4,5,9b-hexahydro-1H-oxo-benz[e]isoindole A mixture of 3.1 g (8.3 mmol) of 1-(1-carbomethoxy-1,2,3,4-tetrahydro-2-naphthyl)-2-(3-chlorophenyl)-1-nitroethane, from Step 4, and 6 g of zinc in 350 mL of acetic acid was heated at reflux temperature overnight. The reaction mixture was concentrated in vacuo and the residue was partitioned between ethyl acetate and water (4:1). The ethyl acetate solution was dried over anhydrous magnesium sulfate, filtered and concentrated in vacuo. The residue was purified by chromatography on silica gel eluted with 80% ethyl acetate in hexane, followed by 100% ethyl acetate to afford 1.8 g (69% yield) of the title compound as a mixture of isomers; MS DCl—NH$_3$ M/Z: 312 (M+H)$^+$, 329 (M+NH$_4$)$^+$; $^1$H NMR (CDCl$_3$) δ1.63–1.81 (1H, m), 1.78–2.02 (1, m), 2.63–2.85 (3H, m), 2.87–2.98 (1H, m), 3.52–3.6 (0.5H, m), 3.6–3.72 (1H, m), 4.02–4.11 (0.5H, m), 5.39 (0.5H, bs), 5.58 (0.5H, bs), 7.03–30 (7H, m), 7.49 (0.5H, d), 7.58 (0.5H, d).

Step 6:
3-(3-Chlorophenyl)methyl-2,3,3a,4,5,9b-hexahydro-1H-benz[e]isoindole 3-(3-Chlorophenyl)-2,3,3a,4,5,9b-hexahydro-1H-oxo-benz[e]isoindole (1.8 g, 5.8 mmol), from Step 5, was dissolved in 100 mL of anhydrous THF and to this solution was added 25 mL of a 1M solution of borane in THF (25 mmol). The reaction mixture was heated at reflux temperature for 4 h, and then concentrated in vacuo. The residue was dissolved in methylene chloride saturated with hydrogen chloride and the resultant solution was heated at reflux temperature for 4 h. The solvent was removed in vacuo and the residue partitioned between methylene chloride and dilute aqueous sodium hydroxide. The organic layer was separated, dried over anhydrous magnesium sulfate, filtered and concentrated in vacuo. The residue was purified by chromatography on silica gel eluted with ethyl acetate:-formic acid:water (18:1:1) to give 0.9 g (53% yield) of the title compound; MS DCl—NH$_3$ M/Z: 298 (M+H)$^+$; $^1$H NMR (CDCl$_3$) δ1.49–1.95 (1H, m), 2.11–2.32 (1H, m), 2.6–3.15 (5H, m), 3.32–3.71 (3H, m), 7.01–7.3 (8H, m).

EXAMPLE 47

3-(3-Chlorophenyl)methyl-2,3,3a,4,5,9b-hexahydro-2-methyl-1H-benz[e]isoindole hydrochloride To 0.9 g (3 mmol) of 3-(3-chlorophenyl)-2,3,3a,4,5,9b-hexahydro-1H-benz[e]isoindole, the product of Example 46, was added 25 mL of methanol, 5.5 mL of formalin (37% aqueous formaldehyde solution) and 0.5 g of sodium cyanoborohydride. The reaction mixture was stirred at ambient temperature for 2 h, acidified with a few drops of methanol saturated with hydrogen chloride and then stirred at ambient temperature for another hour. The reaction was quenched with 6N aqueous hydrochloric acid. The reaction mixture was stirred at ambient temperature for 0.5 h and then concentrated in vacuo. The residue was partitioned between methylene chloride and dilute aqueous sodium hydroxide solution. The organic layer was separated, dried over anhydrous magnesium sulfate, filtered and concentrated in vacuo. The residue was purified by chromatography on silica gel eluted with 1:1 diethyl ether:hexane saturated with ammonium hydroxide to give the free amines of the desired isomeric products. The amines were converted to the hydrochloride salts which were recrystallized from ethyl acetate/diethyl ether to give two isomeric products. Isomer 1 (0.35 g), m.p. 180°–181° C.; MS DCl—NH$_3$ M/Z: 312 (M+H)$^+$; $^1$H NMR (CDCl$_3$) δ1.6–1.7 (1H, m), 1.84–1.96 (1H, m), 2.12–2.23 (1H, m), 2.39 (3H, s), 2.51–2.86 (4H, m), 2.87–2.97 (2H, m), 3.16–3.23 (1H, m), 3.29–3.39 (1H, m), 7.01–7.29 (8H, m). Analysis calculated for C$_{20}$H$_{23}$Cl$_2$N: C, 67.23; H, 6.77; N, 3.92. Found: C, 67.42; H, 6.61; N, 3.87. Isomer 2 (0.28 g), m.p. 170°–175° C.; MS DCl—NH$_3$ M/Z: 312 (M+H)$^+$; $^1$H NMR (CDCL$_3$) δ1.18–1.41 (2H, m), 2.17–2.41 (3H, m), 2.38 (3H, s), 2.48–2.53 (3H, m), 2.98–3.08 (1H, dd), 3.32–3.48 (2H, m), 7.0–7.3 (8H, m). Analysis calculated for C$_{20}$H$_{23}$Cl$_2$N: C, 67.23; H, 6.77; N, 3.92. Found: C, 67.26; H, 6.60; N, 3.86.

EXAMPLE 48 trans-7-Chloro-3-(3-chlorophenyl)methyl-2,3,3a,4,5,9b-hexahydro-2-methyl-1H-benz[e]isoindole hydrochloride

Step 1:
1-Carbomethoxy-6-chloro-3,4-dihydronaphthalene

6-Chloro-1-cyano-3,4-dihydronaphthalene (5 g, 263 mmol), lit ref, was dissolved in 77% sulfuric acid in methanol and the resulting solution was heated at 95°–100° C. for 2.5 h. The reaction mixture was allowed to cool to ambient temperature and 45 mL was added, followed by 5 mL of water. The reaction mixture was stirred at ambient temperature for 2 days and then concentrated under reduced pressure. The residue was partitioned between ethyl acetate and water. The organic layer was concentrated in vacuo. The residue was purified by chromatography on silica gel eluted with 20% ethyl acetate in hexane to give 1.53 g (26% yield) of the title compound; MS DCl—NH$_3$ M/Z: 240 (M+H)$^+$; $^1$H NMR (CDCl$_3$) δ2.37–2.45 (2H, m), 2.75 (2H, t, J=7.5 Hz), 3.85 (3H, s), 7.15 (1H, d, J=1.5 Hz), 7.15 (1H, d, 9 Hz), 7.2 (1H, d, J=7.5 Hz), 7.77 (1H, d, J=7.5).

Step 2:
1-(1-Carbomethoxy-6-chloro-1,2,3,4-tetrahydro-2-naphthyl)-2-(3-chlorophenyl)-1-nitroethane Following the procedures described in Step 4 of Example 46, replacing 1-carbomethoxy-3,4-dihydronaphthalene with 1.51 g (6.78 mmol) of 1-carbomethoxy-6-chloro-3,4-dihydronaphthalene from Step 1, the title compound was prepared in 80% yield (2.3 g) as a mixture of diastereomers; MS DCl—NH$_3$ M/Z: 425 (M+H)$^+$.

Step 3:
7-Chloro-3-(3-chlorophenyl)methyl-2,3,3a,4,5,9b-hexahydro-1H-oxo-benz[e]isoindole Following the procedures described in Step 5 of Example 46, replacing 1-(1-carbomethoxy-1,2,3,4-tetrahydro-2-naphthyl)-2-(3-chlorophenyl)-1-nitroethane with 0.83 g (1.96 mmol) of 1-(1-carbomethoxy-6-chloro-1,2,3,4-tetrahydro-2-naphthyl)-2-(3-chlorophenyl)-1-nitroethane, from Step 2, to give 0.59 g (87% yield) of the title compound as white crystals, m.p. 190°–192° C.; MS DCl—NH$_3$ M/Z: 346 (M+H)$^+$; $^1$H NMR (CDCl$_3$) δ1.52–2.05 (2H, m), 2.67–3.0 (5H, m), 3.5–3.6 (1H, m), 4.0–4.1 (1H, m), 7.05–7.45 (7H, m).

Step 4:
7-Chloro-3-(3-chlorophenyl)methyl-2,3,3a,4,5,9b-hexahydro-1H-benz[e]isoindole Following the procedures described in Step 6 of Example 46, replacing 3-(3-Chlorophenyl)methyl-2,3,3a,4,5,9b-hexahydro-1H-oxo-benz[e]isoindole with 1.25 g (3.62 mmol) of 7chloro-3-(3-chlorophenyl)methyl-2,3,3a,4,5,9b-hexahydro-1H-oxo-benz[e]isoindole, from Step 3, the title compound was prepared; MS DCl—NH$_3$ M/Z: 334 (M+H)$^+$; $^1$H NMR (CDCl$_3$) δ1.43–1.95 (2H, m), 2.07–2.43 (1H, m), 2.54–3.15 (5H, m), 3.2–3.7 (3H, m), 6.92–7.32 (7H, m).

Step 5:
trans-6-Chloro-3-(3-chlorophenyl)methyl-2,3,3a,4,5,9b-hexahydro-2-methyl-1H-benz[e]isoindole hydrochloride Following the procedures described in Example 44, replacing 7-bromo-2,3,3a,4,5,9b-hexahydro-3-phenylmethyl-1H-benz[e]isoindole with 1.35 g (4.05 mmol) 7-chloro-3-(3-chlorophenyl)methyl-2,3,3a,4,5,9b-hexahydro-1H-benz[e]isoindole, from Step 4, the title compound was prepared as a mixture with Example 49. The two diastereomers were separated by chromatography on silica gel eluted with 2:1 diethyl ether: hexane saturated with ammonium hydroxide. Example 48 was obtained in 40% yield (0.56 g), m.p. 160°–162° C.; MS DCl—NH$_3$ M/Z: 346 (M+H)$^+$. Analysis calculated for C$_{20}$H$_{22}$Cl$_3$N+H$_2$O: C, 59.94; H, 6.04; N, 3.49. Found: C, 60.46; H, 5.72; N, 3.49.

EXAMPLE 49 cis-7-Chloro-3-(3-chlorophenyl)methyl-2,3,3a,4,5,9b-hexahydro-2-methyl-1H-benz[e]isoindole hydrochloride The title compound was obtained as described in Example 48 in 33% yield (0.46 g), m.p. 110°–112° C.; MS DCl—NH$_3$ M/Z: 346 (M+H)$^+$. Analysis calculated for C$_{20}$H$_{22}$Cl$_3$N+H$_2$O: C, 59.94; H, 6.04; N, 3.49. Found: C, 59.63; H, 5.87; N, 3.46.

EXAMPLE 50

1,2,3,4,4a,5,6,10b-Octahydro-4-phenylmethyl-benz[f]isoquinoline methanesulfonic acid salt

Step 1:
1-Cyano-2-(1-cyano-2-phenyl-1-ethyl)-1,2,3,4-tetrahydronaphthalene

To a solution of 3.5 mL (25 mmol) of diisopropylamine in 40 mL of THF at −78° C., under a nitrogen atmosphere, was added n-butyllithium (9.5 mL of a 2.5M solution in THF, 23.7 mmol) and the resultant solution was stirred at −78° C. for 0.5 h. To the stirred solution was slowly added a solution of 2.75 g (21 mmol) of 3-phenylpropiononitrile in 40 mL of THF. The reaction mixture was stirred for 45 min at −78° C. and then a solution of 3.1 g (20 mmol) of 1-cyano-3,4-dihydronaphthalene (the product of Step 1 of Example 9) in 40 mL of THF was added. The reaction mixture was stirred at −78° C. for 0.5 h and then the reaction was quenched by pouring the reaction mixture into saturated aqueous ammonium chloride solution. The layers were separated and the aqueous layer was extracted with ethyl acetate. The combined organic layers were dried over anhydrous magnesium sulfate, filtered and concentrated in vacuo to give 5.70 g (quantitative yield) of the title compound as a mixture of three diastereomers; MS DCl—NH$_3$ M/Z: 287 (M+H)$^+$.

Step 2:
1,3-Dioxo-1,2,3,4,4a,5,6,10b-octahydro-4-phenylmethyl-benz[f]isoquinoline 1-Cyano-2-(1-cyano-2-phenyl-1-ethyl)-1,2,3,4-tetrahydronaphthalene (9.43 g, 33 mmol), from Step 1, was dissolved in 200 mL of methylene chloride and the resultant solution was cooled to 0° C. The reaction mixture was flushed with nitrogen gas and hydrogen bromide gas was then bubbled in for 1.5 h at 0° C. Nitrogen was bubbled through the reaction mixture for 1.5 h to remove the excess hydrogen bromide and the reaction mixture was then allowed to warm to ambient temperature. The solvent was removed under reduced pressure and the residue was washed with diethyl ether/hexane (1:2). The solvent was decanted and the residue was dissolved in 100 mL of DMF:water (1:1). The resultant solution was heated at reflux for 3 h, allowed to cool to ambient temperature and stirred overnight at ambient temperature. The reaction mixture was poured into ice water and the aqueous mixture was extracted with ethyl acetate. The ethyl acetate extract was washed with water, dried over anhydrous magnesium sulfate, filtered and concentrated in vacuo to afford the title compound.

Step 3:
1,2,3,4,4a,5,6,10b-Octahydro-4-phenylmethyl-benz[f]isoquinoline methanesulfonic acid salt To a solution of 1,3-Dioxo-1,2,3,4,4a,5,6,10b-octahydro-3-phenylmethyl-benz[f]isoquinoline, from Step 2, in 40 mL of THF was added a solution of borane in THF and the reaction mixture was heated at reflux for 3 h. The solvent was removed in vacuo and the residue was dissolved in 25 mL of methanol. To this solution was added 30 mL of methanol saturated with anhydrous hydrogen chloride and the reaction mixture was heated at reflux for 2 h. The solvent was evaporated in vacuo and the residue was partitioned between methylene chloride and 3 N aqueous sodium hydroxide solution (4:1). The basic aqueous layer was extracted with two portions of methylene chloride. The combined methylene chloride layers were dried over anhydrous magnesium sulfate, filtered and concentrated under reduced pressure to give 0.47 g of the desired product as a mixture of the two diastereomers of the free amine which was converted to the methanesulfonic acid salt, m.p. 156°–157° C.; MS DCl—NH$_3$ M/Z: 278 (M+H)$^+$. Analysis calculated for C$_{21}$H$_{27}$NO$_3$S: C, 67.53; H, 7.29; N, 3.75. Found: C, 67.03; H, 7.24; N, 3.68.

EXAMPLE 51 cis-2-Methyl-1,2,3,4,4a,5,6,10b-octahydro-4-phenylmethyl-benz[f]isoquinoline hydrochloride The product of Example 50 was subjected to reductive methylation as described in Example 2. The two diastereomers of the desired product were separated by chromatography on silica gel eluted with 2:1 diethyl ether:hexane saturated with ammonium hydroxide to give the title compound and 52 as the free amine products. The free amine of the title compound was converted to the hydrochloride salt which was recrystalized form a mixture of hexane and ethyl acetate, m.p. 204°–205° C.; MS DCl—NH$_3$ M/Z: 292 (M+H)$^+$; $^1$H NMR (CDCl$_3$) δ1.5–1.6 (1H, m), 1.78–1.92 (2H, m), 2.05–2.35 (3H, m), 2.18 (3H, s), 2.64–3.0 (5H, m), 3.15–3.25 (1H, m), 7.0–7.28 (9H, m). Analysis calculated for $C_{21}H_{26}ClNO+0.25H_2O$: C, 75.88; H, 8.04; N, 4.21. Found: C, 75.76; H, 7.99; N, 4.17.

EXAMPLE 52 trans-2-Methyl-1,2,3,4,4a,5,6,10b-octahydro-4-phenylmethyl-benz[f]isoquinoline hydrochloride The free amine of the title compound, obtained as described in Example 51, was converted to the hydrochloride salt which was recrystallized from a mixture of hexane and ethyl acetate, m.p. 233°–234° C.; MS DCl—NH₃ M/Z: 292 (M+H)+; ¹H NMR (CDCl₃) δ1.83–2.18 (3H, m), 2.66–3.22 (8H, m), 2.83 (3H, s), 3.37–3.47 (1H, m), 7.1–7.38 (9H, m). Analysis calculated for $C_{21}H_{26}ClNO+0.25H_2O$: C, 75.88; H, 8.04; N, 4.21. Found: C, 75.89; H, 8.05; N, 4.15.

EXAMPLE 53

8-Methoxy-1,2,3,4,4a,5,6,10b-octahydro-benz[f]isoquinoline methanesulfonic acid

Step 1:
1-Cyano-2-(cyanomethyl)-6-methoxy-1,2,3,4-tetrahydronaphthalene

To a solution of 1.05 mL (7.5 mmol) of diisopropylamine in 10 mL of THF at −78° C., under a nitrogen atmosphere, was added n-butyllithium (2.2 mL of a 2.5M solution in THF, 5.5 mmol) and the resultant solution was stirred at −78° C. for 40 min. To the stirred solution was added, dropwise over a 25 minute period, a solution of 274 μL (5.25 mmol) of acetonitrile in 5 mL of THF. The solution was stirred for 20 min at −78° C. and then a solution of 926 mg (5 mmol) of 1-cyano-6-methoxy-3,4-dihydronaphthalene (the product of Step 2 of Example 1) in 5 mL of THF was added via syringe pump over a 20 min period. The reaction mixture then allowed to warm to ambient temperature and was stirred at ambient temperature for 1 h and then the reaction was quenched by pouring the reaction mixture into and then the reaction was quenched by pouring the reaction mixture into saturated aqueous ammonium chloride solution. The layers were separated and the aqueous layer was extracted with ethyl acetate. The combined organic layers were dried over anhydrous magnesium sulfate, filtered and concentrated in vacuo. The residue was purified by chromatography on silica gel eluted with 25% ethyl acetate in hexane to give 840 mg (74% yield) of the title compound as a 1:1 mixture of the cis and trans isomers; MS DCl—NH₃ M/Z: 244 (M+H)+.

Step 2:
1,3-Dioxo-8-methoxy-1,2,3,4,4a,5,6,10b-octahydro-benz[f]isoquinoline Following the procedures described in Step 2 of Example 50, replacing 1-cyano-2-(1-cyano-2-phenyl-1-ethyl)-1,2,3,4-tetrahydronaphthalene with 7.33 g (32.4 mmol) of 1-cyano-2-(cyanomethyl)-6-methoxy-1,2,3,4-tetrahydronaphthalene, from Step 1, the title compound was prepared in 63% yield (5 g) as a 10:1 mixture of the cis and trans isomers; MS DCl—NH₃ M/Z: 246 (M+H)+, 263 (M+NH₄)+; ¹H NMR of cis isomer (CDCl₃) δ1.67–1.81 (1H, m), 1.87–1.98 (1H, m), 2.52–2.63 (1H, m), 2.67 (1H, dd), 2.83 (1H, dd), 2.89 (2H, m), 3.73 (1H, d), 3.80 (3H, s), 6.67 (1H, d), 6.80 (1H, dd), 7.28 (1H, d), 7.84 (1H, bs).

Step 3:
8-Methoxy-1,2,3,4,4a,5,6,10b-octahydro-benz[f]isoquinoline methanesulfonic acid salt Following the procedures described in Step 3 of Example 50, replacing 1,3-dioxo-1,2,3,4,4a,5,6,10b-octahydro-3-phenylmethyl-benz[f]isoquinoline, with 5.0 g (20.4 mmol) of 1,3-dioxo-8-methoxy-1,2,3,4,4a,5,6,10b-octahydro-benz[f]isoquinoline, from Step 2, the desired product was obtained as the free amine which was purified on silica gel eluted with ethyl acetate:water:formic acid (18:1:1) to give 2.65 g (60% yield) of the methanesulfonic acid salt, m.p. 171°–174° C.; MS DCl—NH₃ M/Z: 218 (M+H)+. ¹H NMR (CDCl₃) δ1.61–1.70 (1H, m), 1.78–1.87 (1H, m), 1.94–2.04 (1H, m), 2.18–2.38 (2H, m), 2.78 (3H, s), 2.83–2.90 (2H, m), 2.92–3.08 (2H, m), 3.25–3.47 (3H, m), 3.77 (3H, s), 6.62 (1H, d), 6.71 (1H, dd), 7.09 (1H, d), 8.34–9.01 (1H, bs). Analysis calculated for $C_{15}H_{23}NO_4S$: C, 57.49; H, 7.40; N, 4.47. Found: C, 57.31; H, 7.39; N, 4.36.

EXAMPLE 54

8-Methoxy-2-methyl-1,2,3,4,4a,5,6,10b-octahydro-benz[f]isoquinoline methanesulfonic acid The product of Example 53 was subjected to reductive methylation as described in Example 2. The two diastereomers of the desired product (formed in a ratio of 10:1 cis:trans) were not separated by chromatography. The free amine of the title compound was obtained in 84% yield (670 mg) and converted to the hydrochloride salt, m.p. 107°–114° C.; MS DCl—NH₃ M/Z: 232 (M+H)+ ¹H NMR (CDCl₃) δ1.09 (3H, t), 1.47–1.55 (1H, m), 1.61–1.76 (2H, m), 1.97–2.17 (4H, m), 2.34–2.48 (2H, m), 2.87 (3H, s), 2.97–3.06 (1H, m), 3.77 (3H, s), 6.61 (1H, d), 6.71 (1H, dd), 7.06 (1H, d). Analysis calculated for $C_{16}H_{25}NO_4S+0.25H_2O$: C, 58.68; H, 7.70; N, 4.28. Found: C, 57.89; H, 7.74; N, 4.42.

EXAMPLE 55

2-Ethyl-8-methoxy-1,2,3,4,4a,5,6,10b-octahydro-benz[f]isoquinoline methanesulfonic acid Following the procedures described in Example 3, replacing 2,3,3a,4,5,9b-hexahydro-7-methoxy-2-methyl-3-phenylmethyl-1H-benz[e]isoindole with 1.55 g (7.1 mmol) of the free amine product of Example 53, the title compound was prepared, m.p. 141°–141.5° C.; MS DCl—NH₃ M/Z: 246 (M+H)+. Analysis calculated for $C_{17}H_{27}NO_4S$: C, 59.80; H, 7.97; N, 4.10. Found: C, 59.79; H, 7.94; N, 4.07.

EXAMPLE 56

2-Ethyl-8-methoxy-1,2,3,4,4a,5,6,10b-octahydro-4-phenylmethyl-benz[f]isoquinoline methanesulfonic acid salt

Step 1:
1-Cyano-2-(1-cyano-2-phenyl-1-ethyl)-1,2,3,4-tetrahydronaphthalene

Following the procedures described in Step 1 of Example 53, replacing acetonitrile with 2.75 g (21 mmol) of 3-phenylpropionitrile, the title compound was obtained in 84% yield (5.3 g) as a mixture of isomers; MS DCl—NH₃ M/Z: 334 (M+H)+.

Step 2:
1,3-Dioxo-8-methoxy-1,2,3,4,4a,5,6,10b-octahydro-4-phenylmethyl-benz[f]isoquinoline Following the procedures described in Step 2 of Example 50, replacing 1-cyano-2-(1-cyano-2-phenyl-1-ethyl)-1,2,3,4-tetrahydronaphthalene with 6.64 g (21 mmol) of 1-cyano-2-(1-cyano-2-phenyl-1-ethyl)-1,2,3,4-tetrahydronaphthalene, from Step 1, the title compound was prepared and carried on to the next step without purification; MS DCl—NH$_3$ M/Z: 336 (M+H)$^+$, 353 (M+NH$_4$)$^+$.

Step 3:
8-Methoxy-1,2,3,4,4a,5,6,10b-octahydro-4-phenylmethyl-benz[f]isoquinoline Following the procedures described in Step 3 of Example 50, replacing 1,3-dioxo-1,2,3,4,4a,5,6,10b-octahydro-4-phenylmethyl-benz[f]isoquinoline with 0.93 g (2.77 mmol) of 1,3-dioxo-8-methoxy-1,2,3,4,4a,5,6,10b-octahydro-4-phenylmethyl-benz[f]isoquinoline, from Step 2, the desired product was prepared as a mixture of the two diastereomers.

Step 4:
2-Ethyl-8-methoxy-1,2,3,4,4a,5,6,10b-octahydro-4-phenylmethyl-benz[f]isoquinoline methanesulfonic acid salt Following the procedures described in Example 3, replacing 2,3,3a,4,5,9b-hexahydro-7-methoxy-3-phenylmethyl-1H-benz[e]isoindole with 0.97 g (3.2 mmol) of the product of Step 3, the title compound was prepared, m.p. 127.5°–134° C.; MS DCl—NH$_3$ M/Z: 336 (M+H)$^+$. $^1$H NMR of the free base (CDCl$_3$) δ1.06 (3H, t), 1.73-2.00 (4H, m), 2.08 (1H, dd), 2.27-2.48 (3H, m), 2.56-2.74 (4H, m), 2.78-2.88 (2H, m), 2.92-3.02 (1H, m), 3.77 (3H, s), 6.58 (1H, d), 6.68 (1H, dd), 7.02 (1H, d), 7.13-7.32 (5H, m). Analysis calculated for C$_{24}$H$_{33}$NO$_4$S+H$_2$O: C, 64.11; H, 7.85; N, 3.12. Found: C, 64.39; H, 7.86; N, 3.07.

EXAMPLE 57
2,10b-Diethyl-8-ethoxy-1,2,3,4,4a,5,6,10b-octahydro-4-phenylmethyl-benz[f]isoquinoline methanesulfonic acid salt

Step 1:
1,3-Dioxo-8-hydroxy-1,2,3,4,4a,5,6,10b-octahydro-4-phenylmethyl-benz[f]isoquinoline To a flask containing 4.69 g (14.8 mmol) of 1-cyano-2-(1-cyano-2-phenyl-1-ethyl)-1,2,3,4-tetrahydronaphthalene, the product of Step 1 of Example 56, was added 150 mL of glacial acetic acid and 30 mL of concentrated sulfuric acid. The reaction mixture was heated at 100° C. for 2 h, allowed to cool to ambient temperature and stirred at ambient temperature overnight. Hydrochloric acid (150 mL of a 6N aqueous solution) was added to the reaction mixture and the reaction mixture was heated at reflux for 8 h. The reaction mixture was then allowed to cool to ambient temperature and was stirred at ambient temperature for approximately 64 h. The reaction mixture was poured onto ice and the aqueous mixture was made basic by the addition of solid sodium carbonate, followed by saturated aqueous sodium bicarbonate solution and then 45% aqueous sodium hydroxide solution. The mixture was kept cold (~0° C.) during the pH adjustment. The aqueous mixture was extracted with three portions of methylene chloride. The combined organic extract was dried over anhydrous magnesium sulfate, filtered and concentrated under reduced pressure. The residue was purified by chromatography on silica gel eluted with hexane:ethyl acetate to give 1.42 g of the title compound as a mixture of diastereomers; MS DCl—NH$_3$ M/Z: 364 (M+H)$^+$, 381 (M+NH$_4$)$^+$.

Step 2:
1,3-Dioxo-8-ethoxy-2-ethyl-1,2,3,4,4a,5,6,10b-octahydro-4-phenylmethyl-benz[f]isoquinoline A solution of 1.42 g (4.42 mmol) of 1,3-dioxo-8-hydroxy-1,2,3,4,4a,5,6,10b-octahydro-4-phenylmethyl-benz[f]isoquinoline, from Step 1, in 20 mL of dry DMF was cooled to 0° C. under a nitrogen atmosphere. To this solution at 0° C., was added portionwise, 3 mL of a suspension of sodium hydride in hexane. The reaction mixture was stirred at 0° C. for 10 min and then at ambient temperature for 1 h. The reaction mixture was cooled back down to 0° C. and 1.24 mL (15.5 mmol) of ethyl iodide was added. The reaction mixture was stirred at 0° C. for 0.5 h and at ambient temperature overnight and then concentrated in vacuo to give 0.16 g of the title compound; MS DCl—NH$_3$ M/Z: 406 (M+H)$^+$.

Step 3:
2,10b-Diethyl-8-ethoxy-1,2,3,4,4a,5,6,10b-octahydro-4-phenylmethyl-benz[f]isoquinoline methanesulfonic acid salt Following the procedures described in Step 3 of Example 50, replacing 1,3-dioxo-1,2,3,4,4a,5,6,10b-octahydro-4-phenylmethyl-benz[f]isoquinoline with 0.93 g (2.77 mmol) of 1,3-dioxo-8-methoxy-2-ethyl-1,2,3,4,4a,5,6,10b-octahydro-4-phenylmethyl-benz[f]isoquinoline, from Step 2, the desired product was prepared as a mixture of the two diastereomers and converted to the methanesulfonic acid salt, m.p. 172.5°–173.5° C.; MS DCl—NH$_3$ M/Z: 378 (M+H)$^+$. $^1$H NMR of the free base (CDCl$_3$) δ0.47 (3H, t), 1.01 (3H, t), 1.39 (3H, t), 1.66-1.96 (4H, m), 2.11-2.77 (9H, m), 3.98 (2H, m), 6.54 (1H, d), 6.69 (1H, dd), 7.12 (1H, d), 7.16-7.32 (5H, m).

EXAMPLES 58–70

Following the procedures described in Examples 45–49 starting with either 1-cyano-5,6-methylenedioxy-3,4-dihydronaphthalene (Examples 58–63) or 1-cyano-8-fluoro-5,6-methylenedioxy-3,4-dihydronaphthalene (Examples 64–70) which were prepared as described by F. Z. Basha, et al. in *J. Organic Chemistry*, 1985, 50: 4160-2, and the appropriate nitromethane derivative as shown in reaction scheme II, Examples 58–70 are prepared as disclosed in Table 1.

TABLE 1

| Example Number | Structure |
|---|---|
| 58 | 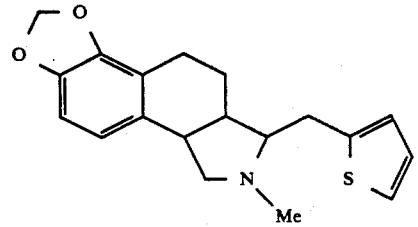 |

TABLE 1-continued

| Example Number | Structure |
|---|---|
| 59 | (structure) |
| 60 | (structure) |
| 61 | (structure) |
| 62 | (structure) |
| 63 | (structure) |
| 64 | (structure) |
| 65 | (structure) |
| 66 | (structure) |
| 67 | (structure) |
| 68 | (structure) |
| 69 | (structure) |
| 70 | (structure) |

EXAMPLE 71 cis-2-Methyl-1,2,3,4,4a,5,6,10b-octahydro-3-phenyl-methyl-benz[f]isoquinoline

Step 1: Ethyl (1-cyano-1,2,3,4-tetrahydronaphthyl-2-yl)acetate n-Butyl lithium (14.2 mL of a 2.5M solution in hexane, 35.4 mmol) was added to a solution of diisopropylamine (6.77 mL, 48 mmol) in 100 mL of dry THF at −78° C. under a nitrogen atmosphere. The solution was stirred at −78° C. for 15 min and then ethyl acetate (3.3 mL, 33.8 mmol) was added dropwise over a 10 min period. The solution was stirred at −78° C. for 30 min. A solution of 1-cyano-3,4-dihydronaphthalene (5 g, 32.2 mmol), the product of Step 1 of Example 9, in 10 mL of THF was then added over a 10 min period. The reaction mixture was stirred at −78° C., allowed to warm to ambient temperature and the reaction was quenched at ambient temperature by the addition of concentrated ammonium chloride. The organic layer was dried over anhydrous magnesium sulfate, filtered and concentrated in vacuo. The residue was purified by column chromatography on silica gel eluted with hexane:ethyl acetate (10:1) to give 5 g (90% yield) of the title compound as a mixture of diastereomers.

Step 2: cis-1,2,3,4,4a,5,6,10b-Octahydro-3-oxo-benz[f]isoquinoline

Ethyl (1-cyano-1,2,3,4-tetrahydronaphthyl-2-yl)acetate (5 g, 20.5 mmol), from Step 1, was dissolved in 300 mL of ethyl alcohol. Raney nickel (16.6 g) was added and the reaction mixture was heated to 60° C. and shaken under 4 atmospheres of hydrogen for 24 h. The filtrate was concentrated in vacuo. The residue was adsorbed onto silica gel and chromatographed on silica gel eluted with ethyl acetate:water:formic acid (200:1:1) followed by ethyl acetate:water:formic acid (100:1:1) to give 3.2 mg (78% yield) of the title compound as a 1:1 mixture of the cis and trans isomers.

Step 3: cis-2-Methyl-1,2,3,4,4a,5,6,10b-octahydro-3-oxo-benz[f]isoquinoline cis-1,2,3,4,4a,5,6,10b-Octahydro-3-oxo-benz[f]isoquinoline (3.12 g, 15.5 mmol), from Step 2, was dissolved in 100 mL of dry THF and potassium t-butoxide (2.1 g, 18.6 mmol) was added. The reaction mixture was stirred at ambient temperature for 3 h and then cooled to −78° C. Methyl iodide (5 mL, 80.3 mmol) was added. The reaction mixture was allowed to warm to ambient temperature and stirred for 15 minutes and then concentrated in vacuo. The residue was chromatographed on silica gel eluted with methylene chloride saturated with ammonia to afford 3.27 g (98% yield) of the title compound.

Step 4: cis-2-Methyl-1,2,3,4,4a,5,6,10b-octahydro-3-phenylmethyl-benz[f]isoquinoline cis-2-Methyl-1,2,3,4,4a,5,6,10b-octahydro-3-oxo-benz[f]isoquinoline (3.27 g (15.2 mmol) was dissolved in 60 mL of THF and the resultant solution was cooled to 0° C. Benzyl magnesium chloride (11.4 mL of a 2.0M solution in THF, 22.8 mmol), commercially available from Aldrich Chemical Company, was added and the reaction mixture was stirred at 0° C. for 1 h. Trifluoroacetic acid (0.5 mL) was added and then the reaction mixture was concentrated in vacuo. Methanol (50 mL) was added, followed by methanolic hydrochloric acid until the pH of the solution was between 2 and 3. A solution of sodium cyanoborohydride (2.86 g, 45.6 mmol) in 25 mL of methanol was then added slowly. The pH of the reaction mixture was maintained between 1 and 3 by the addition of methanolic hydrochloric acid. The solvent was removed in vacuo and the residue was partitioned between 1N aqueous sodium hydroxide solution and methylene chloride (1:4). The aqueous layer was extracted with 2×200 mL of methylene chloride. The combined organic layers were dried over anhydrous magnesium sulfate, filtered and concentrated in vacuo. The residue was purified by chromatography on silica gel eluted with hexane:ethyl acetate (2:1) saturated with ammonia to give the title compound as two isomeric products: (71-4A) was the first compound to elute from the column; MS DCl—NH$_3$ M/Z: 292 (M+1)$^+$; $^1$H NMR (CDCl$_3$) δ1.01–1.98 (5H, m), 2.24–2.72 (6H, m), 2.78–3.44 (5H, m), 6.80–7.35 (9H, m). Analysis calculated for C$_{21}$H$_{25}$N: C, 76.92; H, 7.99; N, 4.27. Found: C, 77.07; H, 8.04; N, 4.29. (71-4B) was the second compound to elute from the column; MS DCl—NH$_3$ M/Z: 292 (M+1)$^+$; $^1$H NMR (CDCl$_3$) δ1.05–1.76 (5H, m), 2.08–2.29 (2H, m), 2.36–2.70 (2H, m), 2.56 (3H, m), 2.77–2.89 (2H, m), 3.30 (1H, dd, J=4, 13 Hz), 3.61 (1H, dd, J=4, 13 Hz), 7.03–7.40 (9H, m). Analysis calculated for C$_{21}$H$_{25}$N: C, 76.92; H, 7.99; N, 4.27. Found: C, 77.04; H, 8.12; N, 4.29.

EXAMPLE 72 cis-8-Methoxy-2-methyl-1,2,3,4,4a,5,6,10b-octahydro-3-phenylmethyl-benz[f]isoquinoline hydrochloride

Step 1: cis-8-Methoxy-1,3-dioxo-2-methyl-1,2,3,4,4a,5,6,10b-octahydro-benz[f]isoquinoline n-Butyl lithium (8.1 mL, 20.196) was added to a solution of 3.9 mL (27.54 mmol) of diisopropylamine in 25 mL of THF at −78° C. A solution of acetonitrile (1.01 mL, 18.54 mmol) in 10 mL of dry THF was then added dropwise. The resultant solution was stirred at −78° C. for 1 h. A solution of 1-cyano-6-methoxy-3,4-dihydronaphthalene (3.4 g, 18.36 mmol), the product of Step 2 of Example 1, in 7 mL of THF was added dropwise to the anion of acetonitrile and the reaction mixture was stirred at −78° C. for 1 h. The reaction mixture was allowed to warm to ambient temperature and the reaction was quenched with aqueous ammonium chloride. The aqueous layer was extracted with ethyl acetate. The combined organic layers were dried over anhydrous magnesium sulfate, filtered and concentrated in vacuo. The residue was redissolved in methylene chloride and adsorbed onto silica gel and chromatographed on silica gel eluted with hexane/ethyl acetate (7:1) to give the intermediate acetonitrile adduct. The intermediate was dissolved in 100 mL of methylene chloride and hydrogen bromide gas was bubbled into the solution at 0° C. for 1 h. The methylene chloride was evaporated at ambient temperature with a stream of nitrogen gas. The residue was added to 50 mL of a 1:1 mixture of DMF and water. The reaction mixture was then heated at reflux overnight, allowed to cool to ambient temperature and concentrated under reduced pressure. Water was added to the residue and the solid was collected by filtration. The solid was washed with water and dissolved in methylene chloride. The methylene chloride solution was washed with brine, dried over anhydrous magnesium sulfate, filtered and concentrated in vacuo. The residue (3.67 g) was dissolved in 20 mL of dry THF and the solution was cooled to 0° C. under a nitrogen atmosphere. Potassium t-butoxide (1.9 g, 16.5 mmol) was added and the reaction mixture was stirred at ambient temperature for 1 h. Methyl iodide (1.12 mL, 18 mmol) was then added and the reaction mixture stirred for another hour at ambient temperature. The reaction was quenched by the addition of saturated aqueous ammonium chloride. The aqueous layer was diluted with water and extracted with ethyl acetate. The combined organic layers were dried over anhydrous magnesium sulfate, filtered and concentrated in vacuo to give 1.54 g (34% overall yield from the unsaturated nitrile) of the title compound.

Step 2:
cis-8-Methoxy-2-methyl-1,2,3,4,4a,5,6,10b-octahydro-1-oxo-3-phenylmethyl-benz[f]isoquinoline cis-8-Methoxy-1,3-dioxo-2-methyl-1,2,3,4,4a,5,6,10b-octahydro-benz[f]isoquinoline (1.54 g, 5.9 mmol), from Step 1, was dissolved in 30 mL of THF/diethyl ether 1:1 and the resultant solution was cooled to 0° C. under a nitrogen atmosphere. Benzyl magnesium bromide (4.45 g, 8.9 mmol) was added dropwise over a 20 min period. The reaction mixture was stirred at 0° C. for 1 h and then 1 mL of trifluoroacetic acid (TFA) was added. The reaction mixture was warmed to ~30° C. and the solvent was evaporated with a stream of nitrogen gas. TFA (12 mL) was added to the residue and the solution was cooled to 0° C. Sodium cyanoborohydride (1.12 g, 17.8 mmol) was added in two portions and the reaction mixture was allowed to warm to ambient temperature. The reaction mixture was stirred at ambient temperature for 3 h and the TFA was evaporated by passing a stream of nitrogen through the reaction mixture overnight. The residue was partitioned between methylene chloride and 1N aqueous hydrochloric acid solution (4:1). The aqueous layer was extracted with two portions of methylene chloride. The combined methylene chloride layers were washed with brine, dried over anhydrous magnesium sulfate, filtered and adsorbed onto silica gel. Chromatography sequentially with hexane ethyl acetate in the following proportions; 2:1 followed by 1:1, 1:2, 1:4, and 1:8 afforded 1.04 g of the title compound as a mixture of two isomers.

Step 3:
cis-8-Methoxy-2-methyl-1,2,3,4,4a,5,6,10b-octahydro-3-phenylmethyl-benz[f]isoquinoline hydrochloride 8-Methoxy-2-methyl-1,2,3,4,4a,5,6,10b-octahydro-1-oxo-3-phenylmethyl-benz[f]isoquinoline (0.85 g, 2.53 mmol), from Step 2, was dissolved in 15 mL of dry THF and 5.07 mL of a 1.0M solution of borane in THF (5.07 mmol) was added. The reaction mixture was heated at reflux for 1 h under a nitrogen balloon. The THF was evaporated under reduced pressure. Methanol (30 mL) and methanol saturated with hydrogen chloride (10 mL) were added to the residue and the reaction mixture was heated at reflux for 1 h. The solvent was removed under reduced pressure and the residue was partitioned between 1N aqueous sodium hydroxide solution and methylene chloride (1:4). The aqueous layer was extracted with two portions of methylene chloride. The combined organic layers were dried over anhydrous magnesium sulfate, filtered and adsorbed onto silica gel. Chromatography on silica gel eluted with hexane/diethyl ether saturated with ammonia (2:1) gave 0.55 g (68% yield) of the desired compound. The hydrochloride salt was formed in diethyl ether saturated with hydrogen chloride. The hydrochloride salt was collected by filtration and crystallized from acetone to afford the title compound, m.p. 202°–203.5° C.; MS DCl-isobutane M/Z: 322 (M+H)+, 378 (M+C$_4$H$_9$)+; $^1$H NMR (CDCl$_3$) δ1.18–1.37 (2H, m), 1.61–1.70 (1H, m), 1.74–1.97 (2H, m), 2.17–2.32 (2H, m), 2.41 (3H, s), 2.47 (1H, dd, J=4, 13 Hz), 2.56–2.67 (1H, m), 2.74–2.88 (2H, m), 3.16 (1H, d, J=9 Hz), 3.45 (1H, dd, J=4, 13 Hz), 3.78 (3H, s), 6.62 (1H, d, J=2 Hz), 6.76 (1H, dd, J=2, 8 Hz), 7.10–7.30 (6H, m). Analysis calculated for C$_{22}$H$_{28}$ClNO: C, 73.83; H, 7.89; N, 3.91. Found: C, 73.76; H, 7.91; N, 3.85.

EXAMPLE 73 cis-8-Methoxy-2-methyl-1,2,3,4,4a,5,6,10b-octahydro-3-phenylmethyl-benz[f]isoquinoline hydrochloride Step 1: Methyl 3-oxo-4-phenyl-2-(1-cyano-6-methoxy-1,2,3,4-tetrahydronaphth-2-yl)-butyrate Methyl 3-oxo-4-phenylbutyrate (29.33 g, 153 mmol) and 1-cyano-6-methoxy-3,4-dihydronaphthalene (25.7, 139 mmol), the product of Step 2 of Example 1, were dissolved in 25 mL of acetonitrile. DBU (1.5 mL) was added and the reaction mixture was stirred for 2 h at ambient temperature. A second aliquot of DBU (1.5 mL) was then added and stirring continued overnight. The reaction mixture was partitioned between diethyl ether and 1N aqueous hydrochloric acid solution (4:1) and the aqueous layer was extracted with diethyl ether. The combined organic layers were washed with 1N aqueous hydrochloric acid and brine, dried over anhydrous magnesium sulfate, filtered and concentrated under reduced pressure. The residue was chromatographed on silica gel eluted with hexane/ethyl acetate (6:1) to give 33.9 g (65% yield) of the title compound; MS DCl—NH$_3$ M/Z: 395 (M+NH$_4$)+.

Step 2:
1-Cyano-6-methoxy-2-(2-oxo-3-phenylpropyl)-1,2,3,4-tetrahydronaphthalene Methyl 3-oxo-4-phenyl-2-(1-cyano-6-methoxy-1,2,3,4-tetrahydronaphth-2-yl)-butyrate (4.63 g, 12 mmol), from Step 1, was dissolved in 100 mL of methanol and lithium hydroxide (77 mL of a 1.0M solution) was added. The reaction mixture was stirred overnight at ambient temperature and then acidified with 1N aqueous hydrochloric acid solution and extracted with diethyl ether. The ether extract was washed with brine, dried over anhydrous magnesium sulfate, filtered and concentrated under reduced pressure. The basic ether extract yielded 2.76 (70% yield) of the title compound; MS DCl—NH$_3$ M/Z: 337 (M+H)+.

Step 3:
1-Cyano-2-[1-(1,3-dioxolane)-3-phenylethyl]-6-methoxy-1,2,3,4-tetrahydronaphalene Ethylene glycol (7 mL, 3 equivalents) was added to a solution of 1-cyano-6-methoxy-2-(2-oxo-3-phenylpropyl)-1,2,3,4-tetrahydronaphthalene (11.8 g, 36.9 mmol), from step 2, in 250 mL of toluene. p-Toluenesulfonic acid (5 g) was added and the reaction mixture was heated at reflux for 5 h, cooled to ambient temperature, and then partitioned between 1N aqueous sodium hydroxide solution and diethyl ether (1:4). The aqueous layer was extracted with diethyl ether and the combined organic layers were washed with water, dried over anhydrous magnesium sulfate, filtered and concentrated under reduced pressure. The residue was chromatographed on silica gel eluted with hexane/ethyl acetate (6:1) to give 8.2 g (61% yield) of the title compound; MS DCl—$NH_3$ M/Z: 364 $(M+H)^+$; MS DCl—$NH_3$ M/Z: 381 $(M+NH_4)^+$.

Step 4:
1-Aminomethyl-2-[1-(1,3-dioxolane)-3-phenylethyl]-6-methoxy-1,2,3,4-tetrahydronaphalene 1-Cyano-2-[1-(1,3-dioxolane)-3-phenylethyl]-6-methoxy-1,2,3,4-tetrahydronaphalene (27.4 g, 75.4 mmol), from Step 3 hydrogenated over 55 g of Raney nickel in 50 mL of triethylamine and 450 mL of methanol, according to the procedure described in Step 5 of Example 1. The reaction mixture was filtered and the filtrate concentrated in vacuo. The residue was partitioned between 1N aqueous hydrochloric acid solution and methylene chloride (1:4). The layers were separated and the aqueous layer was extracted with two portions of methylene chloride. The combined organic layers were washed with brine, dried over anhydrous magnesium sulfate, filtered and concentrated under reduced pressure to provide 24.8 g (90% yield) of the title compound which was carried on to the next step; MS DCl—$NH_3$ M/Z: 368 $(M+H)^+$.

Step 5: cis and trans
1-(N-t-Butyloxycarbonylamino)methyl-2-[1-(1,3-dioxolane)-3-phenylethyl]-6-methoxy-1,2,3,4-tetrahydronaphalene 1-Aminomethyl-2-[1-(1,3-dioxolane)-3-phenylethyl]-6-methoxy-1,2,3,4-tetrahydronaphalene (24.8 g, 67.5 mmol) was dissolved in 100 mL of DMF and the resultant solution was cooled to 0° C. under nitrogen. BOC-anhydride (30 g, 135 mmol) was added slowly and the reaction mixture was stirred for 1 h at ambient temperature. The reaction mixture was partitioned between diethyl ether and water (5:1) and the aqueous layer was extracted with two portions of diethyl ether. The combined organic layers were washed twice with water, once with brine, dried over anhydrous magnesium sulfate, filtered and concentrated under reduced pressure. The residue was chromatographed on silica gel eluted with hexane/diethyl ether (4:1 and 2:1) to give a total of 30.4 g (96% yield) of two products. The first compound to elute from the column (73-5A) was the cis isomer: MS DCl—$NH_3$ M/Z: 468 $(M+H)^+$; MS DCl—$NH_3$ M/Z: 485 $(M+NH_4)^+$. The second compound to elute from the column (73-5B) was the trans isomer: MS DCl—$NH_3$ M/Z: 468 $(M+H)^+$; MS DCl—$NH_3$ M/Z: 485 $(M+NH_4)^+$.

Step 6:
cis-8-Methoxy-1,2,3,4,4a,5,6,10b-oxtahydro-3-phenylmethyl-benz[f]isoquinoline cis-1-(N-t-Butyloxycarbonylamino)methyl-2-[1-(1,3-dioxolane)-3-phenylethyl]-6-methoxy-1,2,3,4-tetrahydronaphalene (73-5A; 8.6 g, 18.4 mmol) was dissolved in 50 mL of methylene chloride and trifluoroacetic acid (50 mL) was added. The reaction mixture was stirred at ambient temperature for 0.5 h and then concentrated in vacuo. The residue was partitioned between cold 1N aqueous sodium hydroxide solution and diethyl ether (1:5) and the aqueous layer was extracted with two portions of diethyl ether. The combined organic layers were dried over anhydrous magnesium sulfate, filtered and concentrated under reduced pressure to give 5.5 g (98% yield) of the imine intermediate. The imine was dissolved in 100 mL of methanol and sodium cyanoborohydride (3.5 g, 55 mmol) was added portionwise. Methanolic hydrogen chloride was added to maintain the pH of the reaction mixture at approximately 3. After the addition was complete, the reaction mixture was stirred at ambient temperature for 1 h and then acidified with methanolic hydrogen chloride to quench the excess sodium cyanoborohydride. The reaction mixture was concentrated under reduced pressure and the residue was partitioned between 1N aqueous sodium hydroxide and methylene chloride (1:4). The aqueous layer was extracted with two portions of methylene chloride and the combined organic layers were dried over anhydrous magnesium sulfate, filtered and suspended on silica gel. The product coated on silica gel was chromatographed on silica gel eluted with ethyl acetate/water/formic acid (19:0.5:0.5 followed by 18:1:1) to give the two diastereomeric title compounds in 90% total yield (5 g). The first compound to elute from the column (73-6A) was the cis-anti isomer: MS DCl—$NH_3$ M/Z: 308 $(M+H)^+$; $^1H$ NMR (CDCl3) δ1.49–1.59 (m, 1H), 1.68–1.75 (m, 2H), 1.77 (bs, 1H), 2.01–2.21 (m, 2H), 2.55 (dd, 1H, J=8, 14 Hz), 2.63–3.00 (m, 7H), 3.75 (s, 3H), 6.59 (d, 1H, J=2 Hz), 6.67 (dd, 1H, J=2, 8 Hz), 7.00 (d, 1H, J=8 Hz), 7.19–7.35 (m, 5H). The second compound to elute from the column (73-6B) was the cis-syn isomer; MS DCl—$NH_3$ M/Z: 308 $(M+H)^+$; $^1H$ NMR (CDCl3) δ1.06–1.20 (m, 1H), 1.38–1.47 (m, 1H), 1.64–1.74 (m, 1H), 1.81–1.95 (m, 1H), 2.02–2.13 (m, 1H), 2.45 (dd, 1H, J=8, 14 Hz), 2.61–2.93 (m, 6H), 2.96 (dd, 1H, J=4, 13 Hz), 3.74–3.82 (m, 1H), 3.79 (s, 3H), 6.65 (d, 1H, J=2 Hz), 6.77 (dd, 1H, J=2, 8 Hz), 7.11–7.31 (m, 6H).

Step 7:
1-(N-(+)-Menthylcarbonylamino)methyl-2-[(1-(1,3-dioxolane)-3-phenylethyl]-6-methoxy-1,2,3,4-tetrahydronaphalene cis/anti-8-Methoxy-2-methyl-1,2,3,4,4a,5,6,10b-octahydro-3-phenylmethyl-benz[f]isoquinoline (73-6A; 1.0 g, 3.3 mmol) was dissolved in 25 mL of methylene chloride and the resultant solution was cooled to 0° C. under nitrogen. Triethylamine (0.91 mL, 6.5 mmol) was added, followed by (+) menthyl chloroformate (1.05 mL, 4.9 mmol) and the reaction mixture was stirred overnight at ambient temperature under a nitrogen atmosphere. The reaction mixture was then partitioned between 1N aqueous sodium hydroxide solution and diethyl ether (1:5). The organic layer was dried over anhydrous magnesium sulfate, filtered and concentrated under reduced pressure. The residue was chromatographed on silica gel eluted with hexane/diethyl ether (5:1). The first compound to elute from the column (73-7A) was recrystallized from methylene chloride/hexane to give (3S, 4aR, 10aS) isomer of the title compound:; MS DCl—$NH_3$ M/Z: 490 $(M+H)^+$; MS DCl—$NH_3$ M/Z: 507 $(M+NH_4)^+$. The second compound to elute from the column was a mixture of the (3S, 4aR, 10aS) isomer and the (3R, 4aS, 10aR) isomer of the title compound. In order to obtain the (3S, 4aR, 10aS) isomer the above reaction was repeated using (−) menthyl chloroformate to give the desired isomer as the first compound to elute from the column (73-7B) in 38% yield (0.62 g).

Step 8: (+) and (−) cis-8-Methoxy-2-methyl-1,2,3,4,4a,5,6,10b-octahydro-3-phenylmethyl-benz[f]isoquinoline hydrochloride To a solution of 1-(N-(+)menthylcarbonylamino)-methyl-2-[1-(1,3-dioxolane)-3-phenylethyl]-6-methoxy-1,2,3,4-tetrahydronaphalene (73-7A: 570 mg, 1.2 mmol) in 50 mL of THF was added lithium aluminum hydride (220 mg, 5.8 mmol) and the reaction mixture was heated to reflux under nitrogen. The reaction mixture was heated at reflux for 2 h and then cooled to 0° C. The reaction was quenched by the careful sequential addition of 250 μL of water, 250 μL of 4N aqueous sodium hydroxide solution and 750 μL of water and stirred for 1 h at ambient temperature. The suspension was filtered, the solid was washed with THF and the filtrate was concentrated in vacuo. The residue was suspended in silica gel and chromatographed on silica gel eluted with ethyl acetate/water/formic acid (18:1:1). The product was partitioned between 1N aqueous sodium hydroxide and ethyl acetate (1:4) and the ethyl acetate solution was dried over anhydrous magnesium sulfate, filtered and concentrated to give the free amine of the title compound. The free amine product was converted to its hydrochloride salt which is recrystallized from acetone/diethyl ether to give the title compound (73-8A), m.p. 198°-199° C.; $[\alpha]_D^{23} -22.4°$ (c 1.16; $CH_3OH$); MS DCl—$NH_3$ M/Z: 322 (M+H)+. Analysis calculated for $C_{22}H_{28}ClNO$: C, 73.83; H, 7.89; N, 3.91. Found: C, 73.62; H, 7.85; N, 3.86.

The above procedure was repeated for 73-7B to give the (+) isomer of the title compound: $[\alpha]_D^{23} +22.4°$ (c 1.16; $CH_3OH$); MS DCl—$NH_3$ M/Z: 322 (M+H)+. Analysis calculated for $C_{22}H_{28}ClNO$: C, 73.83; H, 7.89; N, 3.91. Found: C, 72.96; H, 7.76; N, 3.83.

EXAMPLE 74 trans8-Methoxy-2-methyl-1,2,3,4,4a,5,6,10b-octahydro-3-phenylmethyl-benz[f]isoquinoline hydrochloride

Step 1:
trans/syn-8-Methoxy-2-methyl-1,2,3,4,4a,5,6,10b-octahydro-3-phenylmethyl-benz[f]isoquinoline A solution of 1-(N-t-butyloxycarbonylamino)methyl-2-[1-(1,3-dioxolane)-3-phenylethyl]-6-methoxy-1,2,3,4-tetrahydronaphalene, (73-5B; 19.1 g, 40.9 mmol) in 100 mL of methylene chloride was cooled to 0° C. and trifluoroacetic acid (50 mL) was added. The reaction mixture was stirred at ambient temperature for 1 h and then concentrated under reduced pressure. The residue was partitioned between 1N aqueous sodium hydroxide solution and diethyl ether (1:5) and the aqueous layer was extracted with three portions of diethyl ether. The combined organic layers were washed with brine, dried over anhydrous magnesium sulfate, filtered and suspended on silica gel. The product adsorbed on silica gel was chromatographed on silica gel eluted with ethyl acetate/water/formic acid (28:1:1) to give 7.1 g of the intermediate trans imine as the first compound to elute from the column. The imine was dissolved in 200 mL of methanol and sodium cyanoborohydride (4.4 g, 70 mmol) was added portionwise, maintaining the pH of the reaction mixture at approximately 3 using methanolic hydrogen chloride. After the addition was complete, the reaction mixture was stirred for 0.5 h and concentrated in vacuo. The residue was partitioned between methylene chloride and 1N aqueous sodium hydroxide solution (4:1) and the aqueous layer was extracted with two portions of methylene chloride. The combined organic layers were washed with brine, dried over anhydrous magnesium sulfate, filtered through Celite® filter aid and concentrated under reduced pressure to give 6.9 g (97% yield) of the trans-syn product; MS DCl—$NH_3$ M/Z: 308; $^1H$ NMR ($CDCl_3$) δ1.12-1.29 (m, 1H), 1.32-1.47 (m, 1H), 1.47-1.63 (m, 1H), 1.70-1.85 (m, 2H), 2.40-2.50 (m, 2H), 2.62-3.01 (m, 8H), 3.67-3.74 (m, 1H), 3.76 (s, 3H), 6.73 (d, 1H, J=2 Hz), 6.78 (dd, 1H, J=2, 8 Hz), 7.06 (d, 1H, J=8 Hz), 7.19-7.36 (m, 5H).

Step 2: (−)
trans8-Methoxy-2-methyl-1,2,3,4,4a,5,6,10b-octahydro-3-phenylmethyl-benz[f]isoquinoline hydrochloride Following the procedure described above in Step 7 of Example 73, the product of Step 1 of this Example was treated with (+) menthyl chloroformate to give the desired diastereomeric carbamates. The carbamate was reduced by the procedure described in Step 8 of Example 73 to afford the (−) isomer of the title compound as the first compound to elute from the column: m.p. 218.5°-221° C.; $[\alpha]_D^{23} -47.8°$ (c 0.965; $CH_3OH$). Analysis calculated for $C_{22}H_{28}ClNO$: C, 73.83; H, 7.89; N, 3.91. Found: C, 73.62; H, 7.78; N, 4.01.

EXAMPLE 75

2-Methyl-1,3,4,5,5a,6,7,11b-octahydro-3-phenylmethyl-2H-naphth[1,2-c]azepine hydrochloride

Step 1:
2-(2-Ethoxycarbonylethyl)-3,4-dihydro-1(2H)-naphthalenone

α-Tetralone (20 g, 137 mmol), commercially available from Aldrich Chemical Company, was combined with 200 mL of toluene, 30 mL of pyrrolidine and a catalytic amount of p-toluenesulfonic acid and the reaction mixture was heated at reflux for 4 days. The reaction mixture was concentrated in vacuo and 300 mL of absolute ethyl alcohol and 25 mL of ethyl acrylate were added to the residue. The reaction mixture was heated at reflux for 3 h and then 100 mL of water was added and reflux continued for 1 h. The reaction mixture was concentrated in vacuo and the residue was partitioned between dilute aqueous hydrochloric acid and ethyl acetate (1:5). The organic layer was dried over anhydrous magnesium sulfate, filtered and concentrated in vacuo. The residue was purified by chromatography on silica gel eluted with 10% ethyl acetate in hexane to give 19.7 g (59% yield) of the title compound; MS DCl—$NH_3$ M/Z: 247 (M+H)+, 264 (M+$NH_4$)+.

Step 2:
1-Cyano-2-(2-ethoxycarbonylethyl)-3,4-dihydronaphthalene 2-(2-Ethoxycarbonylethyl)-3,4-dihydro-1(2H)-naphthalenone (19.7 g, 80 mmol), from Step 1, was dissolved in 200 mL of dry THF and diethyl cyanophosphonate (23.6 mL, 160 mmol), commercially available from Aldrich Chemical Company, was added, followed by 160 mL of a 0.5M solution of lithium cyanide in DMF. The reaction mixture was stirred at ambient temperature overnight and then poured into water. The aqueous mixture was extracted with three portions of diethyl ether. The ether extracts were dried over anhydrous magnesium sulfate, filtered and concentrated under reduced pressure. The residue was dissolved in 400 mL of toluene and 20 g of p-toluenesulfonic acid was added.

The reaction mixture was heated at reflux for 3 h and allowed to cool to ambient temperature. The toluene solution was washed with 5% aqueous sodium bicarbonate, dried over anhydrous magnesium sulfate, filtered and concentrated in vacuo. The residue was purified by chromatography on silica gel eluted with 10% ethyl acetate in hexane to give 13.1 g (64.2% yield) of the title compound; MS DCl—NH3 M/Z: 273 $(M+NH_4)^+$.

Step 3:
1,3,4,5,5a,6,7,11b-octahydro-3-oxo-2H-naphth[1,2-c]azepine

1-Cyano-2-(2-ethoxycarbonylethyl)-3,4-dihydronaphthalene (13 g, 51 mmol) was dissolved in 300 mL of ethyl alcohol. Raney nickel #28 (26 g) was added and the reaction mixture was heated to 50° C. and shaken under 4 atmospheres of hydrogen for 18 h. The catalyst was removed by filtration and the filtrate was concentrated in vacuo. Ethyl acetate/hexane (1:1) was added to the residue and a solid precipitated. The solid was collected by filtration to give 2.53 g of the cis isomer of the product as white crystals, m.p. 210° C.; MS DCl—NH3 M/Z: 216 $(M+H)^+$, 233 $(M+NH_4)^+$; $^1$H NMR (CDCl$_3$) δ155-2.13 (4H, m), 2.2-2.46 (2H, m), 2.58-2.73 (1H, m), 2.74-3.2 (4H, m), 3.62-3.77 (1H, m), 5.9 (1H, bs), 7.03-7.33 (4H, m).

The filtrate was concentrated in vacuo and 150 mL of xylene and a catalytic amount of p-toluenesulfonic acid were added to the residue. The resultant solution was heated at reflux overnight. The solvent was evaporated and the residue was triturated with ethyl acetate/hexane (1:1) to give 6 g (55% yield) of the trans isomer of the product as white crystals, m.p. 154°-156° C.; MS DCl—NH3 M/Z: 216 $(M+H)^+$, 233 $(M+NH_4)^+$ $^1$H NMR (CDCl$_3$) δ1.46-1.76 (4H, m), 1.78-2.02 (2H, m), 2.52-3.02 (4H, m), 3.33-3.44 (1H, m), 3.73-3.84 (1H, m), 6.08 (1H, bs), 7.07-7.35 (4H, m).

Step 4:
cis-2-Methyl-1,3,4,5,5a,6,7,11b-octahydro-3-oxo-2H-naphth[1,2-c]azepine cis-2-Methyl-1,3,4,5,5a,6,7,11b-octahydro-3-oxo-2H-naphth[1,2-c]azepine (2.53 g, 11.76 mmol), from Step 3, was suspended in 50 mL of dry THF and 1.98 g of potassium t-butoxide was added. The reaction mixture was stirred at ambient temperature for 0.5 h and then 2.5 mL of methyl iodide was added. The reaction mixture was stirred at ambient temperature for 1 h and then it was poured into water. The aqueous mixture was extracted with ethyl acetate. The combined organic layers were washed with brine, dried over anhydrous magnesium sulfate, filtered and concentrated in vacuo to give 2.35 g (87% yield) of the title compound, m.p. 130°-131° C.; MS DCl—NH3 M/Z: 230 $(M+H)^+$, 247 $(M+NH_4)^+$.

Step 5:
cis-2-Methyl-1,3,4,5,5a,6,7,11b-octahydro-3-phenylmethyl-2H-naphth[1,2-c]azepine hydrochloride 2-Methyl-1,3,4,5,5a,6,7,11b-octahydro-3-oxo-2H-naphth[1,2-c]azepine (1.37 g, 6 mmol), from Step 4, was dissolved in 30 mL of 1:1 THF:diethyl ether and the resultant solution was cooled to 0° C. Benzylmagnesium bromide (4.55 mL of a 2.0M solution in THF, 1.5 equivalents), commercially available from Aldrich Chemical Company, was added and the reaction mixture was stirred at 0° C. for 45 min. The reaction was then quenched by the addition of saturated aqueous ammonium chloride and the aqueous mixture was extracted with methylene chloride. The organic layer was dried over anhydrous magnesium sulfate, filtered and concentrated under reduced pressure. The residue was dissolved in methanol and 1.5 g of sodium cyanoborohydride was added portionwise. The pH of the reaction mixture was adjusted to 5 by the addition of methanol saturated with hydrogen chloride. After 20 min the pH was again adjusted to 5 by the addition of methanol saturated with hydrogen chloride. After 2 h, methanol was added to quench the excess sodium cyanoborohydride. The solvent was evaporated in vacuo and the residue was partitioned between 2N sodium hydroxide and methylene chloride. The methylene chloride solution was dried over anhydrous magnesium sulfate, filtered and evaporated under reduced pressure. The residue was purified by chromatography on silica gel eluted with 10% ethyl acetate in hexane saturated with ammonium hydroxide to give a total of 1.13 g (62% yield) of the two isomeric products which were converted to their hydrochloride salts in diethyl ether saturated with hydrogen chloride.

The first compound to elute from the column (75A) was 0.28 g of the cis/syn isomer, m.p. 125°-128° C.; MS DCl—NH3 M/Z: 306 $)M+H)^+$; $^1$H NMR (CDCl$_3$) δ1.42-1.93 (6H, m), 2.0-2.12 (1H, m), 2.37-2.52 (1H, m), 2.58 (1H, d, J=18.0 Hz), 2.7 (3H, s), 2.75-2.93 (4H, m), 3.12-3.22 (1H, m), 3.25-3.37 (1H, m), 7.02-7.32 (9H, m). Analysis calculated for $C_{22}H_{28}ClN+0.25H_2O$: C, 76.30; H, 8.09; N, 4.04. Found: C, 76.27; H, 7.66; N, 4.07.

The second compound to elute from the column (75B) was the cis/anti isomer (0.85 g), m.p. 228°-230° C.; MS DCl—NH3 M 306 $(M+H)^+$; $^1$H NMR (CDCl$_3$) δ1.3-1.74 (5H, m), 1.92-2.04 (2H, m), 2.35-2.6 (3H, m), 2.6 (3H, s), 2.76-2.89 (2H, m), 2.96-3.0 (2H, m), 3.23-3.31 (1H, m), 3.81 (3H, s), 6.65 (1H, d, J=9 Hz), 6.9 (1H, d, J=9 Hz), 7.1-7.33 (9H, m). Analysis calculated for $C_{22}H_{28}ClN$: C, 77.31; H, 8.09; N, 4.10. Found: C, 77.22; H, 8.32; N, 4.01.

EXAMPLE 76

8-Methoxy-2-methyl-1,3,4,5,5a,6,7,11b-octahydro-3-phenylmethyl-2H-naphth[1,2-c]azepine hydrochloride Step 1:
2-(2-Ethoxycarbonylethyl)-3,4-dihydro-5-methoxy-1(2H)-naphthalenone 5-Methoxy-α-Tetralone (20 g, 113 mmol), commercially available from Aldrich Chemical Company, was combined with 400 mL of toluene, 30 mL of pyrrolidine and a catalytic amount of p-toluenesulfonic acid and the reaction mixture was heated at reflux over molecular sieves for 72. The reaction mixture was concentrated in vacuo and 300 mL of absolute ethyl alcohol and 20 mL of ethyl acrylate were added to the residue. The reaction mixture was heated at reflux for 4 h and then 100 mL of water was added and reflux continued for 1 h. The reaction mixture was concentrated in vacuo and the residue was partitioned between dilute aqueous hydrochloric acid and ethyl acetate (1:5). The organic layer was dried over anhydrous magnesium sulfate, filtered and concentrated in vacuo. The residue was purified by chromatography on silica gel eluted with 10% ethyl acetate in hexane to give 14.37 g (46% yield) of the title compound; MS DCl—NH3 M/Z: 277 $(M+H)^+$, 294 $(M+NH_4)^+$.

Step 2:
1-Cyano-2-(2-ethoxycarbonylethyl)-5-methoxy-3,4-dihydronaphthalene 2-(2-Ethoxycarbonylethyl)-3,4-dihydro-5-methoxy-1(2H)-naphthalenone (1.1 g, 4 mmol), from Step 1, was dissolved in 15 mL of dry THF and cooled to 0° C. Diethyl cyanophosphonate (1.18 mL, 8 mmol), commercially available from Aldrich Chemical Company, was added, followed by 8 mL of a 0.5M solution of lithium cyanide (4 mmol) in DMF. The reaction mixture was stirred at ambient temperature overnight and then poured into water. The aqueous mixture was extracted with three portions of diethyl ether/ethyl acetate. The organic extracts were washed with brine, dried over anhydrous magnesium sulfate, filtered and concentrated under reduced pressure. The residue was dissolved in 100 mL of toluene and 1.1 g of p-toluenesulfonic acid was added. The reaction mixture was heated at reflux for 2 h and allowed to cool to ambient temperature. The toluene solution was poured into 5% aqueous sodium bicarbonate and the aqueous mixture was extracted with ethyl acetate. The combined organic layers were dried over anhydrous magnesium sulfate, filtered and concentrated in vacuo. The residue was purified by chromatography on silica gel eluted with 10% ethyl acetate in hexane to give 0.8 g (70% yield) of the title compound; MS DCl—NH3 M/Z: 286 $(M+H)^+$, 303 $(M+NH_4)^+$.

Step 3:
8-Methoxy-2-methyl-1,3,4,5,5a,6,7,11b-octahydro-3-oxo-2H-naphth[1,2-c]azepine 1-Cyano-2-(2-ethoxycarbonylethyl)-5-methoxy-3,4-dihydronaphthalene (9.8 g, 34.39 mmol) was dissolved in 250 mL of ethyl alcohol. Raney nickel (19.6 g) was added and the reaction mixture was heated to 50° C. and shaken under 4 atmospheres of hydrogen for 18 h. The catalyst was removed by filtration and the filtrate was concentrated in vacuo. 20% Ethyl acetate in hexane was added to the residue and a solid precipitated. The solid was collected by filtration to give 2.6 g of white crystals. The filtrate was concentrated in vacuo and xylene and a catalytic amount of p-toluenesulfonic acid were added to the residue. The resultant solution was heated at reflux for 16 h. The solvent was evaporated in vacuo and the residue was crystallized from ethyl acetate/hexane (1:1) to give 2.72 g of white crystals, m.p. 182°-184° C.; MS DCl—NH3 M/Z: 246 $(M+H)^+$, 263 $(M+NH_4)^+$. The crystals were combined (62% total yield) and carried on to the next step.

Step 4:
8-Methoxy-2-methyl-1,3,4,5,5a,6,7,11b-octahydro-3-oxo-2H-naphth[1,2-c]azepine 8-Methoxy-2-methyl-1,3,4,5,5a,6,7,11b-octahydro-3-oxo-2H-naphth[1,2-c]azepine (5.31 g, 21.67 mmol), from Step 3, was suspended in 100 mL of dry THF and 3.64 g (1.5 equivalents) of potassium t-butoxide was added. The reaction mixture was stirred at ambient temperature for 0.5 h and then 5 mL of methyl iodide was added. The reaction mixture was stirred at ambient temperature for 1 h and then it was poured into water. The aqueous mixture was extracted with ethyl acetate. The combined organic layers were washed with brine, dried over anhydrous magnesium sulfate, filtered and concentrated in vacuo to give 5.25 g (94% yield) of the title compound, m.p. 123°-124° C.; MS DCl—NH3 M/Z: 260 $(M+H)^+$, 277 $(M+NH_4)^+$.

Step 5:
8-Methoxy-2-methyl-1,3,4,5,5a,6,7,11b-octahydro-3-phenylmethyl-2H-naphth[1,2-c]azepine hydrochloride 8-Methoxy-2-methyl-1,3,4,5,5a,6,7,11b-octahydro-3-oxo-2H-naphth[1,2-c]azepine (0.51 g, 2 mmol), from Step 4, was dissolved in 50 mL of 1:1 THF:diethyl ether and the resultant solution was cooled to 0° C. Benzylmagnesium bromide (1.5 mL of a 2.0M solution in THF, 1.5 equivalents), commercially available from Aldrich Chemical Company, was added and the reaction mixture was stirred at 0° C. for 1.5 h. The reaction was then quenched by the addition of saturated aqueous ammonium chloride and the aqueous mixture was extracted with methylene chloride. The organic layer was dried over anhydrous magnesium sulfate, filtered and concentrated under reduced pressure. The residue was dissolved in methanol and 0.9 g of sodium cyanoborohydride was added portionwise. The pH of the reaction mixture was adjusted to 5 by the addition of methanol saturated with hydrogen chloride. After 10 min the pH was again adjusted to 5 by the addition of methanol saturated with hydrogen chloride. After 2 h at 0° C., methanol was added to quench the excess sodium cyanoborohydride. The solvent was evaporated in vacuo and the residue was partitioned between 1N aqueous sodium hydroxide and methylene chloride (1:5). The methylene chloride solution was dried over anhydrous magnesium sulfate, filtered and evaporated under reduced pressure. The residue (0.82 g) was purified by chromatography on silica gel eluted with 10% ethyl acetate in hexane saturated with ammonium hydroxide to give a total of 0.82 g (62% yield) of the two isomeric products which were converted to their hydrochloride salts in diethyl ether saturated with hydrogen chloride. The first compound to elute from the column (76A) was 0.08 g of the cis/syn isomer; MS DCl—NH3 M/Z: 336 $(M+H)^+$; $^1$H NMR (CDCl$_3$) δ1.42-1.87 (6H, m), 1.95-2.07 (1H, m), 2.37-2.52 (2H, m), 2.61 (1H, d, J=18.0 Hz), 2.7 (3H, s), 2.75-2.93 (3H, m), 3.11-3.18 (1H, m), 3.27-3.37 (1H, m), 3.81 (3H, s), 6.64 (1H, d, J=9 Hz), 6.75 (1H, d, J=9 Hz), 7.09-7.2 (6H, m). Analysis calculated for C$_{23}$H$_{29}$ClNO: C, 74.29; H, 8.07; N, 3.774. Found: C, 74.13; H, 8.21; N, 3.67. The final compound to elute from the column was the cis/anti isomer (76B); MS DCl—NH3 M/Z: 336 $(M+H)^+$; $^1$H NMR (CDCl$_3$) δ1.34-1.74 (5H, m), 1.92-2.12 (2H, m), 2.49-2.63 (4H, m), 2.6 (3H, s), 2.69-2.84 (3H, m), 2.96-3.12 (2H, m), 3.24-3.33 (1H, m), 7.03-7.34 (9H, m). Analysis calculated for C$_{23}$H$_{29}$ClNO+0.25H$_2$O: C, 73.40; H, 7.98; N, 3.72. Found: C, 73.45; H, 8.15; N, 3.65.

EXAMPLE 77

(+)-cis-2-Methyl-1,3,4,5,5a,6,7,11b-octahydro-3-phenylmethyl-2H-naphth[1,2-c]azepine hydrochloride

Step 1:
cis-2-Benzyl-1,3,4,5,5a,6,7,11b-octahydro-3-oxo-2H-naphth[1,2-c]azepine To a suspension of cis-1,3,4,5,5a,6,7,11b-octahydro-3-oxo-2H-naphth[1,2-c]azepine (1.0 g, 4.65 mmol), from Step 3 of Example 75, in 20 mL of dry THF, was added potassium t-butoxide (0.78 g, 6.9 mmol). The reaction mixture was stirred at ambient temperature for 0.5 h and then cooled to 0° C. and benzyl bromide (0.8 mL, 6.7 mmol) was added. The reaction mixture was allowed to warm to ambient temperature, stirred for 3 h and then poured into water and extracted three times with ethyl acetate. The combined organic layers were dried over anhydrous magnesium sulfate, filtered and concentrated in vacuo. The residue was crystalized from ether/hexane to afford 1.1 g (79% yield) of the title compound, m.p. 114°-115° C.; MS DCl—NH$_3$ M/Z: 306 (M+H)$^+$; $^1$H NMR (CDCl$_3$) δ1.5-2.2 (5H, m), 2.42-2.54 (1H, m), 2.58-3.03 (5H, m), 3.79 (1H, dd, J=9.5, 13.6 Hz), 4.44 (1H, d, J=13.6 Hz), 4.95 (1H, d, J=13.6 Hz), 6.47-6.5 (1H, m), 6.97-7.45 (8H, m).

Step 2:
cis-2-Benzyl-1,3,4,5,5a,6,7,11b-octahydro-3-phenylmethyl-2H-naphth[1,2-c]azepine hydrochloride cis-2-Benzyl-1,3,4,5,5a,6,7,11b-octahydro-3-oxo-2H-naphth[1,2-c]azepine (3.5 g, 11.48 mmol), from Step 1, was dissolved in 60 mL of THF and the resultant solution was cooled to 0° C. Benzyl magnesium chloride (11.4 mL of a 2.0M solution in THF, 22.8 mmol), commercially available from Aldrich Chemical Company, was added and the reaction mixture was stirred at 0° C. for 2 h. The reaction was quenched by the addition of ammonium chloride and the reaction mixture was extracted with methylene chloride. The combined methylene chloride extract was dried over anhydrous magnesium sulfate, filtered and concentrated in vacuo. Methanol (50 mL) was added, followed by sodium cyanoborohydride (2.4 g, 39 mmol), added portionwise. The pH of the reaction mixture was maintained between 3 and 5 by the addition of methanolic hydrochloric acid. The reaction mixture was stirred overnight. The solvent was removed in vacuo and the residue was partitioned between 1N aqueous sodium hydroxide solution and ethyl acetate (1:4). The aqueous layer was extracted with 2×200 mL of ethyl acetate. The combined organic layers were dried over anhydrous magnesium sulfate, filtered and concentrated in vacuo. The residue was purified by chromatography on silica gel eluted with hexane/ethyl acetate (40:1) to give the title compound. The product was crystallized from ethanol, m.p. 232°-233° C.; MS DCl—NH$_3$ M/Z: 382 (M+H)$^+$; $^1$H NMR (CDCl$_3$) δ1.47-1.86 (5H, m), 1.98-2.1 (2H, m), 2.63-2.93 (6H, m), 3.05-3.15 (2H, m), 3.6 (1H, d, J=13.6 Hz), 4.12 (1H, d, J=13.6 Hz), 6.57-6.63 (1H, d, J=6.8 Hz), 6.89-7.4 (13H, m). Analysis calculated for C$_{20}$H$_{32}$ClN: C, 80.48; H, 7.66; N, 3.35. Found: C, 80.51; H, 7.95; N, 3.28.

Step 3:
cis-1,3,4,5,5a,6,7,11b-Octahydro-3-phenylmethyl-2H-naphth[1,2-c]azepine hydrochloride cis-2-Benzyl-1,3,4,5,5a,6,7,11b-octahydro-3-phenylmethyl-2H-naphth[1,2-c]azepine hydrochloride (2.75 g, 6.58 mmol), from Step 2, was dissolved in 150 mL of methanol and hydrogenated (4 atmospheres H$_2$) over 20% palladium on carbon (0.3 g) at ambient temperature for 24 h. The catalyst was removed by filtration and the filtrate was concentrated under reduced pressure to give 1.65 g (77% yield) of the title compound, which was used in the next step without purification.

Step 4:
cis-2-((−)-Menthyloxycarbonyl)-1,3,4,5,5a,6,7,11b-octahydro-3-phenylmethyl-2H-naphth[1,2-c]azepine To a solution of cis-1,3,4,5,5a,6,7,11b-octahydro-3-phenylmethyl-2H-naphth[1,2-c]azepine hydrochloride (1.3 g, 4.47 mmol) in 50 mL of methylene chloride was added (−) menthylchloroformate (1.47 g, 6.72 mmol) (commercially available from Aldrich Chemical Company) and 1.1 mL of pyridine. The reaction mixture was stirred at ambient temperature for 1 h and then it was poured into water. The organic layer was dried over anhydrous magnesium sulfate, filtered and concentrated in vacuo. The residue was chromatographed on silica gel eluted with hexane/diethyl ether (20:1) to give the title compound as two diastereomers. The first diastereomeric compound (4A) to be eluted from the column was collected in 43% yield (0.9 g). The second compound to be eluted from the column (0.9 g) was rechromatographed on silica gel eluted with hexane/diethyl ether (30:1) to afford 0.68 g (33% yield) of the other diastereomer (4B).

Step 5: (+)
cis-2-Methyl-1,3,4,5,5a,6,7,11b-octahydro-3-phenylmethyl-2H-naphth[1,2-c]azepine hydrochloride cis-2-((−)-Methyloxycarbonyl)-1,3,4,5,5a,6,7,11b-octahydro-3-phenylmethyl-2H-naphth[1,2-c]azepine (0.7 g, 1.48 mmol), from Step 4—compound 4A), was dissolved in 70 mL of toluene. To the resultant solution was added 0.58 g (14.8 mmol) of lithium aluminum hydride and the reaction mixture was heated at reflux for 1.5 h. The reaction mixture was cooled to 0° C. and the reaction was quenched by the sequential addition of 0.58 mL of water, 0.58 mL of 15% aqueous sodium hydroxide solution and 1.74 mL of water. The resultant granular precipitate was stirred at ambient temperature for 1 h and then filtered through a pad of Celite ® filter aid. The filtrate was concentrated and then converted to the hydrochloride salt by treatment with hydrogen chloride in diethyl ether. The solid was filtered and crystallized from ethanol/water to give the title compound, m.p. 205°-207° C.; MS DCl—NH$_3$ M/Z: 306 (M+H)$^+$; $^1$H NMR (CDCl$_3$) δ1.32-1.76 (6H, m), 1.92-2.1 (2H, m), 2.47-2.87 (7H, m), 2.95-3.15 (2H, m), 3.24-3.35 (1H, m), 7.01-7.37 (9H, m). Analysis calculated for C$_{22}$H$_{28}$ClN.0.5H$_2$O: C, 75.32; H, 8.27; N, 3.99. Found: C, 75.78; H, 8.35; N, 4.17.

EXAMPLE 78

(−)
2-Methyl-1,3,4,5,5a,6,7,11b-octahydro-3-phenylmethyl-2H-naphth[1,2-c]azepine hydrochloride Following the procedures described in Step 5 of Example 77, compound 4B from Step 4 of Example 77 was reduced to afford the title compound. The title compound was recrystallized from acetone/diethyl either to give 0.2 g of pure title compound, m.p. 206°-208° C.; MS DCl—NH$_3$ M/Z: 306 (M+H)$^+$; $^1$H NMR (CDCl$_3$) δ1.32-1.76 (6H, m), 1.92-2.1 (2H, m), 2.47-2.87 (7H, m), 2.95-3.15 (2H, m), 3.24-3.35 (1H, m), 7.01-7.37 (9H, m). Analysis calculated for C$_{22}$H$_{28}$ClN.0.5H$_2$O: C, 77.30; H, 8.20; N, 4.04. Found: C, 77.05; H, 8.27; N, 4.04.

EXAMPLE 79 trans-2-Methyl-1,3,4,5,5a,6,7,11b-octahydro-3-phenylmethyl-2H-naphth[1,2-c]azepine hydrochloride Step 1:
trans-2-Methyl-1,3,4,5,5a,6,7,11b-octahydro-3-oxo-2H-naphth[1,2-c]azepine Following the procedures described in Step 4 of Example 75. The trans isomer of the product of Step 3 of Example 75 (2.5 g, 11.5 mmol) was methylated to give 2.47 g (94% yield) of the title compound as an off-white solid.

Step 2:
trans-2-Methyl-1,3,4,5,5a,6,7,11b-octahydro-3-phenylmethyl-2H-naphth[1,2-c]azepine hydrochloride Following the procedures described in Step 5 of Example 75, trans-2-methyl-1,3,4,5,5a,6,7,11b-octahydro-3-oxo-2H-naphth[1,2-c]azepine, from Step 1 above, was converted to a total of 1.82 g (65% yield) of two isomeric products which were converted to their hydrochloride salts in diethyl ether saturated with hydrogen chloride.

The first compound to elute from the column (78A) was 988 mg of the trans/syn isomer, m.p. 213°–215° C.; MS DCl—$NH_3$ M/Z: 306 $(M+H)^+$. Analysis calculated for $C_{22}H_{28}ClN$: C, 77.28; H, 8.25; N, 4.10. Found: C, 77.25; H, 8.19; N, 4.01.

The second compound to elute from the column was rechromatographed on silica gel eluted with 10% ethyl acetate in hexane saturated with ammonium hydroxide and converted to the hydrochloride salt in diethyl ether to give (78B) the trans/anti isomer (483 mg), m.p. 186°–187° C.; MS DCl—$NH_3$ M/Z: 306 $(M+H)^+$. Analysis calculated for $C_{22}H_{28}ClN$: C, 77.28; H, 8.25; N, 4.10. Found: C, 76.90; H, 8.20; N, 4.02.

EXAMPLES 80–105

By following the synthetic methods outlined in reaction scheme I A and reaction scheme I B, the following compounds (Example 80–105) can be prepared starting with 6-trifluoromethyl-α-tetralone or 7-trifluoromethyl-α-tetralone (B. R. Vogt, U.S. Pat. No. 4,051,248, issued Sep. 27, 1977) and using the procedures described in the cited examples.

Examples 80–85 listed below are prepared in accordance with the procedures described in Examples 1, 2 and 3.

80) cis/trans 2,3,3a,4,5,9b-Hexahydro-3-phenylmethyl-6-trifluoromethyl-1H-benz[e]isoindole hydrochloride;
81) cis-2,3,3a,4,5,9b-Hexahydro-2-methyl-3-phenylmethyl-6-trifluoromethyl-1H-benz[e]isoindole methanesulfonic acid salt;
82) cis-2-Ethyl-2,3,3a,4,5,9b-hexahydro-3-phenylmethyl-6-trifluoromethyl-1H-benz[e]isoindole methanesulfonate salt;
83) cis/trans 2,3,3a,4,5,9b-Hexahydro-3-phenylmethyl-7-trifluoromethyl-1H-benz[e]isoindole hydrochloride;
84) cis-2,3,3a,4,5,9b-Hexahydro-2-methyl-3-phenylmethyl-7-trifluoromethyl-1H-benz[e]isoindole methanesulfonic acid salt;
85) cis-2-Ethyl-2,3,3a,4,5,9b-hexahydro-3-phenylmethyl-7-trifluoromethyl-1H-benz[e]isoindole methanesulfonate salt.

Examples 86–89 listed below are prepared in accordance with the procedures described in Examples 6 and 7.

86) trans-2,3,3a,4,5,9b-Hexahydro-3-phenylmethyl-6-trifluoromethyl-1H-benz[e]isoindole methanesulfonic acid salt;
87) trans-2,3,3a,4,5,9b-Hexahydro-2-methyl-3-phenylmethyl-6-trifluoromethyl-1H-benz[e]isoindole;
88) trans-2,3,3a,4,5,9b-Hexahydro-3-phenylmethyl-7-trifluoromethyl-1H-benz[e]isoindole methanesulfonic acid salt;
89) trans-2,3,3a,4,5,9b-Hexahydro-2-methyl-3-phenylmethyl-7-trifluoromethyl-1H-benz[e]isoindole.

Examples 90–95 listed below are prepared in accordance with the procedures described in Examples 11, 12 and 13.

90) cis-2,3,3a,4,5,9b-Hexahydro-3-(3-methylphenyl)-methyl-6-trifluoromethyl-1H-benz[e]isoindole hydrochloride;
91) cis-2,3,3a,4,5,9b-Hexahydro-2-methyl-3-(3-methylphenyl)methyl-6-trifluoromethyl-1H-benz[e]isoindole hydrochloride;
92) cis-2-Ethyl-2,3,3a,4,5,9b-hexahydro-3-(3-methylphenyl)methyl-6-trifluoromethyl-1H-benz[e]isoindole hydrochloride;
93) cis-2,3,3a,4,5,9b-Hexahydro-3-(3-methylphenyl)-methyl-7-trifluoromethyl-1H-benz[e]isoindole hydrochloride;
94) cis-2,3,3a,4,5,9b-Hexahydro-2-methyl-3-(3-methylphenyl)methyl-7-trifluoromethyl-1H-benz[e]isoindole hydrochloride;
95) cis-2-Ethyl-2,3,3a,4,5,9b-hexahydro-3-(3-methylphenyl)methyl-7-trifluoromethyl-1H-benz[e]isoindole hydrochloride.

Examples 96 and 97 listed below are prepared in accordance with the procedures described in Example 14.

96) trans-2,3,3a,4,5,9b-Hexahydro-2-methyl-3-(3-methylphenyl)methyl-6-trifluoromethyl-1H-benz[e]isoindole methanesulfonic acid salt;
97) trans-2,3,3a,4,5,9b-Hexahydro-2-methyl-3-(3-methylphenyl)methyl-7-trifluoromethyl-1H-benz[e]isoindole methanesulfonic acid salt.

Examples 98–101 listed below are prepared in accordance with the procedures described in Examples 15 and 16.

98) cis-3-(3-Fluorophenyl)methyl-2,3,3a,4,5,9b-hexahydro-6-trifluoromethyl-1H-benz[e]isoindole hydrochloride;
99) cis-3-(3-Fluorophenyl)methyl-2,3,3a,4,5,9b-hexahydro-2-methyl-6-trifluoromethyl-1H-benz[e]isoindole hydrochloride;
100) cis-3-(3-Fluorophenyl)methyl-2,3,3a,4,5,9b-hexahydro-7-trifluoromethyl-1H-benz[e]isoindole hydrochloride;
101) cis-3-(3-Fluorophenyl)methyl-2,3,3a,4,5,9b-hexahydro-2-methyl-7-trifluoromethyl-1H-benz[e]isoindole hydrochloride.

Examples 102–105 listed below are prepared in accordance with the procedures described in Examples 17 and 18.

102) 3-(4-Fluorophenyl)methyl-2,3,3a,4,5,9b-hexahydro-6-trifluoromethyl-1H-benz[e]isoindole methanesulfonic acid salt;
103) cis-3-(4-Fluorophenyl)methyl-2,3,3a,4,5,9b-hexahydro-2-methyl-6-trifluoromethyl-1H-benz[e]isoindole methanesulfonic acid salt;
104) 3-(4-Fluorophenyl)methyl-2,3,3a,4,5,9b-hexahydro-7-trifluoromethyl-1H-benz[e]isoindole methanesulfonic acid salt;
105) cis-3-(4-Fluorophenyl)methyl-2,3,3a,4,5,9b-hexahydro-2-methyl-7-trifluoromethyl-1H-benz[e]isoindole methanesulfonic acid salt.

TABLE 2

| Results of uptake inhibition studies - $IC_{50}$ (nM) | | | |
|---|---|---|---|
| Example No. | NE[1] | 5-HT[2] | DA[3] |
| 1 | 524 | 7290 | 7620 |
| 2 | 58 | 4162 | 182 |

TABLE 2-continued

Results of uptake inhibition studies - IC$_{50}$ (nM)

| Example No. | NE[1] | 5-HT[2] | DA[3] |
|---|---|---|---|
| 3 | 18 | 1396 | 225 |
| 6 | 543 | 6508 | 10100 |
| 7 | 322 | 12200 | 13400 |
| 8 | 120 | 2704 | 4700 |
| 9 | 48 | 6600 | 540 |
| 10 | 454 | 13500 | 6720 |
| 11 | 238 | 827 | 5143 |
| 12 | 37 | 1777 | 571 |
| 13 | 18 | 507 | 148 |
| 15 | 347 | 15000 | 7700 |
| 16 | 50 | 5450 | 441 |
| 17 | 665 | 11000 | 9200 |
| 18 | 241 | 2909 | 4822 |
| 21 | 758 | 13100 | 5490 |
| 22 | 60 | 3440 | 368 |
| 23 | 28 | 1432 | 141 |
| 24 | 104 | 2467 | 170 |
| 25 | 27 | 1900 | 197 |
| 26 | 603 | 2255 | 9040 |
| 27 | 189 | 2083 | 4590 |
| 28 | 78 | 1870 | 213 |
| 31 | 592 | 14000 | 5419 |
| 32 | 113 | 12705 | 169 |
| 36 | 62 | 964 | 952 |
| 38 | 261 | 3566 | 1331 |
| 47 | 41 | 1258 | 225 |
| 71A | 9.8 | 2120 | 450 |
| 71B | 11.9 | 2050 | 633 |
| 72 | 64 | 5750 | 1013 |
| 75A | 30 | 227 | 444 |
| 75B | 513 | 4130 | 2810 |
| 76A | 3.5 | 386 | 529 |
| 76B | 234 | 344 | 2190 |
| 77 | 189.7 | 4166 | 5169 |
| 78 | 9.7 | <1000 | 189 |

[1] NE = norepinephrine
[2] 5-HT = 5-hydroxytryptamine
[3] DA = dopamine

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

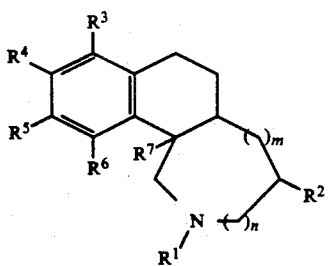

(I)

wherein
m is 0, 1 or 2 and n is 0 or 1, but m and n are never both 0;
$R^1$ is hydrogen or $C_1$–$C_6$-alkyl;
$R^2$ is $C_7$–$C_{16}$-arylalkyl, wherein the aryl group is unsubstituted or substituted with from one-to-three non-hydrogen members independently selected from the group consisting of halogen, $C_1$–$C_6$-alkyl, halo-$C_1$–$C_6$-alkyl, $C_1$–$C_6$-alkoxy, hydroxy, amino and $C_1$–$C_6$-alkylamino;
$R^3$, $R^4$, $R^5$ and $R^6$ are independently selected from the group consisting of hydrogen, $C_1$–$C_6$-alkoxy, $C_1$–$C_6$-alkyl, halogen and halo-$C_1$–$C_6$-alkyl, or any two of $R^3$, $R^4$, $R^5$ and $R^6$ taken together form a methylenedioxy group; and
$R^7$ is hydrogen, methyl or ethyl;
or a pharmaceutically-acceptable salt thereof.

2. A compound according to claim 1 wherein $R^1$ is hydrogen, methyl or ethyl.

3. A compound according to claim 2 wherein m is 1, n is 0, $R^7$ is hydrogen and $R^2$ is $C_7$–$C_{16}$-arylalkyl, wherein the aryl group is unsubstituted or substituted with from one to three non-hydrogen members independently selected from the group consisting of halogen, $C_1$–$C_6$-alkyl, halo-$C_1$–$C_6$-alkyl, $C_1$–$C_6$-alkoxy, hydroxy, amino and $C_1$–$C_6$-alkylamino.

4. A compound according to claim 2 wherein m is 2, n is 0, $R^7$ is hydrogen and $R^2$ is $C_7$–$C_{16}$-arylalkyl, wherein the aryl group is unsubstituted or substituted with from one to three non-hydrogen members independently selected from the group consisting of halogen, $C_1$–$C_6$-alkyl, halo-$C_1$–$C_6$-alkyl, $C_1$–$C_6$-alkoxy, hydroxy, amino and $C_1$–$C_6$-alkylamino.

5. A compound selected from:
2-Methyl-1,2,3,4,4a,5,6,10b-octahydro-3-phenylmethyl-benz[f]isoquinoline;
8-Methoxy-2-methyl-1,2,3,4,4a,5,6,10b-octahydro-3-phenylmethyl-benz[f]isoquinoline;
2-Methyl-1,3,4,5,5a,6,7,11b-octahydro-3-phenylmethyl-2H-naphth[1,2-c]azepine; and
8-Methoxy-2-methyl-1,3,4,5,5a,6,7,11b-octahydro-3-phenylmethyl-2H-naphth[1,2-c]azepine hydrochloride, and
(−)-cis-2-Methyl-1,3,4,5a,6,7,11b-octahydro-3-phenylmethyl-2H-naphth[1,2-c]azepine hydrochloride;
or a pharmaceutically-acceptable salt thereof.

6. A pharmaceutical composition for treating affective disorders comprising a therapeutically-effective amount of a compound as defined in claim 1 and a pharmaceutically-acceptable carrier.

7. A pharmaceutical composition for treating affective disorders comprising a therapeutically-effective amount of a compound selected from the compounds named in claim 5 and a pharmaceutically-acceptable carrier.

8. A method of treating affective disorders comprising administering to a patient in need of such treatment a therapeutically-effective amount of a compound as defined in claim 1.

9. A method of treating affective disorders comprising administering to a patient in need of such treatment a therapeutically-effective amount of a compound selected from the compounds named in claim 5.

10. A method according to claim 8 wherein the affective disorder being treated is depression.

* * * * *